(12) United States Patent
Whitelaw et al.

(10) Patent No.: US 8,530,724 B2
(45) Date of Patent: Sep. 10, 2013

(54) ALTERING THE FATTY ACID COMPOSITION OF RICE

(75) Inventors: Ella Whitelaw, Albury (AU); Sadequr Rahman, Nicholls (AU); Zhongyi Li, Kaleen (AU); Qing Liu, Girralang (AU); Surinder Pal Singh, Downer (AU); Robert Charles de Feyter, Monash (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 772 days.

(21) Appl. No.: 12/309,276

(22) PCT Filed: Jul. 13, 2007

(86) PCT No.: PCT/AU2007/000977
§ 371 (c)(1),
(2), (4) Date: Jul. 6, 2009

(87) PCT Pub. No.: WO2008/006171
PCT Pub. Date: Jan. 17, 2008

(65) Prior Publication Data
US 2009/0308041 A1    Dec. 17, 2009

(30) Foreign Application Priority Data

Jul. 14, 2006   (AU) ............................... 2006903810

(51) Int. Cl.
C12N 15/82      (2006.01)
C11B 1/00       (2006.01)
A23L 1/00       (2006.01)
A23D 7/00       (2006.01)

(52) U.S. Cl.
USPC ................. 800/281; 554/9; 426/601; 426/618

(58) Field of Classification Search
None
See application file for complete search history.

(56) References Cited

U.S. PATENT DOCUMENTS

| | | | |
|---|---|---|---|
| 4,948,811 A * | 8/1990 | Spinner et al. ............. 514/560 |
| 5,500,361 A | 3/1996 | Kinney et al. |
| 6,432,684 B1 | 8/2002 | Mukerji et al. |
| 7,589,253 B2 | 9/2009 | Green et al. |
| 7,807,849 B2 | 10/2010 | Singh et al. |
| 7,834,248 B2 | 11/2010 | Green et al. |
| 7,834,250 B2 | 11/2010 | Singh et al. |
| 7,932,438 B2 | 4/2011 | Singh et al. |
| 2004/0221335 A1 | 11/2004 | Shewmaker |
| 2005/0262588 A1 | 11/2005 | Dehesh |
| 2006/0053512 A1 | 3/2006 | Bao et al. |
| 2006/0094088 A1 | 5/2006 | Picataggio et al. |
| 2006/0206963 A1 | 9/2006 | Voelker et al. |
| 2008/0268539 A1 | 10/2008 | Singh et al. |
| 2011/0015415 A1 | 1/2011 | Singh et al. |
| 2011/0054198 A1 | 3/2011 | Singh et al. |
| 2011/0190521 A1 | 8/2011 | Damcevski et al. |
| 2011/0201065 A1 | 8/2011 | Singh et al. |
| 2011/0223311 A1 | 9/2011 | Liu et al. |
| 2011/0229623 A1 | 9/2011 | Liu et al. |
| 2012/0041218 A1 | 2/2012 | Singh et al. |

FOREIGN PATENT DOCUMENTS

| | | |
|---|---|---|
| WO | WO 99/049050 | 9/1999 |
| WO | WO 03/080802 | 10/2003 |
| WO | WO 2003/080802 A2 | 10/2003 |
| WO | WO 2004/001001 | 12/2003 |
| WO | WO 2004/001001 A2 | 12/2003 |
| WO | WO 2008/025068 | 6/2008 |
| WO | WO 2009/12958 | 10/2009 |
| WO | WO 2010/009500 | 1/2010 |
| WO | WO 2010/057246 | 5/2010 |

OTHER PUBLICATIONS

Supplementary European Search Report issued Feb. 23, 2010 in connection with corresponding European Patent Application No. 07763775.9.
Taira et al. (1989) "Fatty Acid Composition of Indica-Types and Japonica-Types of Rice Bran and Milled Rice" Journal of the American Oil Chemists' Society; vol. 66 No. 9, 1326-1329.
Taira et al. (1988) "Fatty Acid Composition of Indica Sinica Javanica and Japonica Groups of Nonglutinous Brown Rice" Journal of Agricultural and Food Chemistry; vol. 36 No. 1, 45-47.
Taira et al. (1986) "Lipid Content and Fatty-Acid Composition of Indica and Japonica Types of Nonglutinous Brown Rice" Journal of Agriculture and Food Chemistry; vol. 34 No. 3, 542-545.
Whitelaw et al. (1986) "A Rice FATB Insertional Mutant Exhibits Improved Growth and Reduced Photoinhibition at High Temperatures" Proceedings of the 55th Australian Cereal Chemistry Conference, 55th Australian Cereal Chemistry Conference, Jul. 3-7, 2008, Sydney Australia, Jul. 3, 2005, pates 101-104.
Stoutjesdijk et al. (2002) "hpRNA-mediated targeting of the Arabidopsis FAD2 gene gives highly efficient and stable silencing" Plant Physiology, American Society of Plant Physiologists, Rockville, MD, US; vol. 129, 1723-31.
Cicero et al. (2001) "Rice bran oil and [gamma]-oryzanol in the treatment of hyperlipoproteinaemias and other conditions" Phytotherapy Research; vol. 15 No. 4, 277-289.
Chapman et al. (2001) "Transgenic Cotton Plants with Increased Seed Oleic Acid Content" Journal of American Chemists' Chemistry; vol. 78 No. 9, 941-947.
Sivaraman et al. (2004) "Development of high oleic and low linoleic acid transgenics in a zero erucic acid Brassica juncea L. (Indian mustard) line by antisense suppression of the fad2 gene" Molecular Breeding, Kluwer Academic Publishers, DO; vol. 13 No. 1, 365-375.
Miquel et al. (1992) "Arabidopsis mutants deficient in polyunsaturated fatty acid synthesis: Biochemical and genetic characterization of a plant oleoyl-phosphatidylcholine desaturase" Journal of Biological Chemistry; vol. 267 No. 3, 1502-1509.

(Continued)

Primary Examiner — Elizabeth McElwain
(74) Attorney, Agent, or Firm — John P. White; Gary J. Gershik; Cooper & Dunham LLP

(57) ABSTRACT

The present invention relates to rice oil, rice bran and rice seeds which have altered levels of oleic acid, palmitic acid and/or linoleic acid. The present invention also provides methods for genetically modifying rice plants such that rice oil, rice bran and rice seeds produced therefrom have altered levels of oleic acid, palmitic acid and/or linoleic acid. Specifically this is achieved through modulation of Fad2 and/or FatB expression.

8 Claims, 38 Drawing Sheets

(56) References Cited

OTHER PUBLICATIONS

Figure 1:
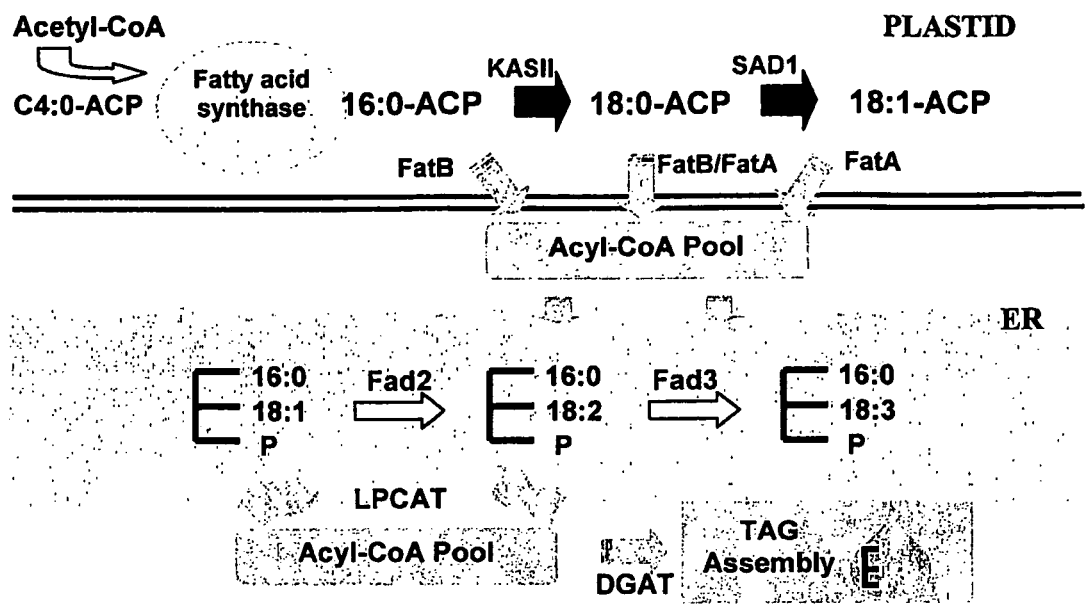

Chang et al., Chemical Reactions Involved in the Deep-Fat Frying of Foods. Journal of American Oil Chemists' Society, 1978, 55:718-727.
Wang et al., Improved Vectors for *Agrobacterium tumefaciens*—Mediated Transformation of Monocot Plants. Acta Hort, 1998, 461:401-407.
Akagi et al. (1995) Nucleotide Sequence of a Stearoyl-Acel carrier Protein Desaturase cDNA from Developing Seeds of Rice. Plant Physiol. 108, 845-846.
Anai et al. (2003) Improvement of rice (Oryza sativa L.) seed oil quality through introduction of a soybean microsomal omega-3 fatty acid desaturase gene. Plant Cell Rep. 21,988-992.
Ascherio and Willett (1997) Health effects of trans fatty acids. Am. J. Clin. Nutr. 66: 1006S-1010S.
Boggs et al. (1964) Relation of Hexanal in Vapor Above Stored Potato Granules to Subjective Flavor Extimates. J. Food Sci. 29:487-489.
Bonanome and Grundy (1988) Effect of Dietary Stearic Acid on Plasma Cholesterol and Lipoprotein Levels. N. Engl. Med. 318: 1244-1248.
Buhr et al. (2002) Ribozyme termination of RNA transcripts downregulate seed fatty acid genes in transgenic soybean. Plant J. 30: 155-163.
Champagne et al. (1995) Stabilization of Brown Rice Products Using Ethanol Vapors as an Antioxidant Delivery System. Cereal Chem 72:255-258.
Chapman et al., (2001). Transgenic Cotton Plants with Increased Seed Oleic Acid Content. J. Am. Oil Chem. Soc. 78: 941-947.
Choudhury et al. (1980) Lipids in Developing and Mature Rice Grain. Phytochemistry 19: 1063-1069.
Dougherty et al. (1995). Effects of diets containing high or low amounts of stearic acid on plasma lipoprotein fractions and fecal fatty acid excretion of men. Am. J. Clin. Nutr. 61:1120-1128.
Ha (2005) Bioactive components in rice bran oil improve lipid profiles in rats fed on high-cholesterol diet. Nutrition research 25, 597-606.
Hu et al. (1997). Dietary Fat Intake and the Rist of Coronary Heart Disease in Women. N. Engl. J. Med, 337: 1491-1499.
Jennings and Akoh (2000) Lipase-Catalyzed Modification of Rice Bran Oil to Incorporate Capric Acid. Journal of Agricultural and Food Chemistry, 48:4439-4443.
Jones et al. (1995) Palmitoyl-Acyl Carrier Protein (ACP) Thioesterase and the Evolutionary Origin of Plant Acyl-ACP Thioesterases. Plant Cell 7: 359-371.
Kinney (1996) Development of Genetically Engineered Soybean Oils for Food Applications. J. Food Lipids 3: 273-292.
Kodama et al. (1997) Structure, chromosomal location and expression of a rice gene encoding the microsome ω-3 fatty acid desaturase. Plant Molecular Biology 33:493-502.
Kohno-Murase et al. (2006). Production of *trans*-10, *cis*-12 conjugated linoleic acid in rice. Transgenic Research 15:95-100.
Leonard et al. (1997) *Cuphea wrightii* thioesterases have unexpected broad specificities on saturated fatty acids. Plant Molecular Biology, vol. 34, Issue 4: 669-679.
Liu et al. (1999) Molecular cloning and expression of a cDNA encoding a microsomal ω-6 fatty acid desaturase from cotton (*Gossypium hirsutism*) Aust. J. Plant Physiol. 26:101-106.
Liu et al. (2002). High-Oleic and High-Stearic Cottonseed Oils : Nutritionally Improved Cooking Oils Developed Using Gene Silencing. J. Am. Coll. Nutr. 21: 205S-211S.
Liu et al. (2002). High-Stearic and High-Oleic Cottonseed Oils Produced by Hairpin RNA-Mediated Post-Transcriptional Gene Silencing. Plant Physiol. 129: 1732-1743.
Mensink and Katan (1990). Effect of Dietary Trans Fatty Acids on High-Density and Low-Density Lipoprotein Cholesterol Levels in Healthy Subjects. N. Engl. J. Med. 323: 439-445.
Mikkilineni and Rocheford (2003) Sequence variation and genomic organization of fatty acid desaturase-2 (fad2) and fatty acid desaturase-6 (fad6) cDNAs in maize. Theor. Applied Genetics, 106, 1326-1332.
Moghadasian and Frohlich (1999) Effects of Dietary Phytosterols on Cholesterol Metabolism and Athersclerosis: Clinical and Experimental Evidence. Am. J. Med. 107: 588-94.
Morrison (1988) Lipids in Cereal Starches: A Review. J Cereal Sci. 8:1-15.
Most et al. (2005) Rice bran oil, not fiber, lowers cholesterol in humans. Am J Clin Nutr 81:64-8.
Nielsen et al. (2004) Formation of Volatile Compounds in Model Experiments with Crude Leek (*Allium ampeloprasum* Var. *Lancelot*) Enzyme Extract and Linoleic Acid or Linolenic Acid. Journal of Agricultural and Food Chemistry 52:2315-2321.
Noakes and Clifton (1998) Oil blends containing partially hydrogenated or interesterified fats: differential effects on plasma lipids. Am. J. Clin. Nutr. 98: 242-247.
Ohlrogge and Jaworski (1997) Regulation of Fatty Acid Synthesis. Annu Rev Plant Physiol Plant Mol Biol. 48:109-136.
Radcliffe et al. (1997) Serum Lipids in Rats Fed Diets Containing Rice Bran Oil or High-Linolenic Acid Safflower Oil. Biochemical Archives 13:87-95.
Resurreccion et al (1979) Nutrient Content and Distribution in Milling Fractions of Rice Grain. Journal of the Science of Food and Agriculture, 30: 475-481.
Roche and Gibney (2000) Effect of long-chain n-3 polyunsaturated fatty acids on fasting and postprandial triacylglycerol metabolism. Am. J. Clin. Nutr. 71: 232S-237S.
Rukmini and Raghuram (1991) Nutritional and Biochemical Aspects of the Hypolipidemic Action of Rice Bran Oil: A Review. Journal of the American College of Nutrition 10(6):593-601.
Shin et al. (1986) Correlation Between Oxidative Deterioration of Unsaturated Lipid and n-Hexanal during Storage of Brown Rice. J. Food Sci. 51:460-463.
St Angelo et al. (1980) Identification of Lipoxygenase-Linoleate Decomposition Products by Direct Gas Chromatography-Mass Spectrometry. J Lipids 1:45-49.
Stoutjesdijk et al., (2000). High-oleic acid Australian *Brassica napus* and *B. juncea* varieties produced by co-suppression of endogenous Δ12-desaturases. Biochem. Soc. Trans. 28: 938-940.
Stoutjesdijk et al. (2002) hpRNA-Mediated Targeting of the Arabidopsis FAD2 Gene gives Highly Efficient and Stable Silencing. Plant Physiology 129: 1723-1731.
Suzuki et al. (1999) Volatile Components in Stored Rice [Oryza sativa (L.)] of Varieties with and without Lipoxygenase-3 in Seeds. J. Agric. Food Chem. 47: 1119-1124.
Taira and Chang (1986) Lipid content and fatty acid composition of Indica and Japonica types of nonglutinous brown rice. Agric. Food Chem. 34:542-545.
Thelen and Ohlrogge (2002) Metabolic Engineering of Fatty Acid Biosynthesis in Plants. Metabolic Engineering 4: 12-21.
Theriault et al. (1999). Tocotrienol: A Review of its Therapeutic Potential. Clin. Biochem. 32; 309-19.
Tholstrup et al. (1994)Fat high in stearic acid favorably affects blood lipids and factor VII coagulant activity in comparison with fats high in palmitic acid or high in myristic and lauric acids. Am. J. Clin. Nutr. 59: 371-377.
Tsugita et al (1983) Cooking Flavor and Texture of Rice Stored under Different Conditions. Agricultural and Biological Chemistry 47: 543-549.
Tsuzuki et al (2004) Oxidation Rate of Conjugated Linoleic Acid and Conjugated Linolenic Acid is Slowed by Triacylglycerol Esterification and α-Tocopherol. Lipids 39:475-480.
Voelker et al. (1996). Genetic engineering of a quantitative trait: metabolic and genetic parameters influencing the accumulation of laurate in rapeseed. Plant J. 9: 229-241.
Williams et al. (1999) Impaired Endothelial Function Following a Meal Rich in Used Cooking Fat. J. Am. Coll. Cardiol. 33:1050-1055.
Yasumatsu et al. (1966) Studies on Cereals Part V Stale Flavor of Stored Rice. Agric. Biol. Chem. 30:483-486.
Zhou et al. (2002) Ageing of Stored Rice: Changes in Chemical and Physical Attributes. Journal of Cereal Science 35:65-78.
Zock et al. (1994) Impace of myristic acid versus palmitic acid on serum lipid and piloprotein levels in healthy women and men. Arterioscler Thromb. 14: 567-575.

Connolly et al. (1998) GenBank Accession No. AC004236, NCBI, pp. 1-11.
Sharma et al., (2003) GenBank Accesion No. AC108870, NCBI, pp. 1-27.
Kim et al., (1999) GenBank Accesion No. AF213480, NCBI, p. 1.
Sasaki et al., (2001) GenBank Accession No. AP004047, NCBI, pp. 1-36.
Sasaki et al., (1999) GenBank Accession No. AP000399, NCBI, pp. 1-33.
Sasaki et al., (2001) GenBank Accession No. AP004236, NCBI, pp. 1-37.
Sasaki et al., (2002) GenBank Accession No. AP005168, NCBI, pp. 1-31.
Sasaki et al., (2002) GenBank Accession No. AP005291, NCBI, pp. 1-38.
Response to First Office Action filed with the Chinese Patent Office on Jan. 11, 2011 in connection with Chinese Patent Application No. 200780033971.4, and an English Translation of the Claims.
Response to Second Office Action and English Translation of Claims, filed with the Chinese Patent Office on Aug. 3, 2011 in connection with Chinese Patent Application No. 200780033971.4, and an English Translation of the Claims.
European Examination Report issued Jun. 8, 2010 by the European Patent Office in connection with European Patent Application No. 07763775.9.
Response to European Examination Report, filed with the European Patent Office in Connection on Dec. 16, 2010 in connection with European Patent Application No. 07763775.9.
European Examination Report issued Apr. 1, 2011 by the European Patent Office in connection with European Patent Application No. 07763775.9.
Response to European Examination Report, filed with the European Patent Office in Connection on Oct. 3, 2011 in connection with European Patent Application No. 07763775.9.
Abdullah et al., Efficient Plant Regeneration from Rice Protoplasts Through Somatic Embryogenesis. Biotechnology, 1983, 4:1087-1090.
Almeida and Allshire, RNA silencing and genome regulation. Trends in Cell Biology, 2005, 15:251-258.
Bligh and Dyer, Orange-red Flesh in Cod and Haddock. J. Fish. Res. Bd. Canada, 1959, 16(4):449-452.
Brandt et al., Primary Structure of a B1 Hordein Gene from Barley. Carlsberg Res. Commun., 1985, 50:333-345.
Broun et al., A bifunctional oleate 12-hydroxylase: desaturase from *Lesquerella fendleri*. The Plant Journal, 1998, 13(2):201-210.
Clapp et al., The 16-Kilodalton N-Terminal Fragment of Human Prolactin is a Potent Inhibitor of Angiogenesis. Endocrinology, 1993, 133(3):1292-1299.
Colot et al., Localization of sequences in wheat endosperm protein genes which confer tissue-specific expression in tobacco. The EMBO Journal, 1987, 6(12):3559-3564.
Comai et al., Efficient discovery of DNA polymorphisms in natural populations by Ecotilling. The Plant Journal, 2004, 37:778-786.
Haseloff and Gerlach, Simple RNA enzymes with new and highly specific endoribonuclease activities. Nature, 1988, 334:585-591.
Henikoff et al., Tilling. Traditional Mutagenesis Meets Functional Genomics. Plant Physiology, 2004, 135:630-636.
Kozeil et al., Optimizing expression of transgenes with an emphasis on post-transcriptional events. Plant Molecular Biology, 1996, 32:393-405.
Langridge et al., Trends in genetic and genome analysis in wheat: a review. Aust. J. Agric. Res., 2001, 52:1043-1077.
Lemieux B., High Throughput Single Nucleotide Polymorphism Genotyping Technology. Current Genomics, 2000, 1:301-311.
Li et al., Comparison of promoters and selectable marker genes for use in Indica rice transformation. Molecular Breeding, 1997, 3:1-14.
Lu et al., High Efficiency Retroviral Mediated Gene Transduction into Single Isolated Immature and Replatable CD34$^{3+}$Hematopoietic Stem/Progenitor Cells from Human Umbilical Cord Blood, J. Exp. Med., 1993, 178:2089-2096.
Millar and Waterhouse, Plant and animal microRNAs: similarities and differences. Funct Integr Genomics, 2005, 5:129-135.

Needleman and Wunsch, A General Method Applicable to the Search of Similarities in the Amino Acid Sequence of Two Proteins. J. Mol. Biol., 1970, 48:443-453.
Pasquinelli et al., MicroRNAs: a developing story. Current Opinion in Genetics & Development, 2005, 15:200-205.
Perriman et al., Extended target-site specificity for a hammerhead ribozyme. Gene, 1992, 113:157-163.
Senior I.J., Uses of Plant Gene Silencing. Biotechnology & Genetic Engineering Reviews, Ed. Tombs, M.P., 1998, 15:79-119.
Shippy et al., The Hairpin Ribozyme. Molecular Biotechnology, 1999, 12:117-129.
Slade and Knauf, Tilling moves beyond functional genomics into crop improvement. Transgenic Research, 2005, 14:109-115.
Smith et al., Total silencing by intron-spliced hairpin RNAs. Nature, 2000, 407:319-320.
Toriyama et al., Haploid and diploid plant regeneration from protoplasts of anther callus in rice. Theor Appl Genet, 1986, 73:16-19.
Wagner et al., Coupling of adenovirus to transferring-polylysine/DNA complexes greatly enhances receptor-mediated gene delivery and expression of transfected genes, Proc. Natl. Acad. Sci USA, 1992, 89:6099-6103.
Waterhouse, Virus resistance and gene silencing in plants can be induced by simultaneous expression of sense and antisense RNA. Proc. Natl. Acad. Sci. USA, 1998, 95:13959-13964.
U.S. Appl. No. 13/011,779, filed Jan. 21, 2011, Liu et al.
U.S. Appl. No. 12/989,405, filed May 16, 2011, Zhou et al.
U.S. Appl. No. 13/129,940, filed May 18, 2011, Petrie et al.
U.S. Appl. No. 13/011,773, filed Jan. 21, 2011, Liu et al.
U.S. Appl. No. 13/243,747, filed Sep. 23, 2011, Singh et al.
U.S. Appl. No. 13/171,032, filed Jun. 28, 2011, Petrie et al.
English translation of Office Action issued Aug. 27, 2010 in connection with corresponding Chinese Patent Application No. 200780033971.4.
Goffman et al. (2003) "Genetic Diversity for Lipid Content and Fatty Acid Profile in Rice Bran," Journal of the American Oil Chemists' Society 80:485-490.
International Search Report issued by the International Searching Authority (ISA/AU) on Oct. 25, 2007 in connection with International Application No. PCT/AU2007/000977.
WO 2005/063988 A1 (Pioneer Hi-Bred International, Inc.; E.I. Du Pont De Nemours and Company) Jul. 14, 2005.
WO 2000/011176 A2 (E.I. Du Pont De Nemours and Company) Mar. 2, 2000.
Buhr et al., "Ribozyme termination of RNA transcripts down-regulate seed fatty acid genes in transgenic soybean", The Plant Journal, 2002, 30(2):155-163.
Stoutjesdijk et al., "High-oleic acid Australian *Brassica napus* and *B. juncea* varieties produced by co-suppression of endogenous Δ12-destaturases", Biochemical Society Transactions, 2000, 28:938-940.
WO 2007/103738 A2 (Pioneer Hi-Bred International, Inc; E.I. Du Pont De Nemours and Company) Sep. 13, 2007.
Whitelaw, E. S., Li, Z., Singh, S., Liu, Q., Upadhyaya, N., Merell, M.. Rahman, S. (Sep. 2004), Investigation of lipid synthesis in the rice grain: [m]odification of fatty acids in rice bran oil, in C. K. Black, J. F. Panozzo, & G. J. Rebetzke (Eds.), *Cereals 2004: Proceedings of the 54$^{th}$ Australian Cereal Chemistry Conference and 11$^{th}$ Wheat Breeders Assembly*, Sep. 21-24, 2004, Canberra ACT, North Melbourne VIC: Cereal Chemistry Division, Royal Australian Chemical Institute, AU (pp. 418-420).
Third Office Action which issued on Nov. 16, 2011 in connection with Chinese Patent Application No. 200780033971.4, including English language translation.
Response filed to the third Office Action filed on Apr. 5, 2012 in connection with Chinese Patent Application No. 200780033971.4, including English language copy of the claims.
Fourth Office Action which issued on Aug. 3, 2012 in connection with Chinese Patent Application No. 200780033971.4, including English language translation.
Examination Report which issued on Jun. 8, 2012 in connection with Australian Patent Application No. 2007272316.
English language translation of First Office Action which issued on Oct. 16, 2012 in connection with Japanese Patent Application No.

GenBank Accession No. BAC45170.1, Sasaki et al. (2002).
GenBank Accession No. BAC45173.1, Sasaki et al. (2002).
Bäumlein, H., et al., (1991) "A Novel Seed Protein Gene From *Vicia faba* is Developmentally Regulated in Transgenic Tobacco and Arabidopsis Plants," Molecular and General Genetics, 225(3): 459-467.
Domergue et al., (2005) "In vivo characterization of the first acyl-CoA Δ6-desaturase from a member of the plant kingdom, the microalga *Ostreococcus tauri*," Biochem J. 389, 483-490.
Lee, M., et al., (1998) "Identification of Non-Heme Diiron Proteins That Catalyze Triple Bond and Epoxy Group Formation," Science, 280(5365): 915-918.
Trautwein, E.A., (2001) "n-3 Fatty Acids—Physiological and Technical Aspects for Their Use in Food," European Journal of Lipid Science and Technology, 103(1): 45-55.
Valvekens, D., et al,, (1988) "Agrobacterium tumefaciens-Mediated Transformation of Arabidopsis thaliana Root Explants by Using Kanamycin Selection," Proceedings of the National Academy of Sciences of the United States of America, 85(15) 5536-5540.
van de Loo, F. J., Broun, P., Turner, S., & Somerville, C. (Jul. 1995). An oleate 12-hydroxylase from *Ricinus communis* L. is a fatty acyl desaturase homolog. Proc. Natl. Acad. Sci. USA, 92, 6743-6747.
File History of U.S. Patent Publication No. 2011-0314725, Petrie et al., published Dec. 29, 2011 (U.S. Appl. No. 13/171,032, filed Jun. 28, 2011).
File History of U.S. Patent Publication No. 2011-0223311, Liu et al., published Sep. 15, 2011 (U.S. Appl. No. 13/011,773, filed Jan. 21, 2011).
File History for U.S. Patent Publication No. 2009-0308041, Whitelaw et al., Dec. 17, 2009 (U.S. Appl. No. 12/309,276, filed Jul. 6, 2009).
File History of U.S. Patent Publication No. 2011-0229623, Liu et al., Sep. 22, 2011 (U.S. Appl. No. 13/011,779, filed Jan. 21, 2011).
Feb. 20, 2013 Examination Report issued in connection with European Patent Application No. 07763775.9.
Feb. 6, 2012 European Examination Report issued in connection with European Patent Application No. 07763775.9.
Dec. 4, 2012 Request for Further Processing and Response to Feb. 6, 2012 European Report filed in connection with European Patent Application No. 07763775.9.
Dec. 18, 2012 Response to Aug. 3, 2012 Chinese Office Action filed in connection with Chinese Patent Application No. 200780033971.4.
Jan. 9, 2013 Office Action issued in connection with U.S. Appl. No. 13/011,773.
Feb. 11, 2013 Response filed in connection with U.S. Appl. No. 13/011,773.
Apr. 9, 2013 Office Action issued in connection with U.S. Appl. No. 13/011,773.
Dec. 6, 2012 Office Action issued in connection with U.S. Appl. No. 13/011,779.
Jan. 4, 2013 Response filed in connection with U.S. Appl. No. 13/011,779.
Mar. 13, 2013 Office Action issued in connection with U.S. Appl. No. 13/011,779.
Agarwal et al. (2003) "Cottonseed Oil Quality, Utilization and Processing" CICR Technical Bulletin No. 25, pp. 1-16.
Dubois et al. (2007) "Fatty acid profiles of 80 vegetable oils with regard to their nutritional potential" European Journal of Lipid Science Technology 109(7):710-732.
Klahre et al. (2002) "High molecular weight RNAs and small interfering RNAs induce systemic posttranscriptional gene silencing in plants." PNAS 99(18): 11981-11986.
Liu et al. (1997) EMBL Nucleotide Sequence Database as X97016.
O'Brien (2005) "Cottonseed Oil" Bailey's Industrial Oil and Fat Products, 6th Edition, edited by Fereidoon Shahidi.
Pirtle et al. (1999) "Characterization of a Palmitoyl-Acyl Carrier Protein Thioesterase (FatB1) in Cotton" Plant Cell Physiology 40:2 p 155-163.

* cited by examiner

```
                   1           11          21          31          41          51
proteinFATB2    MAGSLAASAFFPGPGSSPAASARSSKNAAVTGELPENLSVRGIVAKPNPPAAMQVKA..
proteinFATB3    MAGSLAASAFFPGPGSSPAASARSSKNAAVTGELPENLSVCGIVAKPNPPAAMQVKA..
proteinFATB1    MAGSLAASAFFPVPGSSPAASARSSKN..TTGELPENLSVRGIVAKPNPSPGAMQVKA..
proteinFATB4    MAGSIAASAFLPG...SPAAAPPKS....VLGERPDSLDVRGIAAKPGSSSAAALRAGK 61          71          81          91         101         111
proteinFATB2    ..QAQTLPKVNGTKVNLKTVKPD.MEETVPYSAPKTFYNQLPDWSMLLAAITTIFLAAEK
proteinFATB3    ..QAQTLPKVNGTKVNLKTVKPD.MEETVPHSAPKTFYNQLPDWSMLLAAITTIFLAAEK
proteinFATB1    ..QAQALPKVNGTKVNLKTTSPD.KEDIIPYTAPKTFYNQLPDWSMLLAAVTTIFLAAEK
proteinFATB4    TRTHAAIPKVNGGSSALADPEHDTMSSSSSAAPRTFYNQLPDWSMLLAAITTIFLAAEK 121         131         141         151         161         171
proteinFATB2    QWTLLDWKPKKPDMLVDTFGFGRIIQDGMVFRQNFMIRSYEIGADRTASIETLMNHLQET
proteinFATB3    QWTLLDWKPKKPDMLVDTFGFGRIIQDGMVFRQNFMIRSYEIGADRTASIETLMNHLQET
proteinFATB1    QWTLLDWKPKKPDMLADTFGFGRIIQDGLVFRQNELIRSYEIGADRTASIETLMNHLQET
proteinFATB4    QWTLLDWKPKRPDMLTDTFGFGRMIHEGLMFRQNFSIRSYEIGADRTASIETLMNHLQET 181         191         201         211         221         231
proteinFATB2    ALNHVRTAGLLGDGFGATPEMSKRNLIWVVSKIQLLVEQYPAWGDTVQVDTWVAAAGKNG
proteinFATB3    ALNHVRTAGLLGDGFGATPEMSKRNLIWVVSKIQLLVEQYPAWGDMVQVDTWVAAAGKNG
proteinFATB1    ALNHVKTAGLLGDGFGATPEMSKRNLIWVVSKIQLLVERYPSWGDMVQVDTWVAAAGKNG
proteinFATB4    ALNHVKSAGLLGDGFGSTPEMSKRDLFWVVSQMQAIVERYPCWGDTVEVDTWVGAHGKNG 241         251         261         271         281         291
proteinFATB2    MRRDWHVRDYNSGRTILRATSVWVMMHKKTRRLSKMPDEVRAEIGPYFNDRSAITEEQSE
proteinFATB3    MRRDWHVRDYNSGRTILRATSVWVMMHKKTRRLSKMPDEVRAEIGPYFNDRSAITEEQSE
proteinFATB1    MRRDWHVRDYNSGQTILRATSVWVMNKNTRRLSKMPDEVRAEIGPYENGRSAISEEQGE
proteinFATB4    MRRDWHIRDSVTGHTILKATSKWVMHKLTRRLARIPDEVRTEIEPYFFEHASIVDEDNQ
```

Figure 2

```
               301       311       321       331       341       351
proteinFATB2   KLAKTGNKVGDDATEQFIRKGLTPRWGDLDVNQHVNNVKYIGWILESAPISVLEKHELAS
proteinFATB3   KLA*~~~~~~~~~~~~~~~~~~~~~~~~~~~~~~~~~~~~~~~~~~~~~~~~~~~~~~~
proteinFATB1   KLPKPGTTFDGAATKQFTRKGLTPKWSDLDVNQHVNNVKYIGWILESAPISILEKHELAS
proteinFATB4   KLPKLPD.IEGANVAKYVRTGLTPRWADLDINQHVNNVKYIGWILESAPISILEKHELAS 361       371       381       391       401       411
proteinFATB2   MTLDYRKECGRDSVLQSLTTVSGECTSIGADKQASAIQCDHLLQLESGADIVKAHTEWRP
proteinFATB3   ~~~~~~~~~~~~~~~~~~~~~~~~~~~~~~~~~~~~~~~~~~~~~~~~~~~~~~~~~~~
proteinFATB1   MTLDYRKECGRDSVLQSLTAVSGECDDGNTE...SSIQCDHLLQLESGADIVKAHTEWRP
proteinFATB4   IVLDYRKECGRDSVLQSHTTVYTDC...NKHSGQTTLHCEHLLSLESGPTIVKARTMWRP 421       431
proteinFATB2   KRSHAAAENA*~~~~~~~~
proteinFATB3   ~~~~~~~~~~~~~~~~~~~
proteinFATB1   KRAQGEGNMGFFPAESA*~
proteinFATB4   KGTRPQESIIPSSS*~~~~
```

Figure 2a

```
LOC_Os02g4    CCATATGTGCAGCATAAAAGGCAAATCAGCCCTGTTTGACATGGCTCCAATGCTTAAATT
LOC_Os11g4    ------------------------------------------------------------
LOC_Os06g0    ------------------------------------------------------------
LOC_Os06g3    ------------------------------------------------------------

1981       1991       2001       2011       2021       2031
LOC_Os02g4    CTTTAGAGAAAAAACAGACTTTGTAGATTAAATCAAAGTGGCATAATCTTTTTATTTTGA
LOC_Os11g4    ------------------------------------------------------------
LOC_Os06g0    ------------------------------------------------------------
LOC_Os06g3    ------------------------------------------------------------

2041       2051       2061       2071       2081       2091
LOC_Os02g4    TAAAAATATTAGAAAATATCATACCCTAATATTCTTAGCATAGTACTCCATTCATCTCAC
LOC_Os11g4    ------------------------------------------------------------
LOC_Os06g0    ------------------------------------------------------------
LOC_Os06g3    ------------------------------------------------------------

2101       2111       2121       2131       2141       2151
LOC_Os02g4    TTATTAAGGTACGATCAAACTTGGCATAGTCTTCAAAGGCTGTGTTCTTTCCCCCATTTT
LOC_Os11g4    ------------------------------------------------------------
LOC_Os06g0    ------------------------------------------------------------
LOC_Os06g3    ------------------------------------------------------------

2161       2171       2181       2191       2201       2211
LOC_Os02g4    CCTAACCCATCTATCTCGTTTTCCGCGCACACATTTTTCAAACTGCTAAACGGTGTGATT
LOC_Os11g4    ------------------------------------------------------------
LOC_Os06g0    ------------------------------------------------------------
LOC_Os06g3    ------------------------------------------------------------

2221       2231       2241       2251       2261       2271
LOC_Os02g4    TATGCAAAAACTTCTATATGAAAGTTGTTTAAAAAAATCATATTAATCCATTTTTTAAAA
LOC_Os11g4    ------------------------------------------------------------
LOC_Os06g0    ------------------------------------------------------------
LOC_Os06g3    ------------------------------------------------------------

2281       2291       2301       2311       2321       2331
LOC_Os02g4    AAATCAGTTAATACTTAATTAATCATGCAATAAAACGAACTTCATTTTGCGTGCTGGGGA
LOC_Os11g4    ------------------------------------------------------------
LOC_Os06g0    ------------------------------------------------------------
LOC_Os06g3    ------------------------------------------------------------

2341       2351       2361       2371       2381       2391
LOC_Os02g4    GGAGGGGCTCCCAACCCCTCCTCCGAACACAGCCAAAAGCTACTTTTGGACTTTAAATTT
LOC_Os11g4    ------------------------------------------------------------
LOC_Os06g0    ------------------------------------------------------------
LOC_Os06g3    ------------------------------------------------------------

2401       2411       2421       2431       2441       2451
LOC_Os02g4    GTCATATATTATAATGTTTCTAGTAACAAAACCATAGTCATATGAAAGTAAATTTAAATG
LOC_Os11g4    ------------------------------------------------------------
LOC_Os06g0    ------------------------------------------------------------
LOC_Os06g3    ------------------------------------------------------------

2461       2471       2481       2491       2501       2511
LOC_Os02g4    ATAATCCAATGATATTATTTTCATCAAATAGAATTTAATTTATAATAAACTATTTATTGA
LOC_Os11g4    ------------------------------------------------------------
LOC_Os06g0    ------------------------------------------------------------
LOC_Os06g3    ------------------------------------------------------------

2521       2531       2541       2551       2561       2571
LOC_Os02g4    TAAAATATTCAGAGAGTTGAATATTAAAATACCTGTGTGCCTTAGTGAGTGGGCCAAATT
LOC_Os11g4    ------------------------------------------------------------
LOC_Os06g0    ------------------------------------------------------------
LOC_Os06g3    ------------------------------------------------------------
```

Figure 4a

```
                      2581      2591      2601      2611      2621      2631
LOC_Os02g4    AATTAATGGAGTAGTAACAGCTTTAACCAAAGAAATTTCAACAATTTCCCAAGCTAGAAA
LOC_Os11g4    ------------------------------------------------------------
LOC_Os06g0    ------------------------------------------------------------
LOC_Os06g3    ------------------------------------------------------------

2641      2651      2661      2671      2681      2691
LOC_Os02g4    AAACCCAACTCCAAAATAAACTTGAGTTAGAACTGTGTTAAGCACCTAAATTGTAATACC
LOC_Os11g4    ------------------------------------------------------------
LOC_Os06g0    ------------------------------------------------------------
LOC_Os06g3    ------------------------------------------------------------

2701      2711      2721      2731      2741      2751
LOC_Os02g4    TGTTACTCTCTCGTTCTCATTCTATATTTGTCCTAAGTTAAATATATCTACCTTTTTTTA
LOC_Os11g4    ------------------------------------------------------------
LOC_Os06g0    ------------------------------------------------------------
LOC_Os06g3    ------------------------------------------------------------

2761      2771      2781      2791      2801      2811
LOC_Os02g4    TCTGTCCTAAGTTAACTATGTGTATGTCTATCTTTTCTACTACTCCCTCCGTTTCAGGTT
LOC_Os11g4    ------------------------------------------------------------
LOC_Os06g0    ------------------------------------------------------------
LOC_Os06g3    ------------------------------------------------------------

2821      2831      2841      2851      2861      2871
LOC_Os02g4    ATAAGACGTTTTGACTTTGGTCAAAGTCAAACTGCTTTAAGTTTGACTAAGTTTGTAGAA
LOC_Os11g4    ------------------------------------------------------------
LOC_Os06g0    ------------------------------------------------------------
LOC_Os06g3    ------------------------------------------------------------

2881      2891      2901      2911      2921      2931
LOC_Os02g4    AAAATAATAACATTTTCAACCCAAGACAAATTTATTATGAAAATATGTTCAATTATTGAT
LOC_Os11g4    ------------------------------------------------------------
LOC_Os06g0    ------------------------------------------------------------
LOC_Os06g3    ------------------------------------------------------------

2941      2951      2961      2971      2981      2991
LOC_Os02g4    TTAATGAAACTAATTTGGTATTATAAATATTATTATATTTATATATAAACTTAGTTAAAT
LOC_Os11g4    ------------------------------------------------------------
LOC_Os06g0    ------------------------------------------------------------
LOC_Os06g3    ------------------------------------------------------------

3001      3011      3021      3031      3041      3051
LOC_Os02g4    TTAAAGTAGTTTAAGTTTGATCAAAGTCAAAATGTTTTATAACCTGAAATGGAGGGAGTA
LOC_Os11g4    ------------------------------------------------------------
LOC_Os06g0    ------------------------------------------------------------
LOC_Os06g3    ------------------------------------------------------------

3061      3071      3081      3091      3101      3111
LOC_Os02g4    AGTAATTTGAAACGAAGAGAGCAGACAAATAATAAACTAGTAAAGCCTGTGACTTGGGTT
LOC_Os11g4    ------------------------------------------------------------
LOC_Os06g0    ------------------------------------------------------------
LOC_Os06g3    ------------------------------------------------------------

3121      3131      3141      3151      3161      3171
LOC_Os02g4    CTAGTCATTGATCGTGTACATGTAGGTCTTGTTTAGATCCCAAAAAATTTTAGCCAAAAC
LOC_Os11g4    ------------------------------------------------------------
LOC_Os06g0    ------------------------------------------------------------
LOC_Os06g3    ------------------------------------------------------------

3181      3191      3201      3211      3221      3231
LOC_Os02g4    CTCACATCAAATATTTGGACACATGCACCCCTACCAGTGTGTGGAGGCATTGCATACACG
LOC_Os11g4    ------------------------------------------------------------
LOC_Os06g0    ------------------------------------------------------------
LOC_Os06g3    ------------------------------------------------------------
```

Figure 4b

```
              3241      3251      3261      3271      3281      3291
LOC_Os02g4   AAACATGGAAAAGGAATCAACTTGAGAGGTTAGACCTGCTAGCTCTACTAGGTCTGGATG
LOC_Os11g4   ------------------------------------------------------------
LOC_Os06g0   ------------------------------------------------------------
LOC_Os06g3   ------------------------------------------------------------

3301      3311      3321      3331      3341      3351
LOC_Os02g4   GTCATGCATTTTTTTTTGAAAAAAAACCACGCTGCAAGCTCGACAGCCTCAACCTCAATGG
LOC_Os11g4   ------------------------------------------------------------
LOC_Os06g0   ------------------------------------------------------------
LOC_Os06g3   ------------------------------------------------------------

3361      3371      3381      3391      3401      3411
LOC_Os02g4   CAACCATGACAATAATATGCATGACAATGGTGTAGGAGAAAAGACACGTCGATAACCAAA
LOC_Os11g4   ------------------------------------------------------------
LOC_Os06g0   ------------------------------------------------------------
LOC_Os06g3   ------------------------------------------------------------

3421      3431      3441      3451      3461      3471
LOC_Os02g4   GGGCGCGGCTGCGCATACAAAGGCGGAGAGAAGGAACGATGGTGGCTCAAAAAGAAAGAG
LOC_Os11g4   ------------------------------------------------------------
LOC_Os06g0   ------------------------------------------------------------
LOC_Os06g3   ------------------------------------------------------------

3481      3491      3501      3511      3521      3531
LOC_Os02g4   CGTCGGTGGCAGTGGTGCGTGGAGCGACACTAAAGTTAGTGGTTGCTGATGGTCTCACAC
LOC_Os11g4   ------------------------------------------------------------
LOC_Os06g0   ------------------------------------------------------------
LOC_Os06g3   ------------------------------------------------------------

3541      3551      3561      3571      3581      3591
LOC_Os02g4   AATCCCTAATCGAAATATTTATTTTTTTTCACTTAGTATTGCTGATCCGTGGGCCACCAG
LOC_Os11g4   ------------------------------------------------------------
LOC_Os06g0   ---------------------------------------------------CGCGTCGTG
LOC_Os06g3   ------------------------------------------------------------

3601      3611      3621      3631      3641      3651
LOC_Os02g4   CCAATCATAAAGAAAAATGTTGAGATAAAAGGTGGAGTATCTTCCCCTTCCTTCCCTTTT
LOC_Os11g4   ------------------------------------------------------------
LOC_Os06g0   TGAGTTGGCGAGCCCGAGGAGCGGAGGCGGCCACAAGTCTAATCCGCGTCGTCTGCGCGT
LOC_Os06g3   ------------------------------------------------------------

3661      3671      3681      3691      3701      3711
LOC_Os02g4   TGACTCGAAAAAAAAAAGCGTCGGTGGCGGCCGTGCGTGTAACAACACTAAAGTTAGTGG
LOC_Os11g4   ------------------------------------------------------------
LOC_Os06g0   TCGTGGGCGAGGAGGAGAAAGAAGAGGAGGAAGAGAGGGAAGGGGGCTTGA--TTTGATT
LOC_Os06g3   ------------------------------------------------------------

3721      3731      3741      3751      3761      3771
LOC_Os02g4   TTGCTGGTGGTCTGACACAATCCCTAATCAAGTTTGATAATAATAATAATTTATTTCCTC
LOC_Os11g4   ------------------------------------------------------------
LOC_Os06g0   TGGGCGCGTCTCGTGGAGTATCCGGTGAGTTCTTGGCGATCTGGCGAGGCGAGTGATGAG
LOC_Os06g3   ------------------------------------------------------------

3781      3791      3801      3811      3821      3831
LOC_Os02g4   TTATTAGTATTGCTGATGCGTGGGCCACCAATCAATCGTAAAGAAAAAAAAATGTTGAGAT
LOC_Os11g4   ------------------------------------------------------------
LOC_Os06g0   TGATTCCTGCTGCTGCTGGGGGATTTTGGCGTGATTTTCGTTGGTTGCATTTTGTTTCTT
LOC_Os06g3   ------------------------------------------------------------

3841      3851      3861      3871      3881      3891
LOC_Os02g4   AAAGGTGGGGGTATCTTCTCCTTCTCTTTTTTTTGGCTAAAATAAAAGTGGTTTCTGG
LOC_Os11g4   ------------------------------------------------------------
LOC_Os06g0   TTTTTTTGTATCGATTTGTTGGAGCT-TTATTCGGTAGATCTGGTCGATTCCATGGTGAG
LOC_Os06g3   ------------------------------------------------------------
```

Figure 4c

```
              3901      3911      3921      3931      3941      3951
LOC_Os02g4    TAGTCTGACACAATCTCTAATCGAAATATTTATTTTTTTCTCTTAGTATTGCTGATACGT
LOC_Os11g4    ------------------------------------------------------------
LOC_Os06g0    TTGTATCGGCGCCGGAGTGATAGCTGATTCTGTTTTTTTGTGTGATTTTTTTTTTGTTTT
LOC_Os06g3    ----------------GCGATGCGAGCCTGTGTTGACAGCGGAGAA-AGCAGTGTAATCC 3961      3971      3981      3991      4001      4011
LOC_Os02g4    GGGCCACCAGCCAATAATAAAGAAAAAAAATGTTAGAGATAAAAGGCGGAGAGTATCTTC
LOC_Os11g4    ------------------------------------------------------------
LOC_Os06g0    GGAAATAGGGTTTGTGTCGAATTGAGGGCATTTTTTTTCCTTAGGCAATGCAGGAT-TTC
LOC_Os06g3    GGTCCCGCCACCGCAGCCGCCTCCACCTCTCTTCCCGGCGCCAATGGCCGCGTCGT-GAA 4021      4031      4041      4051      4061      4071
LOC_Os02g4    CCCTTCCTTTTTTTGGCGTAAATGAAAGAAAAGAGAAAATCTCCCGTCGTCTCCTTCCT
LOC_Os11g4    --------------------------AGAGGAGAAATTCTCCCGTCGTCTCCTTCCT
LOC_Os06g0    GTTTTGTATGTTTTTGCGTGGAATGGATATGAACAGACCTCGAACAAATGGAAGAAT--T
LOC_Os06g3    GCGCAGCAGCAGCAGCAGCGGAGACAGCGGCAGAAGCTTTGCCTAAGGTCGGTTTGC 4081      4091      4101      4111      4121      4131
LOC_Os02g4    TGCGCCAAGAAAGACGAGCCGCGGCTCAACACCGGAGGGGAGGGGCGC--CGATCTCCAT
LOC_Os11g4    TGCGCCAAGAAAGACGAGCCGCGGCTCAACAGCGGAGTGGAGGGGCGC--CGATCTCCAT
LOC_Os06g0    TGTATTTTGTATGATGGATTGCAATGCGATACTTGTTTGGGGCGTGATTCGATTGAAAT
LOC_Os06g3    CTCCCCGCCTCCGCCGCATTCCGGTTGGAGTTTTGTCCGTGTTCGTCGG-CGGTTTCT-T 4141      4151      4161      4171      4181      4191
LOC_Os02g4    CGCCAAGGAGAGCAGAGCAGGGGAGGGGA-----TCCTGGT-GAGCCTCCTCTTCCTGAT
LOC_Os11g4    CGCCGAGGAGAGCAGAGCAGGGGAGGGGAGGGGATCCTGGT-GAGCCTCCTCTTCCTGAT
LOC_Os06g0    AAATGAA-ATATTAGAGTTATTTTGGGAT-----TCCTGTTTGCTGCGCCTTTTTTTTTA
LOC_Os06g3    GGCTGGCCGGAT--GAATTGTTGTGGGGAGGGG-GAGGGGGAGGGGCTC-TCTCACGCAC 4201      4211      4221      4231      4241      4251
LOC_Os02g4    TCATCTCTCTCCCATT--CTAGCTTCGGGGGACT--ACTTTTGCCTGGAATTTGCTCGCG
LOC_Os11g4    TCACCTCTCTCTCATT--CTAGCTTCGGGGGACT--ACTTTTGCCTCGAATTTGCT----
LOC_Os06g0    GCATTTCT-TGATATGAACAAGAGAAGAAGGGCTGAATTTTTTTCTTAGCTTTGGAGGCA
LOC_Os06g3    TCGCTGCT-GGATTTCGGTTAGGTTTCGCGGCTGGGGGAATCGCGGGGGAATTCAGGATC 4261      4271      4281      4291      4301      4311
LOC_Os02g4    TTCGTTCGTGCGTTCGTTCGT--TAACCCTAGCTTCTTCTCTTCTAGATCTGGAGGAAGC
LOC_Os11g4    --------TGCGTTCGTTCGT--TAACCCTAGCTTCTTCTCTTCTAGATCTGGAGGAAGC
LOC_Os06g0    TTTACTGTCCCAGTATTTTCTCCTACCGGAAGCAGAATATTTTGTTTGATTGGAGGGTTG
LOC_Os06g3    TT---TGTTTTGTTAGTTCTTCTTTCGGGCGGGGTTGGATCTCGAGTAATCTGCGTCGTG 4321      4331      4341      4351      4361      4371
LOC_Os02g4    TCTTCTCCTCCTTAATT-------------TCAGAGCCTT---AATACAAGTAGTAACAG
LOC_Os11g4    TCTTCTCCTCCTTAATT-------------TCAGAGCCTT---AATACAAGTAGTAACAG
LOC_Os06g0    CCTCCCTTTGCCAAATTGAATCAAATGTTCTCGGATGTTTTAAAATTTCCGTGGACTCTT
LOC_Os06g3    TTATTTGCCGCGAGATT-------------TGGGTGTTTT---TTTTCTTCTCCGCAT 4381      4391      4401      4411      4421      4431
LOC_Os02g4    TTTAACCTCCCCC------ATGTCCCAAGTTGGATCCGCCCCTGCGAGTTCCGATATTGG
LOC_Os11g4    TTTAACCCCCCCCCCCCCCCATGTCCCAAGTTGGATCCGCCCCTGCGAGTTCCGATATTGG
LOC_Os06g0    TTTGCCCCAGGGGAGACCGCTTTTAGCAGCTGGATCCCGTGTTTTCATTTCAAGTTCTTG
LOC_Os06g3    CTTCTCTCTCGTT------CCTTCGTCTGTACGGTCTAGTGGTGGTCTACGGGCTACGGC 4441      4451      4461      4471      4481      4491
LOC_Os02g4    GTCCTCCCAATTCTCAATGCCATTTGTTCATCGGGGGGCATATGGTTCATTTTTGCCTG
LOC_Os11g4    GTCCTCCCAATTCTCAATGCCATTTGTTCATCGGGGGGCATATGGTTCATTTT-GCCTG
LOC_Os06g0    TT--TTCCTAGTCTCCATATATTTCTGATTGTTAACTCGTATTCTCTACCTCAC-ATATG
LOC_Os06g3    CGTGGTAAAAGTTTCTCTAGATTTTTGGTC-TCGTTTTTTTCTTTATTTTAGGCGGCTTG 4501      4511      4521      4531      4541      4551
LOC_Os02g4    CATTGATTCAAATGTGGTTTCGAATCGTTTGTGAAAT-TC-GCGGGTGTACTTGTTTATG
LOC_Os11g4    CATTGATTCAAATGTGGTTTCGAATCGTTTGGGAAAT-TC-GCGGGTGTACTTGTTTATG
LOC_Os06g0    CAAAATCACACTTGCGTCGTTCTGTAATTAGTTAGAT-TCTGCAAGAAAAATCCGGAATT
LOC_Os06g3    CTTTGCTTCGCCTGCTTTGACGTTTGACCAGCGGTTTATCCTCGATTATTCTTCCTCGTG
```

Figure 4d

```
                4561      4571      4581      4591      4601      4611
LOC_Os02g4    ATACATGAGGCCTTTTTTC-CCCCATGAGGAGGCAAACTTTTTAGTGGGTGGATCCACTA
LOC_Os11g4    ATATATGAGGCCTTTTTTTCCCCATGAGGAGGCAAACTTTTTAGTGGGTGGATCCACTA
LOC_Os06g0    TTCAAGCATGCTAGTAGTTTTAAATTGATG--CCATGTTTTTTAGACAATGT------TA
LOC_Os06g3    AGTCGTGA-GCAAGCTATG---ATTTGCAG--CTAATGATTTTGTGCTTGGATTAGATA 4621      4631      4641      4651      4661      4671
LOC_Os02g4    GTTCATGC--CTCA--ATT--TTTTTTCTCCTCTTTTAAGTTTTCCAAAGAGCTACATTG
LOC_Os11g4    GTTCATGC--CTCA--ATT--TTTTTTCTCCTCTTTTAAGTTTTCCAAAGAGCTACATTG
LOC_Os06g0    ATTGATGC--CATATGACT--ATAGGACACATTATATTGCGTTTCTGAATA--TACCACC
LOC_Os06g3    AAAGATGCTTCTCACTCTTCGTTTGTTTCCATTTTCTGGAATTTGTGATTTCCTGG--TG 4681      4691      4701      4711      4721      4731
LOC_Os02g4    TTGTAAAGTGTCTGATACAATTGATTGTTTATTCAGGTTAGCGCTTTTGGCGTG--TGAT
LOC_Os11g4    TTGTAAAGTGTCTAATACAATTGATTGTTTATTCAGGTTAGCGCTTTTGGCGTG--TGAT
LOC_Os06g0    TCATGAAACTCATAATTTTGTTGATTAATTGTTCAGGTTGCCCCTTCTAGTGTG--TAAC
LOC_Os06g3    ATGATAATGTTGTGCTCGTGTTGATTCAG-GTTGGGATCCTCCCTATTCGCGCGCGTCTT 4741      4751      4761      4771      4781      4791
LOC_Os02g4    TGATTTCTAAACGAATTTTGGGCCGTGAGGGGAAGTTCAATCATGGCAGGGTCTCTTGCC
LOC_Os11g4    TGATTTCTAAACGAATTTTGGGCCGTGAAGGGAAGTTCAATCATGGCAGGGTCTCTTGCC
LOC_Os06g0    T------TGGAGCAAATTTGGACCCTGAGACGCAAATCAGTCATGGCTGGTTCTCTTGCG
LOC_Os06g3    TGATTTGGCGCGTAAAGTTG-----TAATCCGTACTCCGG--ATGGCCGGCTCAATCGCC 4801      4811      4821      4831      4841      4851
LOC_Os02g4    GCCTCAGCATTCTTCCCAGGTCCAGGCTCATCTCCTGCAGCATCAGCTAGAAGCTCCAAG
LOC_Os11g4    GCCTCAGCATTCTTCCCAGGTCCAGGCTCATCTCCTGCAGCATCAGCTAGAAGCTCCAAG
LOC_Os06g0    GCGTCTGCATTCTTCCCTGTCCCAGGGTCTTCCCCTGCAGCTTCGGCTAGAAGCTCTAAG
LOC_Os06g3    GCCTCGGCGTTCTTGCCGG------GGTCGCCGGCGGCCGCGCCGCCCAAGAGCG-----

4861      4871      4881      4891      4901      4911
LOC_Os02g4    AATGCTGCTGTTACCGGCGAATTGCCGGAGAATTTGAGTGTCTGTGGCATTGTCGCAAAG
LOC_Os11g4    AATGCTGCTGTTACCGGCGAATTGCCGGAGAATTTGAGTGTCCGTGGCATTGTCGCAAAG
LOC_Os06g0    AACACA------ACCGGTGAATTGCCAGAGAATTTGAGTGTCCGCGGAATCGTCGCGAAG
LOC_Os06g3    --TCCTG---------GGCGAGCGCCCGGACAGCCTGGACGTCCGCGGCATCGCCGCGAAG 4921      4931      4941      4951      4961      4971
LOC_Os02g4    CCTAACCCACCTCCTGCAGCC---------ATGCAAGTAAAGGCACAGGCTCAAACCC--
LOC_Os11g4    CCTAACCCACCTCCTGCAGCC---------ATGCAAGTAAAGGCACAGGCTCAAACCC--
LOC_Os06g0    CCTAATCCGTCTCCAGGGGCC---------ATGCAAGTCAAGGCGCAGGCGCAAGCCC--
LOC_Os06g3    CCGGGCTCCTCGTCGTCGGCCGCCGCCCTGAGGGCCGGCAAGACGCGCACCCACGCCGCC 4981      4991      5001      5011      5021      5031
LOC_Os02g4    -TTCCCAAGGTTAATGGTACGAAGGTTAACCTCAAGACGGTGAAGCCTGACATGGAGGAA
LOC_Os11g4    -TTCCCAAGGTTAATGGTACGAAGGTTAACCTCAAGACGGTGAAGCCTGACATGGAGGAA
LOC_Os06g0    -TTCCTAAGGTTAATGGAACCAAGGTTAACCTGAAGACTACAAGCCCAGACAAGGAGGAT
LOC_Os06g3    ATCCCCAAGGTGAACGGCGGCAGTTCGGCGCTGGCGGATCCGGAGCACGACACG-ATGTC 5041      5051      5061      5071      5081      5091
LOC_Os02g4    ACGGTGC----CTCACAGTGCTCCAAAGACGTTCTATAACCAACTGCCGGATTGGAGCAT
LOC_Os11g4    ACGGTGC----CTTACAGTGCTCCAAAGACGTTCTATAACCAACTGCCGGATTGGAGCAT
LOC_Os06g0    ATAATAC----CGTACACTGCTCCGAAGACATTCTATAACCAATTGCCAGACTGGAGCAT
LOC_Os06g3    CTCCTCCTCCTCCGCGGCGCCGAGGACGTTCTACAACCAGCTCCCCGACTGGAGCAT

5101 .    5111      5121      5131      5141      5151
LOC_Os02g4    GCTTCTTGCGGCTATTACAACCATCTTCCTCGCCGCAGAGAAGCAGTGGACACTGCTTGA
LOC_Os11g4    GCTTCTTGCGGCTATTACAACCATCTTCCTTGCCGCAGAGAAGCAGTGGACACTGCTTGA
LOC_Os06g0    GCTTCTTGCAGCTGTCACGACCATTTTCCTGGCAGCTGAGAAGCAGTGGACTCTGCTTGA
LOC_Os06g3    GCTCCTCGCAGCCATCACGACCATCTTCTTGGCCGCGGAGAAGCAGTGGACGCTGCTGGA 5161      5171      5181      5191      5201      5211
LOC_Os02g4    TTGGAAGCCGAAGAAACCTGACATGCTTGTTGACACATTTGGCTTTGGTAGGATCATCCA
LOC_Os11g4    TTGGAAGCCAAAGAAACCTGACATGCTTGTTGACACATTTGGCTTTGGTAGGATTATCCA
LOC_Os06g0    CTGGAAGCCGAAGAAGCCTGACATGCTGGTCGACACATTCGGCTTTGGTAGGATCATCCA
LOC_Os06g3    CTGGAAGCCGAAGCGGCCCGACATGCTCACCGACACGTTCGGTTTCGGCAGGATGATACA
```

Figure 4e

```
              5221      5231      5241      5251      5261      5271
LOC_Os02g4    GGACGGTATGGTGTTTAGGCAGAACTTCATGATTCGGTCCTACGAGATTGGCGCTGATCG
LOC_Os11g4    GGACGGTATGGTGTTTAGGCAGAACTTCATGATTCGGTCCTACGAGATTGGTGCTGATCG
LOC_Os06g0    AGACGGGCTGGTGTTTAGGCAAAACTTCTTGATTCGGTCCTACGAGATTGGTGCTGATCG
LOC_Os06g3    TGAGGGGCTCATGTTCAGGCAGAACTTCTCGATTAGGTCCTATGAGATCGGGGCCGATAG 5281      5291      5301      5311      5321      5331
LOC_Os02g4    TACAGCTTCTATAGAGACATTGATGAATCATTTACAGGTAAGTGGTTGCAC--ATTCTGT
LOC_Os11g4    TACAGCTTCTATAGAGACATTGATGAATCATTTACAGGTAAGTGGTTGCAC--ATTCTGT
LOC_Os06g0    TACAGCTTCTATTGAGACATTAATGAATCATTTACAGGTGATACAATGGAGCTATGCTGC
LOC_Os06g3    GACGGCGTCTATAGAAACGCTGATGAACCATTTGCAGGTGAAATATTGTGAATTTTCAGG 5341      5351      5361      5371      5381      5391
LOC_Os02g4    TTTTAGTTTCATTTCTCATTTCAGCATTTTGTTATAGATTCGTATGTCTCTTTCAAGCTG
LOC_Os11g4    TTTTAGTTTTATTTCTCATTTCAGCATTTTGTTATAGATTCATATGTCTCTTTCAAGCTG
LOC_Os06g0    TTTAGCTTTTCTTCCGTATTTTTCACTATTGGTAC--AT---TATGTTCGTGGCATACTA
LOC_Os06g3    CGTCGGATTGCTCGGGC-----TGGGCATCAGAAC--ATTGAAATGTTTTTGGT------

5401      5411      5421      5431      5441      5451
LOC_Os02g4    GCAATTATTTAAAATTTTGCAGGAAACGGCTCTTAACCATGTAAGGACTGCTGGTCTTCT
LOC_Os11g4    GCAATTATTTAAAATTTTGCAGGAAACAGCTCTTAACCATGTGAGGACTGCTGGTCTTCT
LOC_Os06g0    ACTGTAATTTGAAGCTTTGCAGGAAACAGCTCTGAACCATGTGAAAACTGCTGGTCTCTT
LOC_Os06g3    ----T---TTGA-----TGCAGGAAACCGCACTGAATCATGTGAAGAGCGCTGGGCTGCT 5461      5471      5481      5491      5501      5511
LOC_Os02g4    TGGAGATGGTTTTGGGGCTACACCGGAGATGAGCAAACGGAACTTGATATGGGTTGTCAG
LOC_Os11g4    TGGAGATGGTTTTGGGGCTACACCGGAGATGAGCAAACGGAACTTGATATGGGTTGTCAG
LOC_Os06g0    AGGTGATGGTTTTGGTGCTACGCCGGAGATGAGCAAACGGAACTTAATATGGGTTGTCAG
LOC_Os06g3    AGGAGATGGTTTTGGCTCAACGCCAGAGATGAGTAAACGAGACTTGTTCTGGGTTGTCAG 5521      5531      5541      5551      5561      5571
LOC_Os02g4    CAAAATCCAGCTTCTTGTTGAGCAATACCCCGCATGGTACTTTTT-TGCAAACCTTTGCT
LOC_Os11g4    CAAAATCCAGCTTCTTGTTGAGCAATACCCCGCATGGTAGTTCTT-TGCAAACCTTTGCT
LOC_Os06g0    CAAAATTCAGCTTCTTGTTGAGCGATACCCATCATGGTACTTTTTCTGCAATCCA---CT
LOC_Os06g3    CCAAATGCAGGCAATCGTTGAGCGTTATCCGTGCTGCTGGTA----TAATACTATAAT---TT 5581      5591      5601      5611      5621      5631
LOC_Os02g4    CCTCTTGATATATGTATCTTTGGTTTCTTTCTATCAAT--TCCTTACTCTAAGTTGTCAT
LOC_Os11g4    CCTCTTAATATATGTATCTTTGGTTGCTTTCTATCAAT--TCCTTACCGTAAGTTTTCAT
LOC_Os06g0    ACTCTCCACATCATTTTCTTGGATGGCAAAACTTCTCT--TTTTACTCTTAATTCATAAC
LOC_Os06g3    -CACATATCAGCATGTTCTTGGTTTTGTTTTCTTACATAGTTTGAGCTCCAAATAGGGTG 5641      5651      5661      5671      5681      5691
LOC_Os02g4    TTAATTTTCACATTTTAAATTACTTCATATTTGTTTTGCTTCTTTTACAGATATCGTTTT
LOC_Os11g4    TT--TTGTCACATTTTAAATTACTTCATATTTGTTTGCTTCTTTTACAGATATCGTTTT
LOC_Os06g0    AT--TTCTTTCATTCTTAATGGAGTACTTTTGTCCCCGGTGCATTTAGTGTCACAATTTA
LOC_Os06g3    TTGCTTTTCTGCTTTCGTGTTACATGACAATT---AGGAGGCACATAGATGTATGGTTGG 5701      5711      5721      5731      5741      5751
LOC_Os02g4    ATGTACTACTTTACAGCTGTGTGTCCTTTGCATATTTGTTTTTATTTGTTTAAAGAAGAT
LOC_Os11g4    ATGTACTACTTTATAGCTGTGTGTCCTTGGCATATTTGTTTCTATTTGTTTAAAGAAGAT
LOC_Os06g0    ATG------TTTACA--TG---GTACGGGAAAGATTTATCACTCAATATCCACGGTGTAA
LOC_Os06g3    CTGTC--ACAGTACG--TTACTGTAGTTATAGTAGCTATCA-TCTTGCTTCACAGCAG--

5761      5771      5781      5791      5801      5811
LOC_Os02g4    TCTTACACAAGCAACAGTAGTATTTAGCTCAATATTTACTTTAACATGGTTTATCATATT
LOC_Os11g4    TCTTACTCAGGCAACAGTAGTATTTAGCTCAATATTTACTTTAACATGGTTTATCATAAT
LOC_Os06g0    TGTTTT----------TAGC--TAAACTCAATATCCACGGTGTAATGTTTTTAGCTAAA
LOC_Os06g3    TCATGG------AATAACAGG-TTTAGGTAAATGGA---GTTTTCAAGTTGTTTGGCAAT 5821      5831      5841      5851      5861      5871
LOC_Os02g4    GTTGTGTGGATCTCTGGTCTGATTTCTCCATACACTGGTTGGTTGATGAAAATCAAGTGA
LOC_Os11g4    GTTGTGTGGATCTCTGGTCTGATTTCTCCATATACTGGTTGGTTGATGAAAATCAAGTGA
LOC_Os06g0    CTTGTCTTCAGTCCTTTTTTCCTTTTTCCCTATGTTTGTGTGCTG-TGGCATTCGA-TGG
LOC_Os06g3    GAA-TATGAAAAA-------GATTTTCCCAAGT----GTTTGT--ATCAATTTTAAATGG
```

Figure 4f

```
              5881       5891       5901       5911       5921       5931
LOC_Os02g4    ATCTTTTACTTGCTCGTAAATTTCGCTGCTGCAGGTTTGCAAGAATATGGGTTGAAGTTT
LOC_Os11g4    ATCTTTTACTTGGTCGTATATTTCGCTGCTGCTGGTTTGCAAGAATATGGGTTGAAATTT
LOC_Os06g0    ATC----------------AT--CG-----------------AGACTCTGAGTAGACGTA-
LOC_Os06g3    ATG-------------------AGCAACT------------C-CCATCTCTTAACTGT- 5941       5951       5961       5971       5981       5991
LOC_Os02g4    TTATACTGCTATAGAAGGCCATGTTTTTCTTTGATTTCCCGTGATAGG-CCTCATGTTTT
LOC_Os11g4    TT--ACTGCTATAGAAGGCCATGTTTTTCTTTGATTTCCCGTGATAGG-CCTCATGTTTA
LOC_Os06g0    -G---------AT---------TCTTGCATTCCTTATGCGACATGAG-GCACATGTT--
LOC_Os06g3    ----------------------TTTTGCTATCGGCATTAAATATTTGTGCAACTGGT--

6001       6011       6021       6031       6041       6051
LOC_Os02g4    GGAGGTTCTGTTATTCCTCCTTGGTTGACTAAGAAATGTGTAGTAATATCAGCTCCAGTT
LOC_Os11g4    GGAGGTGCTGTTATTCCTCATTGGTTGACTAAGAAATGTGTAGTAATATCAGCTCCAGTT
LOC_Os06g0    CGAG----TGTTTATCACCCT------AC-ATGAAA--------ACCTTTCCCTACTAAG
LOC_Os06g3    AGACTTTCAGTAAACGATGAT--G---ATGCAGAAGCCT-------CCTGCTCTTAAT 6061       6071       6081       6091       6101       6111
LOC_Os02g4    TTGTTGGATCAAGGATAGATTTTGTGGCAAACTAAATTTTCCAATTAGGAAGAAATGAAT
LOC_Os11g4    TTGTTGGATCAAGGATAGAGTTTGTGGCAAACTAAATTTTCCAATTAGGAAGAAATGAAT
LOC_Os06g0    TTGCTGCTTCTA--------TTG-------------TTCTGCAGATAT-AAGCAAT--AT
LOC_Os06g3    ATTATTGATCATG--------TATC--------ATATTTTCTGTGAG-ATGTTAT--AA 6121       6131       6141       6151       6161       6171
LOC_Os02g4    ATATTCCTACTTAAGTGGG-AGGAGCATGCACTTTGTTTCCAATTGTCGAGCCCTGATTA
LOC_Os11g4    ATATTCCTACTTAAGTGGGGAGGAGCATGCACTTTGTTTCCAATTGTCGAGCCCTGATTA
LOC_Os06g0    TTTTGCCTATTT--TT---------CCTGTGCTTTGA--AC--TTCTCGTAG---GTTCA
LOC_Os06g3    TTGTTCGTGTTT--GTT---ACCTGAAAGTGCCATGTTGCCAATAATTAACTTCTTATCT 6181       6191       6201       6211       6221       6231
LOC_Os02g4    TAACACAAACTATCAAGTTATTTCTTTGCATTTAGAAACAGGATTTGCATCTTGGGTAAT
LOC_Os11g4    TAACACAAACTATCAAGTTATTTCTTTGCATTTAGAAACAGGATTTGCATCTTGAGTAAT
LOC_Os06g0    TGGCCCA------CAA-------CCT-----TTAG---CAGGCATAGTGCCTTGA-----
LOC_Os06g3    GTGTGCAGGGGTGATA-------CTGTCGAAGTAGATACATGGGTTGGTGCTCATG----

6241       6251       6261       6271       6281       6291
LOC_Os02g4    CCTCATTAAAGACATAATCTAGCTTTAGTACATGCAACATAAAAGTTATGATGCCCCAAG
LOC_Os11g4    CCTCATTAAAGACATAATCTAGCTTTAGTACATGCAACATAAAAGTTCTGATGCCCCAAG
LOC_Os06g0    ---------------AATGGAG---TATTACACTCAA-AA---------G----------
LOC_Os06g3    ----------GTAAAAATGGAA------TGCGCAGAGACT--------------------

6301       6311       6321       6331       6341       6351
LOC_Os02g4    GCCTTTTTGGTACAGCACTGTAAGTCTGTAGCTCTCCTTGCTCTATGTTGTCCTCAAAAG
LOC_Os11g4    GCCTTTTTGGTACAGCACTGTAAGTCTGTAGCTATCCTTGCTCTATGTTGTCCTCAAAAG
LOC_Os06g0    -----------CATA--ACAATAACA-TGTA--TTGCCTTG---TATGAT----------
LOC_Os06g3    --------GGCATAT-AC-GTGATTCTGTAACAGGCCATACAATATTGA-----------

6361       6371       6381       6391       6401       6411
LOC_Os02g4    ACACAACATCAGTTAAAA--------GAACAGTAATCTCTCCTTTAGACGTCAATTATTA
LOC_Os11g4    ACACAACATCAGTTAAAAAACAAAGAAGAACAGTAATCTCT-----TAGACGTCAGTTATTA
LOC_Os06g0    ----AAGATGAGTGATAG-----------------ATCT-----TTTGAAATCATTTACT-
LOC_Os06g3    AGGCTACAAG-GTTTGAAT-------------TATTGTCACTCTCATAAAT-ACTGATGA 6421       6431       6441       6451       6461       6471
LOC_Os02g4    GTGGAGTAGTAATTTAGATCCAAGAGCAACTTCATTTGTTACGCCTTATTCATTGCCCAA
LOC_Os11g4    GTGGAGTAGTAATTTAGATCCAAGAGCAACTTCATTTGTTACGCCTTATTCATTGCCCAA
LOC_Os06g0    ---GAGGAAAACGTTTGTTT--------ATTTGACAAG--ACAATGTATTGATGAACTAG
LOC_Os06g3    T--CATGAAAACTGTATTAGCATCTGCTATTCAACTTCCTAC-CCATCTTATT--ACCAC 6481       6491       6501       6511       6521       6531
LOC_Os02g4    AGCTGCCTCATTAAATGATGTCTTCTCTGTGCTTCCTTGGATCTTGAATTATGCTGAGTG
LOC_Os11g4    AGCTGCCTCATTAAATGATGTCTTCTCTGTGCTTCCTTGGATCTTGAATTATGTTGAGTG
LOC_Os06g0    AACTGCTCTATTAAGTGGTATCTGCCCTGTGTCTCCTT---TCGTACAAATTGTTGC---
LOC_Os06g3    TGTTTGCATATGAAGTC-TAGAAGTTCTGTTTCTTCTG---AACATATTATAAGCTGCCT-
```

Figure 4g

```
                 6541      6551      6561      6571      6581      6591
LOC_Os02g4   GGAATGCCAGAACGGGCATGTACTTACGTTTTCCAGCGATAAGCTCCGTTTTAAAAATAA
LOC_Os11g4   GGAATGCCAGAACGGGCATGTACTTCGTTTTCCAGCGATAAGCTCCGTTTTAAAAATAA
LOC_Os06g0   ---ACCCCTGTTCATGTTACTTCTCACTTTTCACCATGGCAGGCAT-GTTTAGAAAATCA
LOC_Os06g3   ----TACAGCAACATGAAGCTACCTATTTGTCCTAATTGTTTGCTCAATGTGCA--GTAA 6601      6611      6621      6631      6641      6651
LOC_Os02g4   ATTAGCAAGTGATTTATTTGCATTTATAAACAAAAATTTACCACTCGGGTAGTTCATATT
LOC_Os11g4   ATTAGCAAGTGATTTATTTACATTTACAAACAAAAATTTACCACTCGGGTAGTTCACATT
LOC_Os06g0   TT-------TGATTT-T------------ACAGGGCATTACCA-----------------
LOC_Os06g3   AT--------GGGTTATG---------ATGCACAAGCTTACAAGGAGGCTAGCA------

6661      6671      6681      6691      6701      6711
LOC_Os02g4   AAAGTTATTGTCTAGCTTTATTACAAGCAGCATGAAAGTTACGATACCCCAAGGCCTGAG
LOC_Os11g4   AAAATTATTGTCTAGCTTTATTACAAGCAACATGAAAATTTCGATACCCCAAGGCCTGAG
LOC_Os06g0   --------TGTGACCCCTTAATA--ACTAACA--AATAT------------------AT
LOC_Os06g3   ------A--GAATTCCTGATGAAGTACGTACTGAAATAGAGCCATAC-----------T 6721      6731      6741      6751      6761      6771
LOC_Os02g4   TTTGGCAGCACT-TAACTCTGTTGCCCTGTTTTGTCTTGAAAAGTATAACATCACTTAGC
LOC_Os11g4   TTTGGCAGCACTATAACTCTGTTGCCCTGTTTTGTCTTGAAAAGTATAATATCACTTAAC
LOC_Os06g0   TTTGGGTCCACC--AAATCTGTGG---TGGATGGAAAGGGAAATTA-ATAAACAC--AAA
LOC_Os06g3   TTTTTGAGCATGCTTCTATTGTAGA--TGAAGACAACCAGAAACTTCCAAAACTGCCAGA 6781      6791      6801      6811      6821      6831
LOC_Os02g4   AGGACAATGCTCTCCCGAAAACATAACTGATTAGTGGATAGAGGGAG-AGGTTTAG----
LOC_Os11g4   AGGACAATGCTCTCCCGAAAACATAACTGATTAGTGGATAGAGAGAG-TGGTTTAGGTGG
LOC_Os06g0   TGGAAAATTCTTCATTGTGAA---ACGTGATAAG--------GACAA-ATTTTGTG----
LOC_Os06g3   TATTGAAGGTGCTAATGTAGCCAAATATGTCCGGACAGGCCTGACTGTAAGTTTTG----

6841      6851      6861      6871      6881      6891
LOC_Os02g4   ------------------------------------------------------------
LOC_Os11g4   TGTTTGGATCCGGGGACTAAATTTTAGTTCATGTCACATCGGATGTTTGGACACTAATTA
LOC_Os06g0   ------------------------------------------------------------
LOC_Os06g3   ------------------------------------------------------------

6901      6911      6921      6931      6941      6951
LOC_Os02g4   -----------------------------------TCCCAATAGATAATTGACTGGTTACT
LOC_Os11g4   GAAATATTAAACATAGACTAATAATAAAATTTAGTCCCAATAGATAATTGACTGGTTACT
LOC_Os06g0   ------------------------------------------AATAAATAA----------
LOC_Os06g3   ---------------------------------TGGAATTATACAAGATTACAGTT---

6961      6971      6981      6991      7001      7011
LOC_Os02g4   TCATATTCATTGCCCAGAGCTGCCTCATTAAATGTT--CTGTCCTGTGCTTTCTTGGATC
LOC_Os11g4   TCATATTCATTGCCCAGAGCTGCCTCATTAAATGTTGTCTGTTCTGTGCTTTCTTGGATC
LOC_Os06g0   ----AGTAA-------------C---AAAAAATGG---CTAGTATTTGCCTAC-------
LOC_Os06g3   TACAAGTAT-----------------ACAAAATGT---GCATGTTTTTCTTTCAT-----

7021      7031      7041      7051      7061      7071
LOC_Os02g4   TTGAATTAAAAGACGTCTGTACAGGGTACCACACCTCAAGGGATCACAATTCAGAAAGTT
LOC_Os11g4   TTGAATTAAAAGACGTCTGTACAGGGTACCACACCTCAAGGGATCACAATTCAGAAAGTT
LOC_Os06g0   ----ATATAGAGT----------------ACACCTCAAGAGATCA-------GAAAAGT
LOC_Os06g3   -TTTTTACATCTTCTTCTGTCTCATAATGCAGCCACGATGGGCCGACCTTGATATCAATC 7081      7091      7101      7111      7121      7131
LOC_Os02g4   TCCCT-TTATTGGGCTGCAGTAAAT-GATTCCATCGTGTAGAAAAGAACAAAAGCAATTA
LOC_Os11g4   TCCCT-TTATTGGTCTGCAGTAAAT-GATTCCATCGTATAGAAAAGAACAAAAGCAATTA
LOC_Os06g0   TGCCT-TTATTG--ATGGAGTAATT-GAATTAGTAGT-------A-------AGCAATAA
LOC_Os06g3   AGCATGTTAATAACGTTAAATACATAGGGTGGATCCTAGAGGTAAAAAAAGTTCCCCT--

7141      7151      7161      7171      7181      7191
LOC_Os02g4   ATGCTGTGCCATATCATGGGAGAAGCTAAGGACCGATCTAGAACAGTGAACTTTTGTTG-
LOC_Os11g4   ATGCTGTGCCATATCATGGGAGAAGCTAAGGACCCATCTAGAACAGTGAACTTTTGTTG-
LOC_Os06g0   ATTCTGTGG-ACCT-AGGGGACATCC------CTGATCTAGATC----GAGTTTTGAT--
LOC_Os06g3   ATTATGTTCATCTTTATTGCCCTTGCTAA---CACCTCTTGCCTAGATGATTCTTGAGGG
```

Figure 4h

```
              7201       7211       7221       7231       7241       7251
LOC_Os02g4    AACAGCATCTGTCAGTTTAAATTTCTAGGTGGTCATCATTCATCAAATAAGTGGTGCTAG
LOC_Os11g4    AACAGCATCTGTCAGTTTAAAAATCTAGGTGGTCATCATTCATCAAATAAGTGGTGCTAG
LOC_Os06g0    ---CTCATGCTACA-TTTAATCTTCCATGTCAGCAACTTTCA-----------GTAC---
LOC_Os06g3    AAAAAAATGCTTC--T-TGAAGTTCAGTATGTT--ACTTTCAGAAAAAAT---ATCCATT 7261       7271       7281       7291       7301       7311
LOC_Os02g4    TACTACTATT-CACACGTTATGTTTAAATCCTCTTGTCAACTGTGTCAACAAGTGGTTGA
LOC_Os11g4    TGCTACTATTGCACACGTTATGTTTAAATCCTCTTGTCAACTGTGTCAACAAGTGGTTGA
LOC_Os06g0    --CTGCTATT---------AAATT----TCCCCTGTTCTTCTG-----ACGATTGATGCA
LOC_Os06g3    TGTTTTTATT---------TACTGTAAACACTCCATGGAGTTGCTGTTAGGCATCTTTGT 7321       7331       7341       7351       7361       7371
LOC_Os02g4    AAACTTCTTTTTTGGGGTTTTGAGTTAGAAAAATGGAAGTGCAATTTCAAACTGTTTTTT
LOC_Os11g4    AAACTTCTTTTTTGGGGGTTTTGAGTTATAAAAATGGAGGTGCAATTTCAAATTGTTTTTT
LOC_Os06g0    --A-----TTT-TAAGTTTATGAGA-AGGAAAACGGTCTGCTGTTTTTGAATTCTGAATG
LOC_Os06g3    CGC-----GGTATTCATTATTAAGT-TGTCACATGGTGGAGCA-T----AACTTTGTGT- 7381       7391       7401       7411       7421       7431
LOC_Os02g4    TAGTTCAGATACAATTGCCGATGTCTTTCTGTGGATCAAAAAGAATGACAGATGTATTGT
LOC_Os11g4    TAGTTCAGATACAATTGCCGACGTCTTTCTGTGGATCAAAAA-AATGACAGATGTATTGT
LOC_Os06g0    TAGTTTACA--CAATT---------TCTCATAGGCTGAAAT----T--T-----TG--GT
LOC_Os06g3    TGCTTTACTTGCCTTT-----T---TCTCTTTGGGCATACA--------------TTTAGT 7441       7451       7461       7471       7481       7491
LOC_Os02g4    ACCAACCTGCTATGGTTTTAGGGGAGATATGGTTCAAGTTGACACATGGGTCGCTGCTGC
LOC_Os11g4    ACCAACCTGCTATGGTTTTAGGGGAGATACGGTTCAAGTTGACACATGGGTTGCTGCTGC
LOC_Os06g0    TGCAA------AT--TTTTAGGGGAGATATGGTCCAAGTTGACACATGGGTAGCTGCTGC
LOC_Os06g3    ACTA-----------TTGATGGTGCTACATAATTCAAAGAGATTCATTTATCTCGCTATA 7501       7511       7521       7531       7541       7551
LOC_Os02g4    TGGCAAAAATGGCATGCGTCGAGACTGGCATGTTCGTGACTACAACTCTGGCCGAACAAT
LOC_Os11g4    TGGCAAAAATGGCATGCGTCGAGACTGGCATGTTCGTGACTACAACTCTGGCCGAACAAT
LOC_Os06g0    TGGCAAAAATGGCATGCGTCGAGATTGGCATGTTCGGGACTACAACTCTGGTCAAACAAT
LOC_Os06g3    TTTCCCATATGTTATGTTCCAAGAA-------TTTGGGAATA-AACAGT--------AAT 7561       7571       7581       7591       7601       7611
LOC_Os02g4    CTTGAGAGCTACAAGGTTTGGGCTTCAACTGTATTCTATTGCAAGAATCATCTGTATCAT
LOC_Os11g4    CTTGAGAGCTACAAGGTTTGGGCTTCAACTTATTCTATTGCAAGAATCATCTGTATCGT
LOC_Os06g0    CTTGAGGGCTACAAGGTTTGTGTTTA-----T---CGTTTGCA-------TTTGTTGCAT
LOC_Os06g3    CAGAAGAG-TACTGGATTTGTAGGTA--CTTTAT-TTTTTGTG-------TGTGTGT-GT 7621       7631       7641       7651       7661       7671
LOC_Os02g4    TTTTTTTGTGAGGACATCCAATCTTGGTATTTCTGCTTGGTCACATCATTGATAATCACT
LOC_Os11g4    TTTTTTTATGAGGATATCCAATCTTGGTATTTCTGCTTGATCACATCATTGATAATTGCT
LOC_Os06g0    TTCTTTTGT------TTC--ATGCTG-TTTACCAGCATGTTTTATTCCTTTTCGATTGCT
LOC_Os06g3    GGGGGGGGGGGGGGGCTCAGATCATG-CCTATGATTAGGCATTACTGTAGGAGTTTAGAT 7681       7691       7701       7711       7721       7731
LOC_Os02g4    AATTGTGCTCCTTTTCCAATCCATTTGTTGCAGTGTTTGGGTGATGATGCACAAGAAAAC
LOC_Os11g4    AATTGTGCTCCTTTTCCAATCC-TTTCTTGCAGTGTTTGGGTGATGATGCACAAGAAAAC
LOC_Os06g0    AATTGT--TCCTCT-------C-TTGTTTGCAGTGTTTGGGTGATGATGAATAAGAACAC
LOC_Os06g3    AAACTTGGTCAAGG-----------TCCCAAAAGGGTGTGCCTATGGTTCTACAAGTGTCC 7741       7751       7761       7771       7781       7791
LOC_Os02g4    TAGAAGACTTTCAAAAATGCCAGATGAAGTTAGAGCTGAAATAGGCCCATATTTCAATGA
LOC_Os11g4    TAGAAGACTTTCAAAAATGCCAGATGAAGTTAGAGCTGAAATAGGCCCATATTTCAATGA
LOC_Os06g0    TAGAAGACTTTCAAAAATGCCAGATGAAGTTAGAGCTGAAATAGGCCCGTATTTCAATGG
LOC_Os06g3    -ACCTAACTTT--A---TCCTCAAGCACGCAACCACTTATCTGGCAGCTTTGTACTCTTT 7801       7811       7821       7831       7841       7851
LOC_Os02g4    CCGTTCAGCTATAACAGAGG-AGCAGAGTGAAAAGTTAGCCTAGACAGGAAATAAAGTTG
LOC_Os11g4    CCGTTCAGCTATAACAGAGG-AGCAGAGTGAAAAGTTAGCCAAGACAGGAAATAAAGTTG
LOC_Os06g0    CCGTTCTGCTATATCAGAGG-AGCAGGGTGAAAAGTTGCCTAAGCCAGGGACCACATTTG
LOC_Os06g3    CA----AGCTATACGAAAAATATCTGTTGCACTAGTTGGAGAAGTAATG---TATCCTAG
```

Figure 4i

```
             7861       7871       7881       7891       7901       7911
LOC_Os02g4   GTGATGATGCTACAGAGCAATTCATAAGAAAGGGGCTCAC--TGTAAGTCAGCTAGACAT
LOC_Os11g4   GTGATGATGCTACAGAGCAATTCATAAGAAAGGGGCTCAC--TGTAAGTCAGCTAGACAT
LOC_Os06g0   ATGGCGCTGCTACCAAACAATTCACAAGAAAGGGCTTAC--TGTAAGTCAGTTA-ATAT
LOC_Os06g3   CAGATTTTACTACATTAGGTTGGTCACCTACGTACCTAACCCTGTACGCTTGTTG-CTTC 7921       7931       7941       7951       7961       7971
LOC_Os02g4   GGTTACATACTGAATTATCATTATGCCTCAACTGCTATCATTTATCTAAGAAAAACAGTA
LOC_Os11g4   AGTTACATACTAAATTATCATTATGCCTCAACTGCAATCATTTATCTAAGAAAAATAGTA
LOC_Os06g0   TGCTTGTTACCG-----TCATT---------------CATTTGCTGG-----------
LOC_Os06g3   CGATAAAGAGCTTGGCTGGAATA---CTTATATG----CAATTTGATCACAAG-------

7981       7991       8001       8011       8021       8031
LOC_Os02g4   ATAATTGATCTCACCCCTCATTTATTTTAAATGATATTTGATGGACTCTTGTTTACTGCA
LOC_Os11g4   ATATTTGATCTCACCCCTCATTTATTTTAAATGATCTTTGATGGACTCTTGTTTACTGCA
LOC_Os06g0   ----TGGTTCTCATGCATAAAATTTCTCA---------TGAGGGATCCTTTGTTCATGT-
LOC_Os06g3   ----TCATTCACTTAATTCAATTTTTTTTAGAG-----TGATCAACACCTGCATATAAT- 8041       8051       8061       8071       8081       8091
LOC_Os02g4   ACAGCCTAGATGGGGTGACCTCGATGTCAATCAGCA-TGTGAACAATGTTAAATATATTG
LOC_Os11g4   ACAGCCTAGATGGGGTGACCTCGATGTCAATCAGCA-TGTGAACAATGTTAAATATATTG
LOC_Os06g0   -CAGCCGAAGTGGAGTGACCTTGATGTCAACCAGCA-TGTGAACAATGTGAAGTATATTG
LOC_Os06g3   ---GCATATTTG------CCTGGTTGACAATCTGCCGTGTGTA---TGTG---TGTTTTG 8101       8111       8121       8131       8141       8151
LOC_Os02g4   GGTGGATCCTTGAGGTGGTTATTCTTGTCCCTTATATTCATTGTTTAGAGAA--AAATAA
LOC_Os11g4   GGTGGATCCTTGAGGTGGTTATTCTTGTCCCTTTTATTCATTGTTTAGAGAA--AAATAA
LOC_Os06g0   GTTGGATACTTGAGGTAAC--TTCTTTTTCCTT-------TTCTCTATCCGA--ACATGC
LOC_Os06g3   GAAGAAGGGGAGGGGTAGT----CATGTATGTAT------TTATCCAGTGGACCACATAA 8161       8171       8181       8191       8201       8211
LOC_Os02g4   TTTGGCTTTATCCTTTTATATGGTACTTCCTTTGTTTCACAATGTAAGTCATTTTAGCAT
LOC_Os11g4   TTTGGCTTTATCCTTTTATATGGTG-----------------------------------
LOC_Os06g0   TATCTCTAGATCAGAAAAGAGAGTG-----------------------------------
LOC_Os06g3   TGAGGAAAAAGAAATTGTTCAGGTG-----------------------------------

8221       8231       8241       8251       8261       8271
LOC_Os02g4   TTCCCATATTTATATTTATGCTAATGAATCTAAATAGATATATGTGTCTAGATTCATTGG
LOC_Os11g4   ------------------------------------------------------------
LOC_Os06g0   ------------------------------------------------------------
LOC_Os06g3   -------------------------------------------ACCTG---------

8281       8291       8301       8311       8321       8331
LOC_Os02g4   CATCAATATGAATGTGAGAAATGCTAAAATGACTTACATTATGAAACGGAGGGAGTAGTT
LOC_Os11g4   ------------------------------------------------G-----TT
LOC_Os06g0   ------------------------------------------------------------
LOC_Os06g3   ---CAACCT---------AGA-----------------------------------TG 8341       8351       8361       8371       8381       8391
LOC_Os02g4   GTTAGGGAACCATTTTATGTAGTACTTGCAATTATTTTCTAGAGATTCTGATCTGACCAT
LOC_Os11g4   GTTAGGGAACCATTTTATGTAGTACTTGCAATTATTTTCTAGAGATTCTGATCTGACCAT
LOC_Os06g0   -------TCTGATCGTAATTAGTA-----ACCTAGTTCCTAG------TCATATGCCAAG
LOC_Os06g3   GGCCCAAAACAACCCAAAATATTAGG-GAAATTAACACTTCAGG-----CATTTCCTAAC 8401       8411       8421       8431       8441       8451
LOC_Os02g4   CTGTATTGTTGATATTGTCATTAGTCTTACATCTGGTCAGTCAGAAGGCTTTCAAACATG
LOC_Os11g4   CTGTATTGTTGATATTGTCATTAGTCTTACATCTGGTCAGTCAGAAGGCTTTCAAACATG
LOC_Os06g0   CTGTA------------AAA-ACACTTGCA-CTGTATATTCAAAAGCTATTCAAA----
LOC_Os06g3   ATACA-----------GAAATATTTATTAC--CAACATGCGCACATGTTGCTTAAC----

8461       8471       8481       8491       8501       8511
LOC_Os02g4   TTTCTGAGTTCTTTCTAATTTTTTCCCC-CAGAGTGCTCCAATTTCAGTACTGGAGAAGC
LOC_Os11g4   TTTTTGAGTTCTTTCTAATTTTTTCCCC-CAGAGTGCTCCAATTTCAGTACTGGAGAAGC
LOC_Os06g0   TTTCTGAGTACGTTTTGTTTTTTTTCCTCAGAGTGCTCCAATTTCGATACTGGAGAAGC
LOC_Os06g3   ---CCTACCTTTTTGTCCTTTTTTCCCCTCAGAGCGCACCAATCTCCATTCTGGAGAAAC
```

Figure 4j

```
                8521      8531      8541      8551      8561      8571
LOC_Os02g4      ATGAGCTTGCAAGCATGACCCTGGATTACAGGAAGGAGTGTGGCCGAGACAGCGTGCTGC
LOC_Os11g4      ATGAGCTTGCAAGCATGACCCTGGATTACAGGAAGGAGTGTGGTCGAGACAGCGTGCTGC
LOC_Os06g0      ACGAGCTTGCAAGCATGACCTTGGATTACAGGAAGGAGTGTGGCCGTGACAGTGTGCTTC
LOC_Os06g3      ATGAGCTGGCAAGTATTGTCCTGGATTACAAGAGGGAGTGTGGCCGAGACAGCGTGCTGC 8581      8591      8601      8611      8621      8631
LOC_Os02g4      AATCACTTACCACCGTGTCAGGGGAATGCACCAGCATTGGCGCCGACAAGCAGGCTTCTG
LOC_Os11g4      AATCACTTACCACCGTGTCAGGGGAATGCACCAGCATTGGCGCCGACAAGCAGGCTTCTG
LOC_Os06g0      AGTCGCTTACCGCTGTTTCAGGTGAATGCGA------TGATGGCAACA--CAGAATCCT-
LOC_Os06g3      AATCACACACTACCGTGTACACTGACTGCAACA----AGCACTCTGGA--CAAACCACT- 8641      8651      8661      8671      8681      8691
LOC_Os02g4      CCATCCAGTGCGACCATCTTGTGAAG-----------GCTGACATTGTGAAGGCACACA
LOC_Os11g4      CCATCCAGTGCGACCATCTTCTTCAGCTTGAGTCAGGAGCTGATATTGTGAAGGCACACA
LOC_Os06g0      CCATCCAGTGTGACCATCTGCTTCAGCTGGAGTCCGGAGCAGACATTGTGAAGGCTCACA
LOC_Os06g3      --TTGCACTGTGAGCATTTGCTGAGCCTGGAATCAGGACCTACCATCGTCAAGGCCAGGA 8701      8711      8721      8731      8741      8751
LOC_Os02g4      CAGAGTGGCGACCAAAAGCGATCGCATGCAGCAGCTGAGAACGCG-----TAAACAAACAA
LOC_Os11g4      CAGAGTGGCGACCAAAAGCGATCGCACGCAGCAGCTGAGAACGCG-----TAAACAAACAA
LOC_Os06g0      CAGAGTGGCGACCGAAGCGAGCTCAGGGCG-AGGGGAACATGGCT--TTTTCCCAGCTG
LOC_Os06g3      CCATGTGGAGGCCAAAAGGAAC-CAGGCCCCAAGAGAGTATCATTCCGTCTTCGTCGTGA 8761      8771      8781      8791      8801      8811
LOC_Os02g4      ACCGACGAAAATCTGTGGTAGGGAGAATATCAAACTTCCCTTGCCTCTGTTGCCCCTGAAG
LOC_Os11g4      ACCGACGAAAATCTGTGGGAGGGAGAATATCAAACTTCCCTTGCCTCTGTTGCCCCTGAAG
LOC_Os06g0      AGAGTGCATGAGCGCT--TCTGTAGTTTATCCGGCAAG--TAACCTCT-TTGA---GAAG
LOC_Os06g3      AGCGCGTAAAATCTTTCATGTGTTGATTTT---GGTAGCAACAACTTGGTTAAAC-CAAG 8821      8831      8841      8851      8861      8871
LOC_Os02g4      CTGATCTTGA-AGTGTGAGTTGTATTCTGTAAAAAATTAGTAGTTTCCATAGTGTGAGGT
LOC_Os11g4      CTTATCTTGA-AGTGTGAGTTGTATTCTGTAAAAAATTAGTAGTTTCCATAGTGTGAGGT
LOC_Os06g0      TGCAGATTCT-AACTTGGCTAGCAACACAGGACAAATGATTGTTGGTGGGAAATTTGGCA
LOC_Os06g3      GACAAGTGGACAACAACTTGTGTTCTCTATGGAAAGGCAAAACCTGGATGAACATAACGA 8881      8891      8901      8911      8921      8931
LOC_Os02g4      TGGAGGGGAGGTGTTGGTGCTTGCCTACTGTACCTGCT-ACATCT-ATTATTTCTTGATT
LOC_Os11g4      TGGAGGGGAGGTGTTGGTGCTTGCCTACTGTACCTGCT-ACATCT-ATTATTTCTTGATT
LOC_Os06g0      TGCCGAGCCTGGGTTTTGTGATGCACACAGCACACATTCAGATTTGAAGATTGAGAGATG
LOC_Os06g3      CGGGGACGTAAGTTATTTACAGACAAAATGTATGGATT-----TGGAGGAGTTCAAAAGA 8941      8951      8961      8971      8981      8991
LOC_Os02g4      CTTTGTTCGCTTTTTTTTTCTTTTTGTTTTTAACCCCTGTGGAGATAAGA-CAGGT--
LOC_Os11g4      CTTTGTTCGCTTTTTTTTTCTTTTTGTTTTTAACCCCTGTGGAGATAAGA-CAGGT--
LOC_Os06g0      CTTCTTATTGGCAGCTTGTTCAGAAAGATGACTAAGCGGTTTGG-GATAAAATCAGCTGA
LOC_Os06g3      GG--GGGGGGGGGGGGGGCAAGATGGAGGTAAAA-----TGCAGAAAAGA-CAGAAGG 9001      9011      9021      9031      9041      9051
LOC_Os02g4      TTTGAAGTGTGGAAGAGGTTGTTTCAATCGTCTAATTGATTCAACTATTCAGCAAGTAAA
LOC_Os11g4      TTTGAAGTGTGGAAGAGGTTGTTTCAATCGTCTAATTGATTCAACTATTCAGCAAGTAAA
LOC_Os06g0      TTGGGAAACATTAGCAGGATGATAAGCATGACTGGTGGTACCAATGAAAAGGGTTGAAAT
LOC_Os06g3      CGTATTGTGCATGATTTGTTGTTTCAGCTTTTCCTTCTATTTTTCCTTTCCTTAGCAAAG 9061      9071      9081      9091      9101      9111
LOC_Os02g4      CTGCTCCATGGAA-ATTT-------------------------------
LOC_Os11g4      CTGCTCCATGGAA-TTTCATCGTTTGGTTGGAGCCTGAG-----------
LOC_Os06g0      CCTTTGCATTGTTCATTTGTTGTGGAGCAAGAGTGGCCGCAGTTGCTTATCACACAGGAT
LOC_Os06g3      ATATTCAATTACACAGATGG-GTGTTGTAAGTATTGAAATTGTAGCTACTGCTGTACAAT 9121      9131      9141      9151      9161      9171
LOC_Os02g4      ------------------------------------------------
LOC_Os11g4      ------------------------------------------------
LOC_Os06g0      GATG-GAGGTGTTTGTGTGAAGCTTATTGCTGAAGCTGGATTGTTTTTGACCTGTGTTTC
LOC_Os06g3      GGGAAGTGAAATGCTTCTCATGCATGTTTCTGTCTGGGCTATGTCTATATTATGAGCCCT
```

Figure 4k

```
              9181      9191      9201      9211      9221      9231
LOC_Os02g4    ------------------------------------------------------------
LOC_Os11g4    ------------------------------------------------------------
LOC_Os06g0    TAAAAGAAAAGGGAAAAGAAGAAGCTGTGGATTGAGGCCGGAGCAGCAGAGATATTACAA
LOC_Os06g3    CGAAAGCAGATTGCCTGGTCCGAATTGTTTGAAATTTTAAGTTT----------------

9241      9251      9261      9271      9281      9291
LOC_Os02g4    ------------------------------------------------------------
LOC_Os11g4    ------------------------------------------------------------
LOC_Os06g0    TCGACATAGATAAATAAGATGTAATACTAATTTAGCCCAGGTGGTTTGTGTGTGGAGATG
LOC_Os06g3    ------------------------------------------------------------

9301      9311      9321      9331      9341      9351
LOC_Os02g4    ------------------------------------------------------------
LOC_Os11g4    ------------------------------------------------------------
LOC_Os06g0    CAATCCATTGTAGTAACAGCCTAACTTGTACATTCTTGCCATCTTTTTCTTATTAATTGA
LOC_Os06g3    ------------------------------------------------------------

9361      9371      9381      9391      9401      9411
LOC_Os02g4    ------------------------------------------------------------
LOC_Os11g4    ------------------------------------------------------------
LOC_Os06g0    ATGAATGAATCGCAGACCTCCTGCGTTTTCATCAATAATTGAAATGACTTCTGCTTCATC
LOC_Os06g3    ------------------------------------------------------------

9421      9431      9441
LOC_Os02g4    -------------------------
LOC_Os11g4    -------------------------
LOC_Os06g0    AAGAATTGAATGAATTGTCTGTCTG
LOC_Os06g3    -------------------------
```

Figure 4l

```
   1 ..ATGGCTGGTTCTCTTGCGGCGTCTGCATTCTTCCCTGTCCCAGGGTCT 48
      ||||||||||||||||||||||||||||||||||||||||||||||||
1151 TCATGGCTGGTTCTCTTGCGGCGTCTGCATTCTTCCCTGTCCCAGGGTCT 1200

49 TCCCCTGCAGCTTCGGCTAGAAGCTCTAAGAACACAACCGGTGAATTGCC 98
     ||||||||||||||||||||||||||||||||||||||||||||||||||
1201 TCCCCTGCAGCTTCGGCTAGAAGCTCTAAGAACACAACCGGTGAATTGCC 1250

99 AGAGAATTTGAGTGTCCGCGGAATCGTCGCGAAGCCTAATCCGTCTCCAG 148
     ||||||||||||||||||||||||||||||||||||||||||||||||||
1251 AGAGAATTTGAGTGTCCGCGGAATCGTCGCGAAGCCTAATCCGTCTCCAG 1300

149 GGGCCATGCAAGTCAAGGCGCAGGCGCAAGCCCTTCCTAAGGTTAATGGA 198
     ||||||||||||||||||||||||||||||||||||||||||||||||||
1301 GGGCCATGCAAGTCAAGGCGCAGGCGCAAGCCCTTCCTAAGGTTAATGGA 1350

199 ACCAAGGTTAACCTGAAGACTACAAGCCCAGACAAGGAGGATATAATACC 248
     ||||||||||||||||||||||||||||||||||||||||||||||||||
1351 ACCAAGGTTAACCTGAAGACTACAAGCCCAGACAAGGAGGATATAATACC 1400

249 GTACACTGCTCCGAAGACATTCTATAACCAATTGCCAGACTGGAGCATGC 298
     ||||||||||||||||||||||||||||||||||||||||||||||||||
1401 GTACACTGCTCCGAAGACATTCTATAACCAATTGCCAGACTGGAGCATGC 1450

299 TTCTTGCAGCTGTCACGACCATTTTCCTGGCAGCTGAGAAGCAGTGGACT 348
     ||||||||||||||||||||||||||||||||||||||||||||||||||
1451 TTCTTGCAGCTGTCACGACCATTTTCCTGGCAGCTGAGAAGCAGTGGACT 1500

349 CTGCTTGACTGGAAGCCGAAGAAGCCTGACATGCTGGCTGACACATTCGG 398
     ||||||||||||||||||||||||||||||||||||||||||||||||||
1501 CTGCTTGACTGGAAGCCGAAGAAGCCTGACATGCTGGCTGACACATTCGG 1550

399 CTTTGGTAGGATCATCCAAGACGGGCTGGTGTTTAGGCAAAACTTCTTGA 448
     ||||||||||||||||||||||||||||||||||||||||||||||||||
1551 CTTTGGTAGGATCATCCAAGACGGGCTGGTGTTTAGGCAAAACTTCTTGA 1600

449 TTCGGTCCTACGAGATTGGTGCTGATCGTACAGCTTCTATTGAGACATTA 498
     ||||||||||||||||||||||||||||||||||||||||||||||||||
1601 TTCGGTCCTACGAGATTGGTGCTGATCGTACAGCTTCTATTGAGACATTA 1650

499 ATGAATCATTTA.................................... 510
     ||||||||||||
1651 ATGAATCATTTACAGGTGATACAATGGAGCTATGCTGCTTTAGCTTTTCT 1700
```

Figure 5a

```
 511 ...........CAGGAAACAGCTCTGAACCATGTGAAAACTGCTGGTCT 548
             ||||||||||||||||||||||||||||||||||||||
1751 TTTGAAGCTTTGCAGGAAACAGCTCTGAACCATGTGAAAACTGCTGGTCT 1800

549 CTTAGGTGATGGTTTTGGTGCTACGCCGGAGATGAGCAAACGGAACTTAA 598
     ||||||||||||||||||||||||||||||||||||||||||||||||||
1801 CTTAGGTGATGGTTTTGGTGCTACGCCGGAGATGAGCAAACGGAACTTAA 1850

599 TATGGGTTGTCAGCAAAATTCAGCTTCTTGTTGAGCGATACCCATCAT.. 646
     |||||||||||||||||||||||||||||||||||||||||||||||
1851 TATGGGTTGTCAGCAAAATTCAGCTTCTTGTTGAGCGATACCCATCATGG 1900
                           .
                           .
                           .
 647 ................................GGGGAGATATGGT 659
                                     |||||||||||||
3101 ATTTCTCATAGGCTGAAATTTTGGTTGCAAATTTTAGGGGAGATATGGT 3150

660 CCAAGTTGACACATGGGTAGCTGCTGCTGGCAAAAATGGCATGCGTCGAG 709
     ||||||||||||||||||||||||||||||||||||||||||||||||||
3151 CCAAGTTGACACATGGGTAGCTGCTGCTGGCAAAAATGGCATGCGTCGAG 3200

710 ATTGGCATGTTCGGGACTACAACTCTGGTCAAACAATCTTGAGGGCTACA 759
     ||||||||||||||||||||||||||||||||||||||||||||||||||
3201 ATTGGCATGTTCGGGACTACAACTCTGGTCAAACAATCTTGAGGGCTACA 3250
                           .
                           .
                           .
 760 ....AGTGTTTGGGTGATGATGAATAAGAACACTAGAAGACTTTCAAAAA 805
         ||||||||||||||||||||||||||||||||||||||||||||||
3351 TTGCAGTGTTTGGGTGATGATGAATAAGAACACTAGAAGACTTTCAAAAA 3400

806 TGCCAGATGAAGTTAGAGCTGAAATAGGCCCGTATTTCAATGGCCGTTCT 855
     ||||||||||||||||||||||||||||||||||||||||||||||||||
3401 TGCCAGATGAAGTTAGAGCTGAAATAGGCCCGTATTTCAATGGCCGTTCT 3450

856 GCTATATCAGAGGAGCAGGGTGAAAAGTTGCCTAAGCCAGGGACCACATT 905
     ||||||||||||||||||||||||||||||||||||||||||||||||||
3451 GCTATATCAGAGGAGCAGGGTGAAAAGTTGCCTAAGCCAGGGACCACATT 3500

906 TGATGGCGCTGCTACCAAACAATTCACAAGAAAAGGGCTTACT....... 948
     |||||||||||||||||||||||||||||||||||||||||||
3501 TGATGGCGCTGCTACCAAACAATTCACAAGAAAAGGGCTTACTGTAAGTC 3550
                           .
                           .
```

Figure 5b

```
 949 ..........................CCGAAGTGGAGTGA  962
                              ||||||||||||||
3601 TAAAATTTCTCATGAGGGATCCTTTGTTCATGTCAGCCGAAGTGGAGTGA 3650

963 CCTTGATGTCAACCAGCATGTGAACAATGTGAAGTATATTGGTTGGATAC 1012
     |||||||||||||||||||||||||||||||||||||||||||||||||
3651 CCTTGATGTCAACCAGCATGTGAACAATGTGAAGTATATTGGTTGGATAC 3700

1013 TTG............................................. 1015
     |||
3701 TTGAGGTAACTTCTTTTTCCTTTTCTCTATCCGAACATGCTATCTCTAGA 3750
                             .
                             .
                             .

1016 ........................AGAGTGCTCCAATTTCGATACT 1037
                             |||||||||||||||||||||||
3851 TCTGAGTACGTTTTGTTTTTTTTCCTCAGAGTGCTCCAATTTCGATACT 3900

1038 GGAGAAGCACGAGCTTGCAAGCATGACCTTGGATTACAGGAAGGAGTGTG 1087
     |||||||||||||||||||||||||||||||||||||||||||||||||
3901 GGAGAAGCACGAGCTTGCAAGCATGACCTTGGATTACAGGAAGGAGTGTG 3950

1088 GCCGTGACAGTGTGCTTCAGTCGCTTACCGCTGTTTCAGGTGAATGCGAT 1137
     |||||||||||||||||||||||||||||||||||||||||||||||||
3951 GCCGTGACAGTGTGCTTCAGTCGCTTACCGCTGTTTCAGGTGAATGCGAT 4000

1138 GATGGCAACACAGAATCCTCCATCCAGTGTGACCATCTGCTTCAGCTGGA 1187
     |||||||||||||||||||||||||||||||||||||||||||||||||
4001 GATGGCAACACAGAATCCTCCATCCAGTGTGACCATCTGCTTCAGCTGGA 4050

1188 GTCCGGAGCAGACATTGTGAAGGCTCACACAGAGTGGCGACCGAAGCGAG 1237
     |||||||||||||||||||||||||||||||||||||||||||||||||
4051 GTCCGGAGCAGACATTGTGAAGGCTCACACAGAGTGGCGACCGAAGCGAG 4100

1238 CTCAGGGCGAGGGGAACATGGGCTTTTTCCCAGCTGAGAGTGCATGA... 1284
     |||||||||||||||||||||||||||||||||||||||||||||||
4101 CTCAGGGCGAGGGGAACATGGGCTTTTTCCCAGCTGAGAGTGCATGAGCG 4150
                             .
                             .
                             .
```

```
proteinF_1    MGAGGRMTEKEREEQQKLLGRAGNGAAVQRSPTDKPPFTLGQIKKAIPPHCFQRSVIKSF
proteinF_3    ------------------------------MQRSPVDKPPFTLGDIKKAIPPHCFHRSVIKSF
proteinF_2    MGTSSRPTTVKEGKKLEAPRRAGSHAAVKRSPVDKPPFTLGDIRKAIPPHCFHRSVIKSF
proteinF_4    ------------------MAGGRRWGGWREQEPPRRAGSSAAVQRFHRSVIKSF 61           71          81          91         101         111
proteinF_1    SYVVHDLVIVAALLYEFALVMIPVLPSGMEFAAWPLYWIAQGCVLTGVWVIAHECGHHAFS
proteinF_3    SYLLHDLAIAAGLLYFALVGIPALPSILRLVAWPLYWIAAQGSVLTGVWVIGHECGHHAFS
proteinF_2    SYLLHDLAIAAGLLYFALVVIPALPGVLRLVAWPFYWAAQGCFLFGVWIIAHECGHHAFS
proteinF_4    SYLLRDVAIAAGLLNEFALVGIPVLPAGVLRPPRRLAVLLGRAGLLPVRGVDHRARVRAPR 121         131         141         151         161         171
proteinF_1    DYSVLDDIVGLVLHSSLLVPYEFSWKYSHRRHHSNTGSLERDEVFVPKQKSAMAWYTPYVY
proteinF_3    DYLLDNLVGLVLHSALLTPFFSWKYSHRRHHANTGSMEKDEVYVAKKKSALPWYTPYVE
proteinF_2    GHALLDDTLGLVLHSWLLAPYFSWKYTHQRHHSNTSSQERDEVFVPRFKSDLPWYSPYVY
proteinF_4    APRRHPRSGPALVASGTILLVEIQPPAAPLQHQLTGARRGVRPQVQVRSAVELPVRVQVQ 181         191         201         211         221         231
proteinF_1    H--NPIGRLVHIFVQLTLGWPLYLAENVSGRPYPREFA-CHFDPYGPIYNDRERVQIFISD
proteinF_3    G--NPVGRLVYIALQLTLAWPLYLAFNLSGQPYPRLVTCHYDPYSPLFSDQERVQLVSD
proteinF_2    KYNNPVARLLLLVVQLTVGWPMYLVFNTWGRQYPREFA-SHFDPSGPIYKGRERVFIAISD
proteinF_4    Q--RPVARLLLLGMQLTVGWPMYLVFNTWGRWYPREFA-SHFDPSGAIYMRERVFIAISD
```

Figure 7a

```
           241        251        261        271        281        291
proteinF_1 VGVVSAGLALFKLSSAEGFWWVVRVYGVPLLIVNAWLVLITYLQHTHPALPHYDSSEWDW
proteinF_3 AAILAVLLALHRLTAAYGLWWVVRVYGVPVMIVGALFVLITYLHHTHRALPHYDSSEWEW
proteinF_2 IGMLAVSLALYRLAEGYGFWWVVRVYGVPLLVVNAWLVVTYLHHTHRAIPHYDSSEWDW
proteinF_4 IGMLAVSLAL--------------------------------------------------

301        311        321        331        341        351
proteinF_1 LRGALATVDRDYGILNKVFHNITDTHVAHHLFSTMPHYHAMEATKAIRPILGEYYQFDPT
proteinF_3 LRGSLATVDRDYGVLNRVLHNVTDTHVLHHLFPSMPHYHAMEATRAARPVLGEYYKFDRT
proteinF_2 LRGALATVDRDYSFLNRVFHNITDTHVVHHLFPTIPHYHAVEATKAIRPILGEYYQFDPT
proteinF_4 ------------------------------------------------------------

361        371        381
proteinF_1 PVAKATWREAKECIYVEPEDNKGVFWYNNKE
proteinF_3 PIIEATWREAKECMYVEPRERDGIYWYNNKE
proteinF_2 PIVKAIWREAKECIYIQSEDHKGVFWYSNKE
proteinF_4 -------------------------------
```

```
cdsFAD20_2        ATGGGTACCAGCAGCCGGCCGACGACGTGAAGGAGGGAAGAAACTAGAGGCGCCCCGC
cdsFAD20_4        ------------------------------------------------------------
cdsFAD20_1        ATGGGTGCCGGCGGCGGCAGAGATGACGGAGAAGGAGGCGGGAGGAGCAGCAGAAGCTGCTCGGC
cdsFAD20_3        ------------------------------------------------------------

61         71         81         91        101        111
cdsFAD20_2        CGTGCCCGGCGGCAGCCATGCAGCCGTCGAAGCGCTCTCCGGTGACA--AGCCGCCGTTCACGC
cdsFAD20_4        ---ATGGGGGCGGACGGCCGTGGTGGGGCGAGCGGGCGATGGCG-TGAACAGGAGCCGCC--TCGCCG
cdsFAD20_1        CGCGCCGGCAATGCCGCGGCCGTCAGCGCGGTCGCCGACGACA--AGCCGCCGTTCACGC
cdsFAD20_3        ------------ATGCAGCGCCTCACCGGTGACA--AACCGCCGTTCACGC 121        131        141        151        161        171
cdsFAD20_2        TGGGCCGACATCAGAAAGGCCATCCACCGCACTGCTTCCACCGCTCCGTCGATCAAGTCAT
cdsFAD20_4        TGC-CGGCAGTGCAGCCGT------GCAGCGCTTCCACCGCTCCGTCGATCAAGTCAT
cdsFAD20_1        TGGGGCAGATCAAGAAGGCCATCCCGCCTCACTGCTTCCAGCGCTCGTCGATCAAGTCCT
cdsFAD20_3        TGGGGGACATAAAGAAGGCCATCCACCGCACTGCTTCCACCGCTCCGTCGATCAAGTCAT 181        191        201        211        221        231
cdsFAD20_2        TCTCCTACCTGCTCCACGACCTTGCCATTGCCGGGGCCTCCTCCTACTTTGCTCTGGTCG
cdsFAD20_4        TCTCCTACCTGCTCCGTGACCTTGACGATGACCTCGTAGCCATTGCCGGGCCTCCTCCTCAACTTTGCGCTGGTCG
cdsFAD20_1        TCTCCTACGTGCTCCATGACCTCGTAGCGCCGCTGGATCGCCGCGTCGCTCTACTTCGCGCTGGTCA
cdsFAD20_3        TCTCCTACCTGCTCCACGACCTTGCCATCGCCGCCCGCCTGGCCTCCTCCTACTTGCTCTGGTCG 241        251        261        271        281        291
cdsFAD20_2        TCATCCCTGCCCTCCC---AGGCGTCTC----CGCCTCGTCGCCTGGCCGTTCTACTGG
cdsFAD20_4        GCATCCCTGTCCTCCCTGCAGGCGTCCTGCTCCGGCCGCCTCGTCGCCGGCCGTTCTACTGG
cdsFAD20_1        TGATCCCCGTGCTGCC---GAGCGGGATG---GAGTTCGCGGCATGGCCGCTCTACTGG
cdsFAD20_3        GCATCCCTGCCCTCCC---AAGCATCCTC---CGCCTCGTCGCCTGGCCGCCTCTACTGG
```

Figure 10a

```
            301         311         321         331         341         351
cdsFAD20_2  GCCGCGCAGGGGTGCTTCCTGTTCGGGGTGTGGATCATCGCGCACGAGTGCGGGCACCAC
cdsFAD20_4  GCCGCGCAGGGCTGCTTCCTGTTCGGGGTGTGGATCATCGCGCACGAGTGCGGGCACCAC
cdsFAD20_1  ATCGCGCAGGGCTGCTCCGTGCTCACCGGCGTGTGGGTCATCGCGCACGAGTGCGGCCACCAT
cdsFAD20_3  GCCGCGCAGGGCAGTGTACTCACCGGCGTGTGGGTCATCGGGCACGAGTGTGGCCACCAC 361         371         381         391         401         411
cdsFAD20_2  GCGTTCTCGGGCCACGACTCCTCGACGACACCCTCGGCCTGTCCTGCACTCATGGCTC
cdsFAD20_4  GCG------------CTCCAAGACGACACCCTCGGTCTGTCCTGTCCTGCACTTGTGGCTT
cdsFAD20_1  GCCTTCTCCGACTACTCGGTGCTCGACGACATCGTCGGCCTCGTGCTCACTCGTCGCTG
cdsFAD20_3  GCCTTCTCCGACTACTTCCTCGACAACCTCGTGGGCTTAGTGCTCCACTCGGCGCTT 421         431         441         451         461         471
cdsFAD20_2  CTAGCGCCATACTTCTCGTGGAAATACACCCACCAACGGCACCACTCCAACACCAGCTCA
cdsFAD20_4  CTGGCACCATACTTCTCGTGGAAATACAGCCACCACCAGCCACCACTCCAACACCAGCTCA
cdsFAD20_1  CTCGTCCCCTACTTCTCGTGGAAGTACAGCCACCACCAGCGGCCACCACTCCAACACCGGTCG
cdsFAD20_3  CTCACGCCCTTCTCTTCTCGTGAAGTACAGCCACCACCAGCGCCAACACCACCGGCTCC 481         491         501         511         521         531
cdsFAD20_2  CAGGAGCGCGACGAGGTGTTCGTCCCCAGTTCAAGTCCAGTTCAAGTCCGACCTGCCGTGTACTCCCCA
cdsFAD20_4  CAGGAGCGCGACGAGGTGTTCGTCCCCAGTTCAAGTCCAGTTCAAGTCCGATCTGCCGTGGAACTCCCCG
cdsFAD20_1  CTGGAGCGCGACGAGGTGTTCGTCGTCCCGAAGCAGAAGTCGGCGATGGCGTGGTGGTACACCCCG
cdsFAD20_3  ATGGAGAAAGACGAGGTGTACGTGCCGGAAGAAGAAGTCCGCCGCTGCCGTGGTACACCCCG 541         551         561         571         581         591
cdsFAD20_2  TACGTGTACAAGTACAACAAC--CCCGTCGCTCGGCTCGCTCCTCGTCGTGCAGCTCA
cdsFAD20_4  TACGTGTACAAGTACAACAACGCCCCGTCGCCGGCTACTGCTCCTCGGCATGCAGCTCA
cdsFAD20_1  TACGTGTAC------CACAAC--CCGATCGGCCGTGGTGCACATCTTCGTGCAGCTCA
cdsFAD20_3  TACGTGTTC------GGCAAC--CCCGTCGGGCGGCTGGTGTACATGCCCTGCAGCTCA
```

Figure 10b

```
            601         611         621         631         641         651
cdsFAD20_2  CCGTCGGGTGGCCGATGTATTTGGTGTTCAACACCTGGGGTCGCCAGTACCCAAGGTTCG
cdsFAD20_4  CTGTCGGGTGGCCGATGTATTTGGTGTTCAACACCTGGGGTCGCTGGTACCCGGGTTCG
cdsFAD20_1  CCCTCGGGTGGCCGCTGTACCTGGCGTTCAACGTGTCCGGCCGCCGTACCCGGCGCTTCG
cdsFAD20_3  CCCTCGCGTGGCCACTCTACCTGGCGTTCAACCTGTCCGGGCAGCCGTACCCACGCCCTCG 661         671         681         691         701         711
cdsFAD20_2  ---CCAGCCACTTCGATCCCTCTGGGCCATCTACAAGGGGCGGAGCGCGTCTTCATCG
cdsFAD20_4  ---CCAGCCACTTCGATCCCTCCGGAGCGCATCTACATGAGGCGGAGCGCGTCTTCATCG
cdsFAD20_1  ---CGTGCCACTTCGACCCTCGACCCCTACGGCCGATCCGATCTACAACGACCGGAGCGCGTCCAGATCT
cdsFAD20_3  TCACCTGCCACTGCCACTGACGACCCTACAGCCCGTGTTCAGCGACCAGGAGCGCGTCCAAGTCC 721         731         741         751         761         771
cdsFAD20_2  CCATCTCGGACACATGGCATGCTGGCCCGTGTCGCTCGCGCGCTCGTACAGGCTTGCGGAGGGTT
cdsFAD20_4  CCAGCTCGGACACATGGCATGCTGGCCGTGTCGCTCGCGCGCTCGTAA-----------
cdsFAD20_1  TCATCTCCGACGTCGGGCGTCGTGTCCGGGGCTCGCTGTTCAAGCTGTCGTCGGCGT
cdsFAD20_3  TCGTCTCCGACGCCGACGCCCATCCTGGCCGTGCTGCTCCGCGCTGCTGCACAGCTGACGGCGGCGT 781         791         801         811         821         831
cdsFAD20_2  ACGGGTTTTGGTGGGTGGTGCGCGTCTACGGCCGTGCCGCTGCTTGTCGTCAACGCGTGGC
cdsFAD20_4  ------------------------------------------------------------
cdsFAD20_1  TCGGGTTCTGTGGTGGGTGGTGCCGCGTCTACGGCCGTGCCGCTGCCGCTGATCGTGAACGCGTGGC
cdsFAD20_3  ACGGGCTCGTGGTGGGTGGTGCCGCGTGTACGGCCGTGCCGCTGCCGGTGATGATCGTGGGCGCGTGT 841         851         861         871         881         891
cdsFAD20_2  TTGTGGTCGTCACGTACCTGCATCACACTCACGGGCGATCCCACACTACGACTCCAGCG
cdsFAD20_4  ------------------------------------------------------------
cdsFAD20_1  TGGTGCTCATCACCTACCTGCAGCACACCACCACCCGGCGCTGCCGCACTACGACTCGAGCG
cdsFAD20_3  TCGTGCTCATCACGTACCTGCACCACACCACCACCCGCGCTCCCGCACTACGACTCCAGCG
```

Figure 10c

```
                901        911        921        931        941        951
cdsFAD20_2   AGTGGGACTGGTTGCGCGGGGCCTCGCCACCGTCGCCACCGTGACCGCGACTACAGCTTCCTTAACC
cdsFAD20_4   ------------------------------------------------------------------
cdsFAD20_1   AGTGGGACTGGCTCCGCGCGCGGCGCGCGCTCGCCACCGTGACCGCGACTACGGCATCCTCAACA
cdsFAD20_3   AGTGGGAGTGGCTGCGTGCTCGCTCGCCACCGTCGCCACCGTGACCGCGACTACGGCGTCCTCAACC 961        971        981        991       1001       1011
cdsFAD20_2   GAGTGTTTCACAACATCACGGACACACACGTCGTGCACCACCTGTTCCCTACCATCCCGC
cdsFAD20_4   ------------------------------------------------------------------
cdsFAD20_1   AGGTGTTCCACAACATCACGGACACGCACGTCGCGCACCACCTCTTCTCCACCATGCCGC
cdsFAD20_3   GCGTGCTGCACAACGTCACGGACACGCACGTCACGCACCACCTCTTCCCCCAGCAGCCAC 1021       1031       1041       1051       1061       1071
cdsFAD20_2   ACTACCACGCTGTGGAGGCGACCAAGGCGATCCGCCCCTATCCTCGGCGAGTACTACCAGT
cdsFAD20_4   ------------------------------------------------------------------
cdsFAD20_1   ACTACCACGCCATGGAGGCCACTAAGGCGATCCGCCCCATCCTCGGCGAGTACTACCAGT
cdsFAD20_3   ACTACCACGCCATGGAGGCCACCAGGCGAGCGCGAGGCGCCGTCCTCGGTGAGTACTACAAGT 1081       1091       1101       1111       1121       1131
cdsFAD20_2   TCGATCCCACACCCATCGTCAAGGCCGATATGGCGGAGGCTAAGGAGTGCATCTACATCC
cdsFAD20_4   ------------------------------------------------------------------
cdsFAD20_1   TCGACCCGACGCCCGTCGCCAAGGCCGACATGGGCGACATGGCGAAGGCCATCTACGTCG
cdsFAD20_3   TTGACCGCACGCCATCATCGAGGCAACATGGCGTGAGGCAAGGCCAAGGAGTGCATGTACGTTG 1141       1151       1161       1171       1181
cdsFAD20_2   AGTCCGAGGACCACAAGGGCGTCTCTCTGGTACAGCAACAAGTTCTAG
cdsFAD20_4   ------------------------------------------------------------------
cdsFAD20_1   AGCCTGAGGACAACAAGGGCGTCTCTTCTGGTACAACAACAAGTTCTAA
cdsFAD20_3   AGCCCAGGAGGCGATGGTATCTACTGGTACAACAACAAGTTTTAG
```

Figure 10d

ALTERING THE FATTY ACID COMPOSITION OF RICE

This application is a §371 national stage of PCT International Application No. PCT/AU2007/000977, filed Jul. 13, 2007, and claims priority of Australian Patent Application No. 2006903810, filed Jul. 14, 2006, the contents of all of which are hereby incorporated by reference into this application.

FIELD OF THE INVENTION

The present invention relates to rice oil, rice bran and rice seeds which have altered levels of oleic acid, palmitic acid and/or linoleic acid. The present invention also provides methods for genetically modifying rice plants such that rice oil, rice bran and rice seeds produced therefrom have altered levels of oleic acid, palmitic acid and/or linoleic acid.

BACKGROUND OF THE INVENTION

Plant oils are an important source of dietary fat for humans, representing about 25% of caloric intake in developed countries (Broun et al., 1999). The current world production of plant oils is about 110 million tones per year, of which 86% is used for human consumption. Almost all of these oils are obtained from oilseed crops such as soybean, canola, sunflower, cottonseed and groundnut, or plantation trees such as palm, olive and coconut (Gunstone, 2001; Oil World Annual, 2004). The growing scientific understanding and community recognition of the impact of the individual fatty acid components of food oils on various aspects of human health is motivating the development of modified vegetable oils that have improved nutritional value while retaining the required functionality for various food applications. These modifications require knowledge about the metabolic pathways for plant fatty acid synthesis and genes encoding the enzymes for these pathways (Liu et al., 2002a; Thelen and Ohlrogge, 2002).

Considerable attention is being given to the nutritional impact of various fats and oils, in particular the influence of the constituents of fats and oils on cardiovascular disease, cancer and various inflammatory conditions. High levels of cholesterol and saturated fatty acids in the diet are thought to increase the risk of heart disease and this has led to nutritional advice to reduce the consumption of cholesterol-rich saturated animal fats in favour of cholesterol-free unsaturated plant oils (Liu et al., 2002a).

While dietary intake of cholesterol present in animal fats can significantly increase the levels of total cholesterol in the blood, it has also been found that the fatty acids that comprise the fats and oils can themselves have significant effects on blood serum cholesterol levels. Of particular interest is the effect of dietary fatty acids on the undesirable low density lipoprotein (LDL) and desirable high density lipoprotein (HDL) forms of cholesterol in the blood. In general, saturated fatty acids, particularly myristic acid (14:0) and palmitic acid (16:0), the principal saturates present in plant oils, have the undesirable property of raising serum LDL-cholesterol levels and consequently increasing the risk of cardiovascular disease (Zock et al., 1994; Hu et al., 1997). However, it has become well established that stearic acid (18:0), the other main saturate present in plant oils, does not raise LDL-cholesterol, and may actually lower total cholesterol (Bonanome and Grundy, 1988; Dougherty et al., 1995). Stearic acid is therefore generally considered to be at least neutral with respect to risk of cardiovascular disease (Tholstrup, et al., 1994). On the other hand, unsaturated fatty acids, such as the monounsaturate oleic acid (18:1) and the polyunsaturates linoleic acid (18:2) and α-linolenic acid (ALA, 18:3), have the beneficial property of lowering LDL-cholesterol (Mensink and Katan, 1989; Roche and Gibney, 2000), thus reducing the risk of cardiovascular disease.

Although nutritionally desirable, highly unsaturated oils are too unstable for use in many food applications, particularly for commercial deep-frying where they are exposed to high temperatures and oxidative conditions for long periods of time. Under such conditions, the oxidative breakdown of the numerous carbon double bonds present in unsaturated oils results in the development of short-chain aldehyde, hydroperoxide and keto derivatives, imparting undesirable flavours and reducing the frying performance of the oil by raising the level of polar compounds (Chang et al., 1978; Williams et al., 1999).

Oil processors and food manufacturers have traditionally relied on hydrogenation to reduce the level of unsaturated fatty acids in oils, thereby increasing their oxidative stability in frying applications and also providing solid fats for use in margarine and shortenings. Hydrogenation is a chemical process that reduces the degree of unsaturation of oils by converting carbon double bonds into carbon single bonds. Complete hydrogenation produces a fully saturated fat. However, the process of partial hydrogenation results in increased levels of both saturated fatty acids and monounsaturated fatty acids. Some of the monounsaturates formed during partial hydrogenation are in the trans isomer form (such as elaidic acid, a trans isomer of oleic acid) rather than the naturally occurring cis isomer (Sebedio et al., 1994; Fernandez San Juan, 1995). In contrast to cis-unsaturated fatty acids, trans-fatty acids are now known to be as potent as palmitic acid in raising serum LDL cholesterol levels (Mensink and Katan, 1990; Noakes and Clifton, 1998) and lowering serum HDL cholesterol (Zock and Katan, 1992), and thus contribute to increased risk of cardiovascular disease (Ascherio and Willett, 1997). As a result of increased awareness of the antinutritional effects of trans-fatty acids, there is now a growing trend away from the use of hydrogenated oils in the food industry, in favour of fats and oils that are both nutritionally beneficial and can provide the required functionality without hydrogenation, in particular those that are rich in either oleic acid where liquid oils are required or stearic acid where a solid or semi-solid fat is preferred.

Plant oils are composed almost entirely of triacylglycerols (TAG) molecules, which consist of three fatty acid (acyl) chains esterified to a glycerol backbone and are deposited in specialised oil body structures called oleosomes (Stymne and Stobart, 1987). These storage lipids serve as an energy source for the germinating seedling until it is able to photosynthesise. Edible plant oils in common use are generally comprised of five main fatty acids—the saturated palmitic and stearic acids, the monounsaturated oleic acid, and the polyunsaturated linoleic and α-linolenic acids. In addition to fatty acids, plant oils also contain some important minor components such as tocopherols, phytosterols, terpenes and mixed isoprenoids. These minor constituents are of increasing interest because some have been shown to exert beneficial effects on skin health, aging, eyesight and blood cholesterol or preventing breast cancer or cardiovascular disease (Theriault et al., 1999; Moghadasian and Frohlich, 1999).

Fatty Acid and TAG Synthesis in Seeds

A diagrammatic overview of the metabolic pathways for fatty acids synthesis in developing seeds is shown in FIG. 1. The initial stages of fatty acid synthesis occur in the plastid compartments of the cell, where synthesis of fatty acid carbon chains is initiated with a C2 molecule and extended through a stepwise condensation process whereby additional C2 carbon units are donated from malonyl-ACP to the elongating acyl chains. The first step in this sequence involves acetyl-CoA condensing with malonyl-ACP and is catalysed by the β-ketoacyl synthase III (KASIII) enzyme. The subsequent condensation rounds are catalysed by β-ketoacyl synthase I (KASI) and result in the eventual formation of a saturated C16 acyl chain joined to acyl carrier protein (ACP), palmitoyl-ACP. The final elongation within the plastid is catalysed by β-ketoacyl synthase II (KASII) to form the saturated C18 acyl chain, stearoyl-ACP. When desaturation occurs, the first double bond is introduced into the Δ9 position of the C18 chain by a soluble enzyme in the plastid, stearoyl-ACP Δ9-desaturase, to yield the monounsaturated C18:1 oleoyl-ACP.

Fatty acids thus synthesised are either retained in the plastid for further modification and incorporation into plastidic lipids, or are released from their ACPs by acyl-thioesterases to produce free fatty acids which are exported into the cytosol for further modification and eventual incorporation into TAG molecules. Higher plants have been found to have at least two types of acyl-thioesterase, FatA with substrate specificity towards oleoyl-ACP, an unsaturated acyl-ACP, and FatB with preference for saturated acyl-ACPs (Jones et al., 1995; Voelker et al., 1996).

On exiting the plastids, free fatty acids become esterified to Co-enzyme A (CoA) and are then available for transfer to glycerol 3-phosphate (G-3-P) backbones to form lysophosphatidic acid (LPA), phosphatidic acid (PA) and phosphatidyl-choline (PC). Additionally, in some plants, notably the *Brassica* species, oleic acid esterified to CoA is able to be elongated to form eicosenoic acid (C20:1) and erucic acid (C22:1). Oleic acid esterified to PC is available for further modification before incorporation into TAG. In edible oils, the principal modifications on PC are the sequential desaturations of oleic acid to form linoleic and α-linolenic acids by the microsomal Δ12-desaturase (Fad2) and Δ15-desaturase (Fad3) enzymes respectively.

Modification of Existing Fatty Acid Biosynthetic Enzymes

Gene inactivation approaches such as post transcriptional gene silencing (PTGS) have been successfully applied to inactivate fatty acid biosynthetic genes and develop nutritionally improved plant oils in oilseed crops. For example, soybean lines with 80% oleic acid in their seed oil were created by cosuppression of the Fad2 encoded microsomal Δ12-desaturase (Kinney, 1996). This reduced the level of Δ12-desaturation and resulted in accumulation of high amounts of oleic acid. Using a similar approach, cosuppression-based silencing of the Fad2 gene was used to raise oleic acid levels in *Brassica napus* and *B. juncea* (Stoutjesdijk et al., 2000). Likewise, transgenic expression in cottonseed of a mutant allele of the Fad2 gene obtained from rapeseed was found to be able to suppress the expression of the endogenous cotton Fad2 gene and resulted in elevated oleic acid content in about half of the primary transgenic cotton lines (Chapman et al., 2001). In another variation, transgenic expression in soybean of a Fad2 gene terminated by a self-cleaving ribozyme was able to inactivate the endogenous Fad2 gene resulting in increased oleic acid levels (Buhr et al., 2002). RNAi-mediated gene silencing techniques have also been employed to develop oilseeds with nutritionally-improved fatty acid composition. In cottonseed, transgenic expression of a hairpin RNA (hpRNA) gene silencing construct targeted against ghFad2-1, a seed-specific member of cotton Fad2 gene family, resulted in the increase of oleic acid from normal levels of 15% up to 77% of total fatty acids in the oil (Liu et al., 2002b).

This increase was mainly at the expense of linoleic acid which was reduced from normal levels of 60% down to as low as 4%.

Fatty Acids in Cereals

In contrast to the considerable work done on fatty acid biosynthesis and modification in oilseeds, oil modification in cereals is relatively unexplored. This is probably due to the much lower levels of oils (about 1.5-6% by weight) in cereal grains and consequently the perceived lower importance of oils from cereals in the human diet.

Rice (*Oryza sativa* L.) is the most important cereal crop in the developing world and is grown widely, particularly in Asia which produces about 90% of the world total. The vast majority of rice in the world is eaten as "white rice" which is essentially the endosperm of the rice grain, having been produced by milling of harvested grain to remove the outer bran layer and germ (embryo and scutellum). This is done primarily because "brown rice" does not keep well on storage, particularly under hot tropical conditions.

The oil content of cereal grains such as rice (4%) is quite low relative to oilseeds where oil can make up to 60% of the weight of the grain (Ohlrogge and Jaworski, 1997). However, lipids may still comprise up to 37% of the dry weight of the cereal embryo (Choudhury and Juliano 1980). Most of the lipid content in the rice grain is found in the outer bran layer (Resurreccion et al, 1979) but some is also present in the endosperm, at least some associated with the starch (Tables 1 and 2). The main fatty acids in rice oil are palmitic (16:0) (about 20% of total fatty acids in the TAG), oleic (18:1) (about 40%), and linoleic acids (18:2) (about 34%) (Radcliffe et al., 1997). There is a range of levels naturally occurring in different rice cultivars, for example for oleic acid, from 37.9% to 47.5% and for linoleic (18:2), from 38.2% to 30.4% (Taira et al., 1988).

TABLE 1

Typical fatty acid composition (wt % of total fatty acids) for selected fatty acids of various plant oils.

| Plant | 16:0 | 18:1 | 18:2 |
| --- | --- | --- | --- |
| Barley | 18 | 22 | 54 |
| Soybean | 11 | 23 | 51 |
| Peanut | 8 | 50 | 36 |
| Canola | 4 | 63 | 20 |
| Olive | 15 | 75 | 9 |
| Rice bran | 22 | 38 | 34 |

While the FatB gene has been shown to have a high affinity to catalysing the production of free palmitic acid which is subsequently converted to palmitoyl-CoA in oilseed plants and dicot plants, no information is reported on the role of FatB in rice or other cereals.

TABLE 2

Fatty acid composition (wt % of total fatty acids) for selected fatty acids of plant lipids associated with starch.

| Plant | 16:0 | 18:1 | 18:2 |
| --- | --- | --- | --- |
| Wheat | 35-44 | 6-14 | 42-52 |
| Barley | 55 | 4 | 36 |
| Rye | 23 | 41 | 35 |
| Oat | 40 | 22 | 35 |
| Maize | 37 | 11 | 46 |
| Maize- High amylose | 36 | 20 | 38 |
| Maize- waxy | 36 | 23 | 36 |
| Millet | 36 | 28 | 29 |
| Rice | 37-48 | 9-18 | 29-46 |

Data adapted from: Morrison (1988).

Some of the fatty acid desaturases have been characterized in rice but not Fad2. Akagai et al, (1995) published the nucleotide sequence of a gene on rice chromosome 4 encoding stearoyl-acyl carrier protein desaturase from developing seeds. The gene product participates in the production of oleoyl ACP from stearoyl ACP. Kodama et al. (1997) reported the structure, chromosomal location and expression of Fad3 in rice.

The proportion of linolenic acid (18:3) in rice seed oil has been increased ten-fold by using soybean Fad3 expression (Anai et al., 2003). More recently, there have been reports of the production of conjugated linoleic acid in rice by introduction of a linoleate isomerase gene from bacteria (Kohno-Murase et al., 2006); conjugated linoleic acid is reported to have anti-carcinogenic activity. In a similar vein, in vitro modification of rice bran oil to incorporate capric acid, which may improve dietary lipid utilisation in some diseases, using immobilized microbial enzymes has also been reported (Jennings and Akoh, 2000). In maize, Fad2 and FA-6 desaturase genes have been sequenced and mapped to chromosomes (Mikkilinen and Rocheford, 2003). The Fad2 and Fad6 clones could not be mapped to any QTLs for oleic/linoliec acid ratios in the maize grain. There are no published reports of other Fad2 or FatB genes characterized from rice, maize or wheat.

Storage of Rice

Storage of rice for prolonged times at high temperatures impairs grain quality due to hydrolytic and oxidative deterioration of bran oil. Dehulling the outer husk during harvest to produce brown rice disturbs the outer bran layers, which allows the oil to diffuse to the outer layers. Endogenous and microbial lipases then catalyse the hydrolysis of triglycerides to free fatty acids (FFA) which are then oxidised to produce an off-flavour (Yasumatsu et al., 1966, Tsuzuki et al., 2004, Zhou et al., 2002 Champagne and Grimm, 1995).

Hexanal is the major component increased in the headspace of raw and cooked brown rice stored at high temperatures (Boggs et al., 1964, Shibuya et al., 1974, Tsugita et al., 1983). However, hexanal itself is not the main cause of the 'off' smell; the unattractive smell and flavour of deteriorated rice is probably due to a mixture of the volatiles that are increased after storage. These include alkanals, alkenals, aromatic aldehydes, ketones, 2-pentylfuran, 4-vinylphenol and others (Tsugita et al., 1983). Nevertheless, hexanal levels during storage have been shown to be associated with the oxidation of linoleic acid (18:2) in brown rice and therefore are a good indicator of oxidative deterioration (Shin et al., 1986).

The production of hexanal from linoleic acid can be catalysed by the enzyme lipoxygenase (LOX) (St Angelo et al., 1980). Suzuki et al. (1999) identified rice varieties lacking Lox3 and found that on storage of the mutant grain at 35° C. for 8 weeks, less hexanal was formed in the headspace vapour, both for raw and cooked brown rice grain. They also found that mutant rice formed less pentanal and pentanol.

The nutrient-rich outer rice bran layer obtained through polishing the outer layers of the rice grain is an excellent food source, containing antioxidant compounds such as tocotrienols and gamma-oryzanol which is also a phytoestrogen (Rukmini and Raghuram, 1991). The bioactive compounds present in rice bran oil have been found to lower cholesterol in humans (Most et al., 2005). These bioactive components have also been shown to improve lipid profiles in rats fed a high cholesterol diet (Ha et al., 2005). Another important component found primarily in the bran is vitamin A precursors. However, these nutritional and health benefits are lost through the polishing of rice and the consumption of white rice.

There is still a need for cereal, such as rice, varieties that produce grain with an improved oil composition for health benefits, which at the same time is more stable on storage, allowing greater use of, for example, brown rice in the human diet.

SUMMARY OF THE INVENTION

In one aspect, the present invention provides rice oil having a fatty acid composition comprising greater than about 48% oleic acid, less than about 17% palmitic acid, less than about 30% linoleic acid and/or any combination thereof.

In an embodiment, the ratio of oleic acid to linoleic acid is greater than 1.5:1, preferably greater than 2:1, more preferably greater than 3:1, and even more preferably greater than 4:1.

In another embodiment, the rice oil has a fatty acid composition comprising greater than about 48% oleic acid, less than about 17% palmitic acid, and less than about 30% linoleic acid.

In a further embodiment, the rice oil has a fatty acid composition comprising greater than about 40% oleic acid, preferably greater than about 50% oleic acid, and even more preferably greater than about 60% oleic acid. In an embodiment, the fatty acid composition of the rice oil is in the range 48-80% oleic acid, 6-16% palmitic acid and 10-25% linoleic acid.

In yet another embodiment, the rice oil has a fatty acid composition comprising less than about 16% palmitic acid, preferably less than about 15% palmitic acid, more preferably less than about 14% palmitic acid, more preferably less than about 13% palmitic acid, and even more preferably less than about 12% palmitic acid.

In another embodiment, the rice oil has a fatty acid composition comprising less than about 25% linoleic acid, preferably less than about 20% linoleic acid, even more preferably less than about 15% linoleic acid.

In another aspect the present invention provides rice bran having a fatty acid composition comprising greater than about 48% oleic acid, less than about 17% palmitic acid, less than about 30% linoleic acid and/or any combination thereof.

In an embodiment, the ratio of oleic acid to linoleic acid is greater than 1.5:1, preferably greater than 2:1, more preferably greater than 3:1, and even more preferably greater than 4:1.

In another embodiment, the rice bran has a fatty acid composition comprising greater than about 48% oleic acid, less than about 17% palmitic acid, and less than about 30% linoleic acid.

In a further embodiment, the rice bran has a fatty acid composition comprising greater than about 40% oleic acid, preferably greater than about 50% oleic acid, and even more preferably greater than about 60% oleic acid. In an embodiment, the fatty acid composition of the rice bran is in the range 48-80% oleic acid, 6-16% palmitic acid and 10-25% linoleic acid.

In yet another embodiment, the rice bran has a fatty acid composition comprising less than about 16% palmitic acid, preferably less than about 15% palmitic acid, more preferably less than about 14% palmitic acid, more preferably less than about 13% palmitic acid, and even more preferably less than about 12% palmitic acid.

In another embodiment, the rice bran has a fatty acid composition comprising less than about 25% linoleic acid, preferably less than about 20% linoleic acid, even more preferably less than about 15% linoleic acid.

In a further aspect, the present invention provides a rice seed having a fatty acid composition comprising greater than about 48% oleic acid, less than about 17% palmitic acid, less than about 30% linoleic acid and/or any combination thereof.

In an embodiment, the ratio of oleic acid to linoleic acid is greater than 1.5:1, preferably greater than 2:1, more preferably greater than 3:1, and even more preferably greater than 4:1.

In another embodiment, the rice seed has a fatty acid composition comprising greater than about 48% oleic acid, less than about 17% palmitic acid, and less than about 30% linoleic acid.

In a further embodiment, the rice seed has a fatty acid composition (i.e. of the oil inside the seed) comprising greater than about 40% oleic acid, preferably greater than about 50% oleic acid, and even more preferably greater than about 60% oleic acid. In an embodiment, the fatty acid composition of the rice seed is in the range 48-80% oleic acid, 6-16% palmitic acid and 10-25% linoleic acid.

In yet another embodiment, the rice seed has a fatty acid composition comprising less than about 16% palnitic acid, preferably less than about 15% palmitic acid, more preferably less than about 14% palmitic acid, more preferably less than about 13% palmitic acid, and even more preferably less than about 12% palmitic acid.

In another embodiment, the rice seed has a fatty acid composition comprising less than about 25% linoleic acid, preferably less than about 20% linoleic acid, even more preferably less than about 15% linoleic acid.

In any of the embodiments described above for rice bran or rice seed, the fatty acid composition is typically determined by extraction of the oil and analysis by FAME/GC as described in Example 1. Compositions for individual fatty acids are expressed as percent (w/w) of the total fatty acids in the oil.

In a further aspect, provided is a rice plant which produces rice oil of the invention, rice bran of the invention, and/or a rice seed of the invention.

In another aspect, the present invention provides an isolated polynucleotide which, when present in a cell of a rice plant, down-regulates the level of activity of a Fad2 and/or FatB polypeptide in the cell when compared to a cell that lacks said polynucleotide.

Preferably, the polynucleotide is operably linked to a promoter capable of directing expression of the polynucleotide in a cell of a rice plant.

In an embodiment, the polynucleotide down-regulates mRNA levels expressed from at least one Fad2 and/or FatB gene.

Examples of suitable polynucleotides include, but are not limited to, a polynucleotide selected from: an antisense polynucleotide, a sense polynucleotide, a catalytic polynucleotide, a microRNA, a polynucleotide which encodes a polypeptide which binds a Fad2 or FatB polypeptide and a double stranded RNA.

In an embodiment, the polynucleotide is an antisense polynucleotide which hybridises under physiological conditions to a polynucleotide comprising any one or more of the sequence of nucleotides provided as SEQ ID NOs 5 to 8, 11 to 14 or 19 to 25.

In a further embodiment, the polynucleotide is a catalytic polynucleotide capable of cleaving a polynucleotide comprising any one or more of the sequence of nucleotides provided as SEQ ID NOs 5 to 8, 11 to 14 or 19 to 25.

In another embodiment, the polynucleotide is a double stranded RNA (dsRNA) molecule comprising an oligonucleotide which comprises at least 19 contiguous nucleotides of any one or more of the sequence of nucleotides provided as SEQ ID NOs 5 to 8, 11 to 14 or 19 to 25, wherein the portion of the molecule that is double stranded is at least 19 basepairs in length and comprises said oligonucleotide.

Preferably, the dsRNA is expressed from a single promoter, wherein the strands of the double stranded portion are linked by a single stranded portion. Examples of the construction of vectors to produce such dsRNA molecules is provided in Example 5.

In a preferred embodiment, the polynucleotide, or a strand thereof, is capable of hybridising to a polynucleotide comprising any one or more of the sequence of nucleotides provided as SEQ ID NOs 5 to 8, 11 to 14 or 19 to 25 under stringent conditions.

In a further aspect, the present invention provides a method of identifying a polynucleotide which, when present in a cell of a rice plant, down-regulates the level of activity of a Fad2 and/or FatB polypeptide in the cell when compared to a cell that lacks said polynucleotide, the method comprising i) determining the ability of a candidate polynucleotide to down-regulate the level of activity of a Fad2 and/or FatB polypeptide in a cell, and ii) selecting a polynucleotide which down-regulated the level of activity of a Fad2 and/or FatB polypeptide in the cell.

Step i) can rely on, for example, analysing the amount or enzymatic activity of a Fad2 and/or FatB polypeptide, or the amount of mRNA encoding a Fad2 and/or FatB polypeptide in the cell. Alternatively, step i) may comprise analysing the fatty acid content of the cell, or a seed or plant comprising said cell. Preferably, step i) comprises the introduction of the candidate polynucleotide or a chimeric DNA including a promoter operably linked to the candidate polynucleotide into a plant cell, more preferably into a rice cell, and even more preferably comprises the step of regenerating a transgenic plant from the plant cell and the production of seed from the transgenic plant. The candidate gene may be one of a collection of candidate genes, at least 2 or 3 in number. The invention therefore provides for the use of the polynucleotides of the invention in a screening method.

The polynucleotide can be, but not limited to, an antisense polynucleotide, a sense polynucleotide, a catalytic polynucleotide, a microRNA, a polynucleotide which encodes a polypeptide which binds a Fad2 or FatB polypeptide and a double stranded RNA.

In an embodiment, the antisense polynucleotide hybridises under physiological conditions to a polynucleotide comprising any one or more of the sequence of nucleotides provided as SEQ ID NOs 5 to 8, 11 to 14 or 19 to 25.

In another embodiment, the catalytic polynucleotide is capable of cleaving a polynucleotide comprising any one or more of the sequence of nucleotides provided as SEQ D NOs 5 to 8, 11 to 14 or 19 to 25.

In a further embodiment, the double stranded RNA (dsRNA) molecule comprises an oligonucleotide which comprises at least 19 contiguous nucleotides of any one or more of the sequence of nucleotides provided as SEQ ID NOs 5 to 8, 11 to 14 or 19 to 25, wherein the portion of the molecule that is double stranded is at least 19 basepairs in length and comprises said oligonucleotide.

Also provided is an isolated polynucleotide identified using a method of the invention.

In a further aspect the present invention provides a vector comprising or encoding a polynucleotide of the invention.

Preferably, the polynucleotide, or sequence encoding the polynucleotide, is operably linked to a promoter. Preferably, the promoter confers expression of the polynucleotide preferentially in the embryo, endosperm, bran layer and/or seed of a rice plant relative to at least one other tissue or organ of said plant.

Also provided is a cell comprising the vector of the invention, and/or the polynucleotide of the invention.

In an embodiment, the polynucleotide or vector was introduced into the cell or a progenitor of the cell.

In a further embodiment, the cell is a rice cell or an *Agrobacterium* cell.

Preferably, the polynucleotide is integrated into the genome of the cell.

In another aspect, the present invention provides a rice plant comprising a cell of the invention.

In yet another aspect, the present invention provides a method of producing the cell of the invention, the method comprising the step of introducing the polynucleotide of the invention, or a vector of the invention, into a cell.

Preferably the method further comprises the step of regenerating a transgenic plant from the cell.

Also provided is the use of the polynucleotide of the invention or a vector of the invention to produce a recombinant cell.

In yet another aspect, the present invention provides a genetically modified rice plant, wherein the plant has decreased expression of a polypeptide having Fad2 and/or FatB activity relative to a corresponding non-modified plant.

Preferably, the plant has been transformed such that it comprises a polynucleotide of the invention, or a progeny plant thereof which comprises said polynucleotide.

In a further aspect the present invention provides a method of producing rice oil of the invention, rice bran of the invention and/or rice seed of the invention, the method comprising exposing a rice plant to an antagonist of a Fad2 or FatB polypeptide.

In another aspect, the present invention provides a method of obtaining a genetically modified rice plant which can be used to produce brown rice seed with an increased storage life when compared to unmodified brown rice seed, the method comprising genetically manipulating the plant such that the activity and/or level of production of a Fad2 and/or FatB polypeptide is reduced in the rice seed when compared to a corresponding plant which produces unmodified brown rice seed.

Preferably, the activity and/or level of production of a Fad2 and/or FatB polypeptide is only reduced in the seed of the plant.

In an embodiment, the activity and/or level of production of a Fad2 polypeptide is reduced.

In a further embodiment, the transgenic plant comprises a polynucleotide of the invention or a vector of the invention.

In a further aspect, the present invention provides a genetically modified rice plant produced using a method of the invention, or progeny thereof.

In a further aspect, the present invention provides a method of selecting a rice plant which can be used to produce rice oil of the invention, rice bran according to the invention and/or rice seed of the invention, the method comprising;

i) screening a mutagenized population of rice seeds or rice plants, and ii) selecting a seed or plant which is capable of producing rice oil of the invention, rice bran of the invention and/or rice seed of the invention.

In one embodiment, step i) comprises analysing a mutagenized seed and/or plant for a polypeptide which has Fad2 or FatB activity.

In another embodiment, step i) comprises analysing the sequence and/or expression levels of a Fad2 or FatB gene of the mutagenized seed and/or plant.

In a further embodiment, step i) comprises analysing the fatty acid composition of the oil, bran and/or seed of the mutagenized seed and/or plant.

In a further aspect, the present invention provides a method of selecting a rice plant which can be used to produce rice oil of the invention, rice bran of the invention and/or rice seed of the invention, the method comprising i) analysing the fatty acid content of said rice oil, rice bran and/or seed obtained from a candidate rice plant, and ii) selecting a rice plant which can be used to produce rice oil of the invention, rice bran of the invention and/or rice seed of the invention.

In yet a further aspect, the present invention provides a method of selecting a rice plant which can be used to produce rice oil of the invention, rice bran of the invention and/or rice seed of the invention, the method comprising i) analysing a sample from a candidate plant for a polypeptide which has Fad2 or FatB activity, and ii) selecting a rice plant which can be used to produce rice oil of the invention, rice bran of the invention and/or rice seed of the invention based on the sequence, level of production and/or activity of said polypeptide.

In another aspect, the present invention provides a method of selecting a rice plant which can be used to produce rice oil of the invention, rice bran of the invention and/or rice seed of the invention, the method comprising i) analysing the sequence and/or expression levels of a Fad2 or FatB gene of a candidate plant, and ii) selecting a rice plant which can be used to produce rice oil of the invention rice bran of the invention and/or rice seed of the invention based on the sequence and/or expression levels of said gene.

In yet another aspect the present invention provides a method of identifying a rice plant which can be used to produce rice oil of the invention, rice bran of the invention and/or rice seed of the invention, the method comprising detecting a nucleic acid molecule of the plant, wherein the nucleic acid molecule is linked to, and/or comprises at least a part of, a Fad2 gene and/or FatB gene in the plant In a further aspect, the present invention provides a method of identifying a rice plant which can be used to produce brown rice seed with an increased storage life, the method comprising detecting a nucleic acid molecule of the plant, wherein the nucleic acid molecule is linked to, and/or comprises at least a part of, a Fad2 gene and/or FatB gene in the plant.

In an embodiment, the above two methods comprise:

i) hybridising a second nucleic acid molecule to said nucleic acid molecule which is obtained from said plant, ii) optionally hybridising at least one other nucleic acid molecule to said nucleic acid molecule which is obtained from said plant; and iii) detecting a product of said hybridising step(s) or the absence of a product from said hybridising step(s).

In an embodiment, the second nucleic acid molecule is used as a primer to reverse transcribe or replicate at least a portion of the nucleic acid molecule.

The nucleic acid can be detected using any technique such as, but not limited to, restriction fragment length polymorphism analysis, amplification fragment length polymorphism analysis, microsatellite amplification and/or nucleic acid sequencing.

In an embodiment, the method comprises nucleic acid amplification. In another embodiment, the method analyses expression levels of the gene.

Also provided is a method of obtaining a rice plant or seed, the method comprising;

i) crossing a first parental rice plant which comprises a Fad2 allele which confers an increased proportion of oleic acid in oil of the grain of the plant with a second parental rice plant which comprises a FatB allele which confers a decreased proportion of palmitic acid in oil of the grain of the plant;

ii) screening progeny plants or grain from the cross for the presence of both alleles; and iv) selecting a progeny plant or grain comprising both alleles and having an increased proportion of oleic acid and a decreased proportion of palmitic acid in oil of the grain of the plant.

In another aspect, the present invention provides a method of introducing a Fad2 allele into a rice plant, the method comprising i) crossing a first parental rice plant with a second parental rice plant, wherein the second plant comprises said allele, and ii) backcrossing the progeny of the cross of step i) with plants of the same genotype as the first parent plant for a sufficient number of times to produce a plant with a majority of the genotype of the first parent but comprising said allele iii) selecting a plant with the majority of the genotype of the first plant and comprising said allele;

wherein said allele confers an increased proportion of oleic acid in oil, bran and/or seed of the plant.

In yet another aspect, the present invention provides a method of introducing a FatB allele into a rice plant, the method comprising i) crossing a first parental rice plant with a second parental rice plant, wherein the second plant comprises said allele, and ii) backcrossing the progeny of the cross of step i) with plants of the same genotype as the first parent plant for a sufficient number of times to produce a plant with a majority of the genotype of the first parent but comprising said allele iii) selecting a plant with the majority of the genotype of the first plant and comprising said allele;

wherein said allele confers a decreased proportion of palmitic acid in oil, bran and/or seed of the plant.

Further, provided is a method of increasing the proportion of oleic acid in oil, bran and/or seed of a rice plant, the method comprising genetically manipulating said plant such that the production of a Fad2 polypeptide is decreased when compared to a wild-type plant, wherein the polypeptide has Δ12 desaturase activity.

In yet another aspect, the present invention provides a method of decreasing the proportion of palmitic acid in oil, bran and/or seed of a rice plant, the method comprising genetically manipulating said plant such that the production of a FatB polypeptide is decreased when compared to a wild-type plant, wherein the polypeptide has (FatB) activity.

Also provided is a rice plant obtained using a method of the invention, or progeny plant thereof.

In a further aspect, the present invention provides rice oil obtained from a plant of the invention.

In a further aspect, the present invention provides rice bran obtained from a plant of the invention.

In a further aspect, the present invention provides rice seed obtained from a plant of the invention.

Further, provided is a method of producing seed, the method comprising;

a) growing a plant of the invention, and
b) harvesting the seed.

In yet another aspect, the present invention provides a food product comprising rice oil of the invention, rice bran of the invention and/or rice seed of the invention.

In another aspect, the present invention provides a method of preparing food, the method comprising cooking an edible substance in rice oil of the invention.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1—Principal fatty acid biosynthetic pathways in plastid and cytosol of higher plants.

FIG. 2—Alignment of rice FatB proteins. ProteinFATB2=SEQ ID NO:1, proteinFATB3=SEQ ID NO:2, proteinFATB1=SEQ ID NO:3 and proteinFATB4=SEQ ID NO:4.

Figure 3:
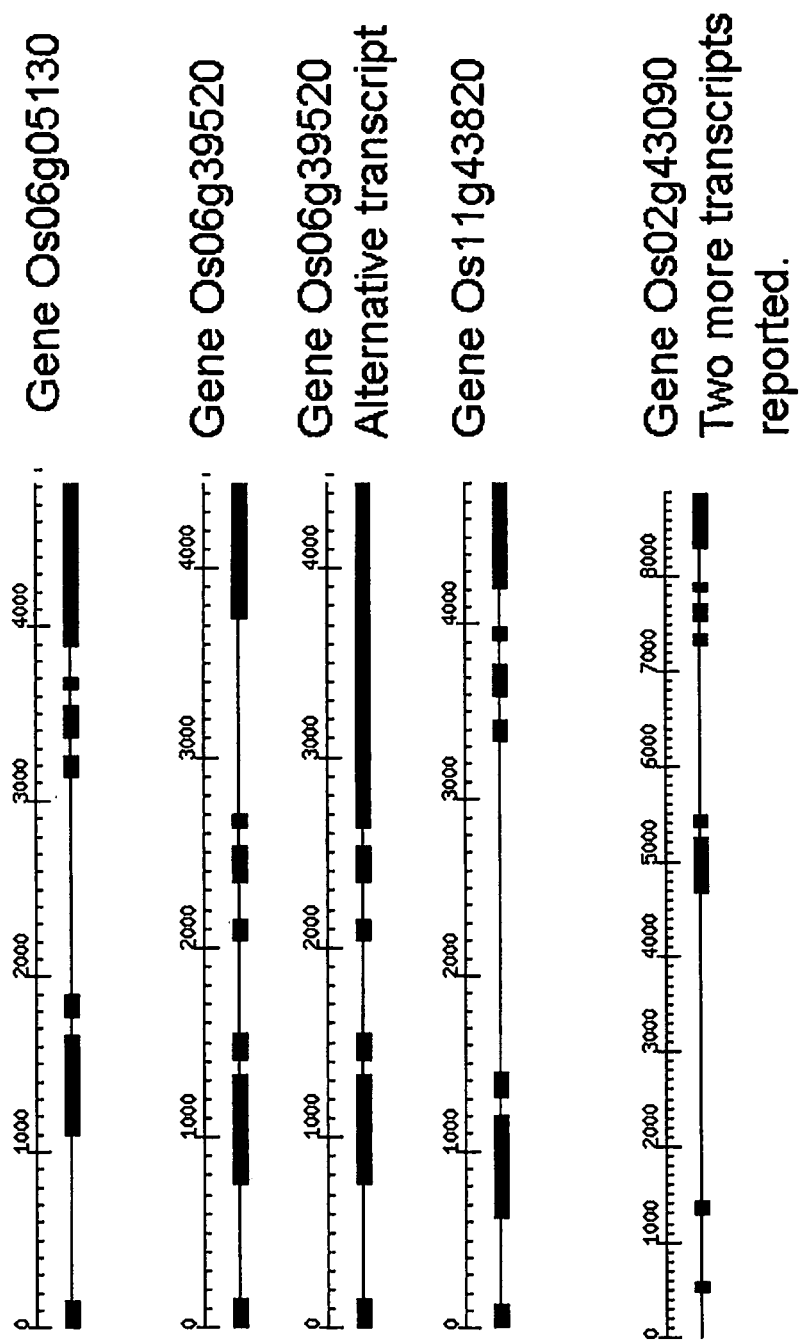

FIG. 3—Rice FatB gene structures. LOC_Os02g4=SEQ ID NO:5, LOC_Os11g4=SEQ ID NO:6, LOC_Os06g0=SEQ ID NO:7 and LOC_Os06g3=SEQ ID NO:8.

FIG. 4—Alignment of FatB gene sequences by ClustalW. Default parameters were used and note that the 'genes' are of different lengths.

FIG. 5—The exon-intron structures of the FatB gene corresponding to LOC_Os6g05130. The top line corresponds to the start of the coding sequence in mRNA (SEQ ID NO:9) and the second line of the pair corresponds to the gene (SEQ ID NO:10).

Figure 6A:
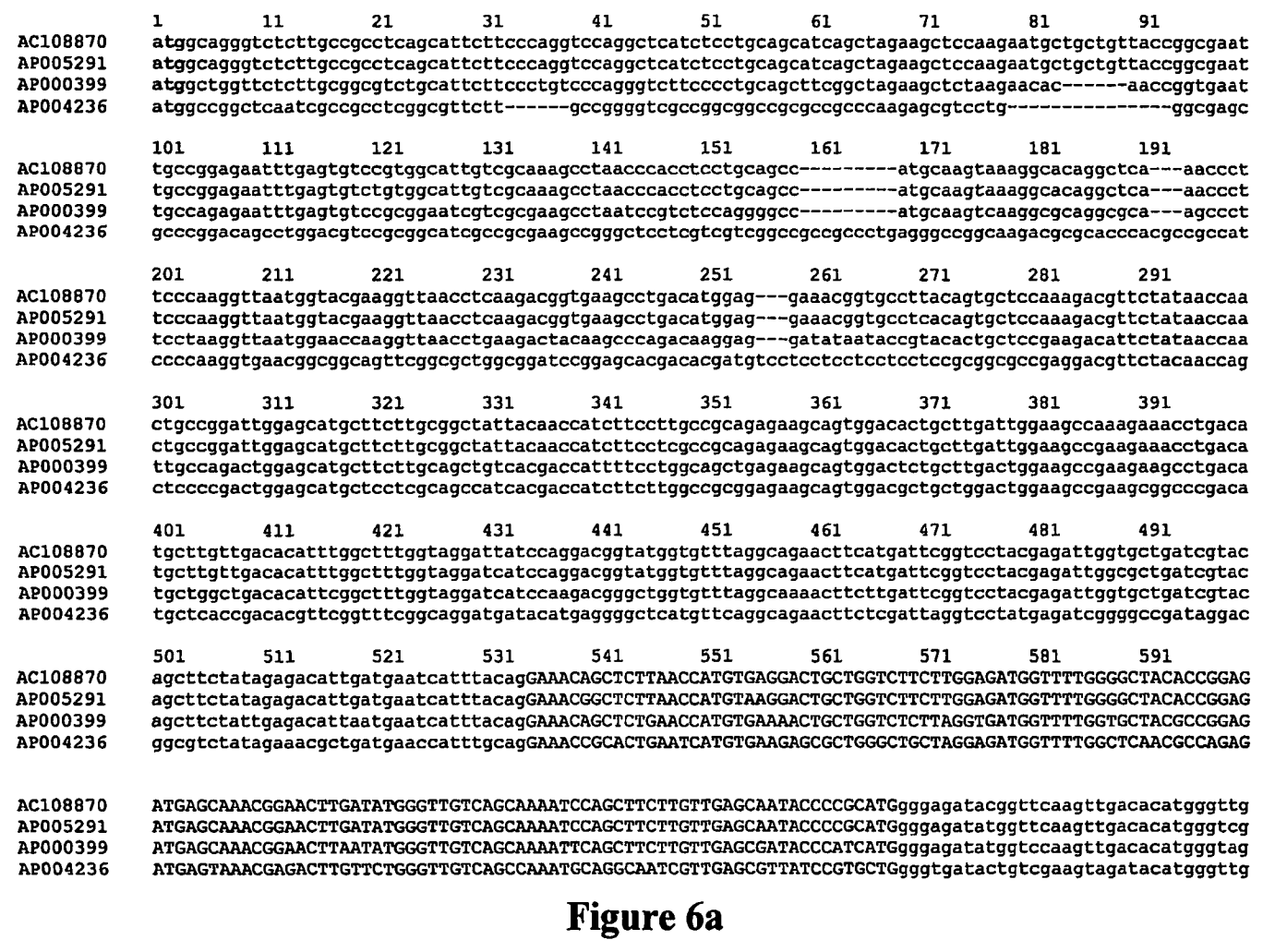
Figure 6B:
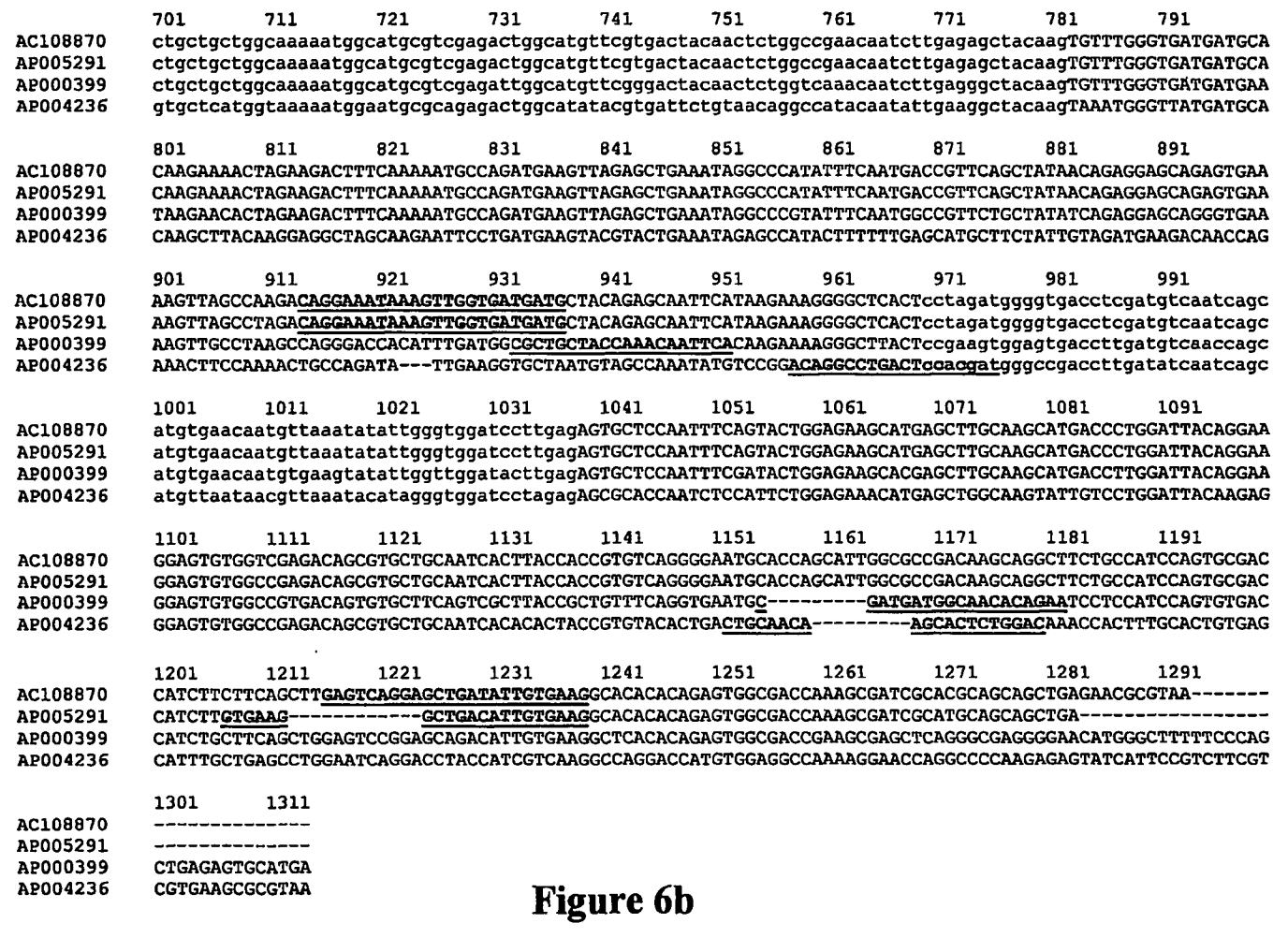

FIG. 6—Alignment of coding sequence of four FatB isoforms showing consecutive exons in alternating lower case and upper case respectively and location of primers (underlined) used to distinguish the isoforms by RT-PCR. The initiating codon (start position 1) is in bold. AC108870=SEQ ID NO:11, AP005291=SEQ ID NO:12, AP000399=SEQ ID NO:13 and AP004236=SEQ ID NO:14.

FIG. 7—Clustal W alignment of deduced polypeptide sequence of Fad2 isoforms. Note that line F_1 corresponds to Os02g48560, F_2 corresponds to Os07g23410, F_3 to Os07g23430 and O_4 to Os07g23390. The program ClustalW (Fast) with default parameters was used. ProteinF_1=SEQ ID NO:15, ProteinF_3=SEQ ID NO:16, ProteinF_2=SEQ ID NO:17 and ProteinF_4=SEQ ID NO:18.

Figure 8A:
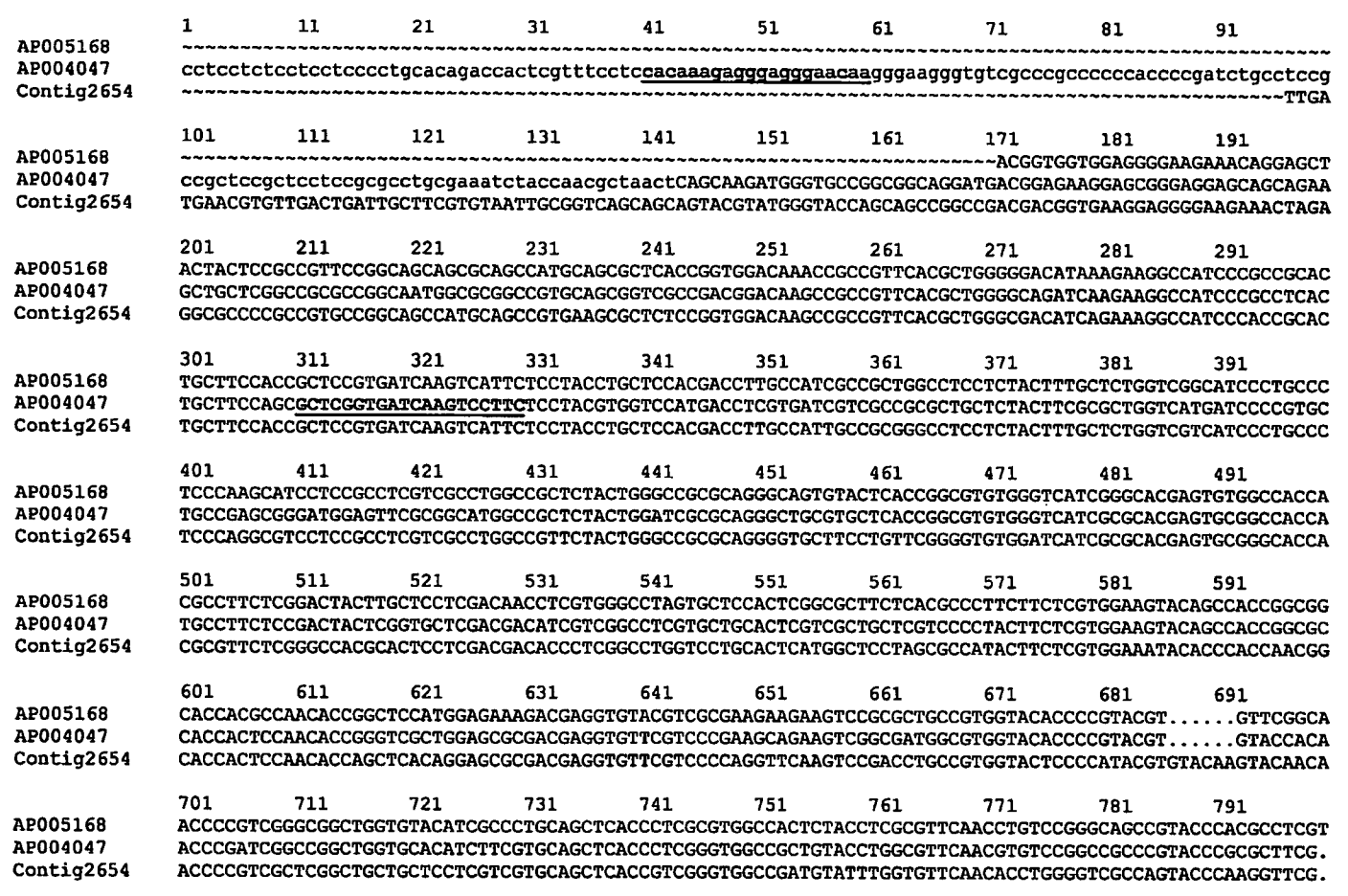
Figure 8B:
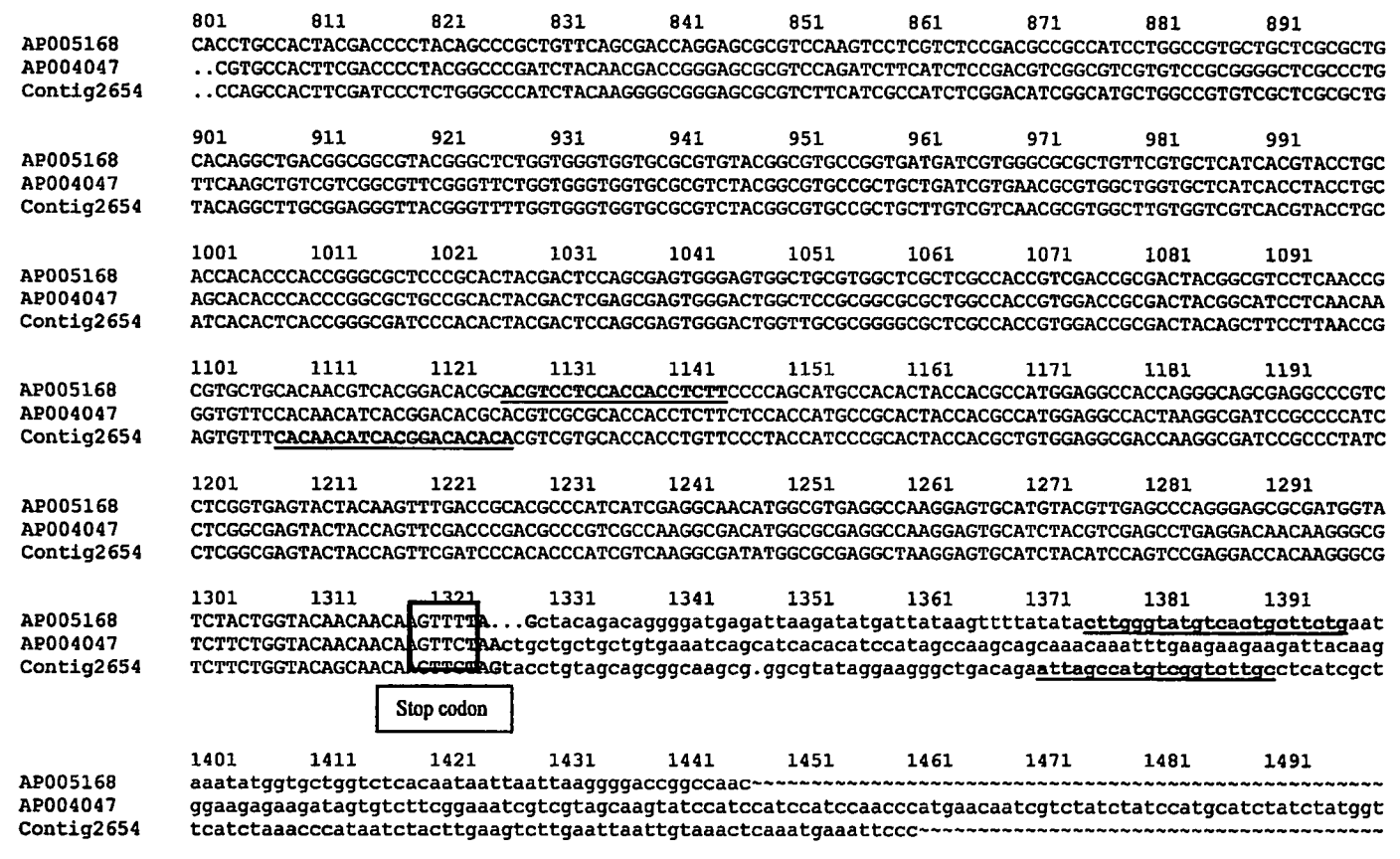

FIG. 8—Alignment of Fad2 sequences showing location of 5' UTR in isoform AP004047 (lowercase) and location of primers used for amplification by RT-PCR (underlined). The location of the stop codon is indicated by a box and untranslated regions downstream of the stop codon are in lower case. AP005168=SEQ ID NO:19, AP004047=SEQ ID NO:20 and Contig2654=SEQ ID NO:21.

Figure 9:
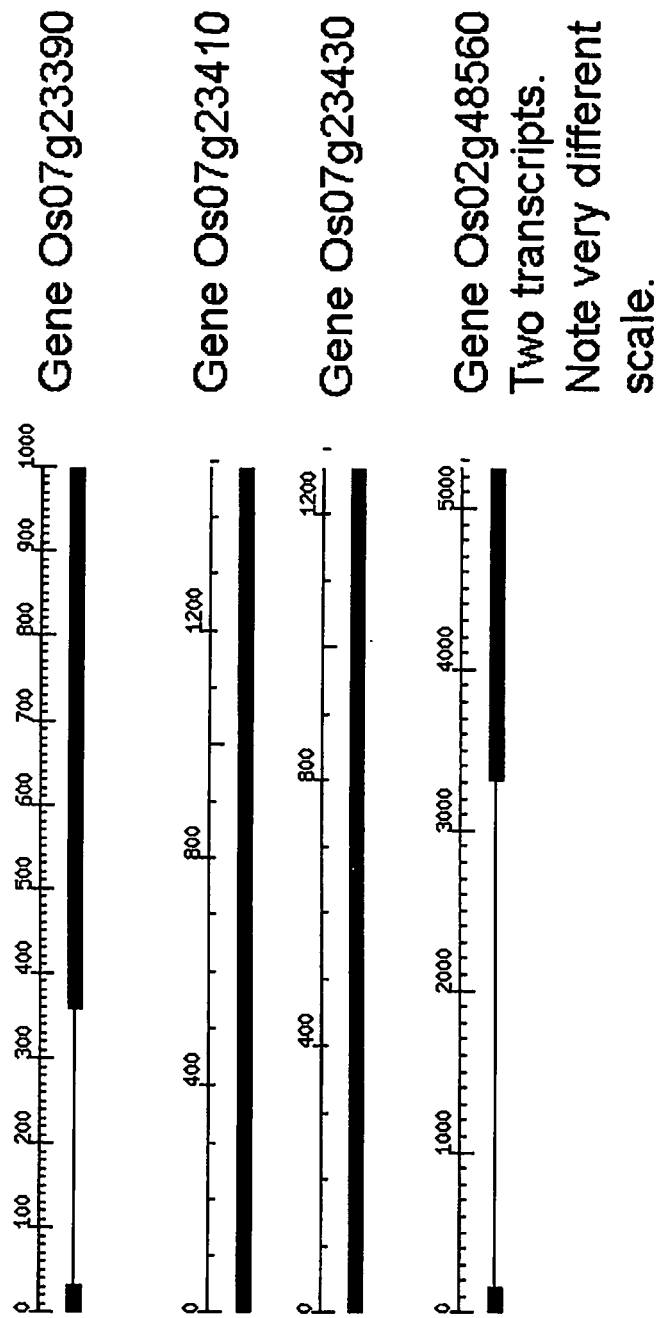

FIG. 9—Rice Fad2 gene structures.

FIG. 10—Alignment of the nucleotide sequences of the protein coding regions for rice Fad2 genes. Line 0_2 corresponds to Os07g23410, O_4 to Os07g23390, O_1 to Os02g48560 and 0_3 to Os07g23410. The program ClustalW with default parameters was used. CdsFAD2O_2=SEQ ID NO:22, CdsFAD2O_4=SEQ ID NO:23, CdsFAD2O_1=SEQ ID NO:24 and CdsFAD2O_3=SEQ ID NO:25.

Figure 11:
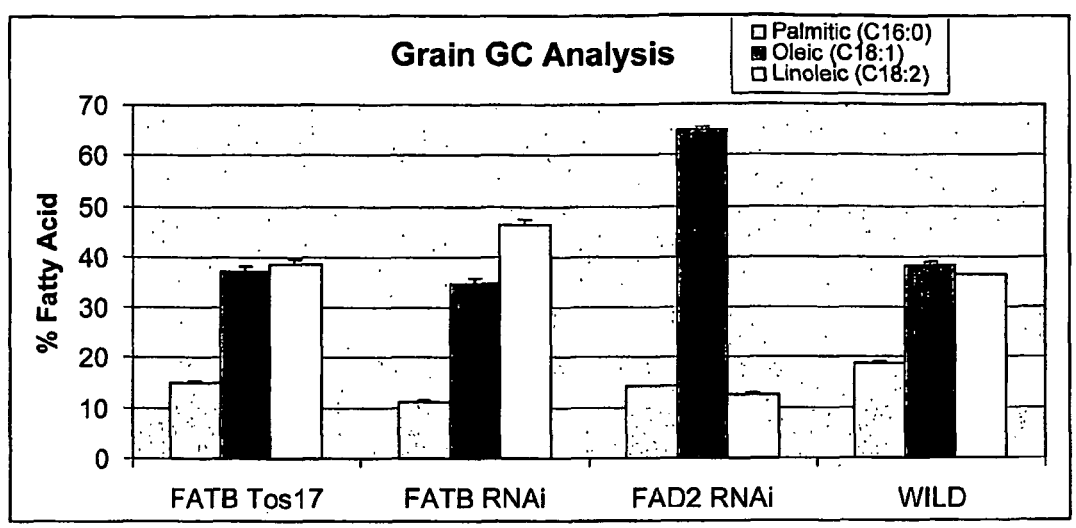

FIG. 11—Graphical representation of the relative percentages of palmitic, oleic and linoleic acid as determined by GC analysis of total oil fraction from grains of indicated genotypes.

Figure 12:
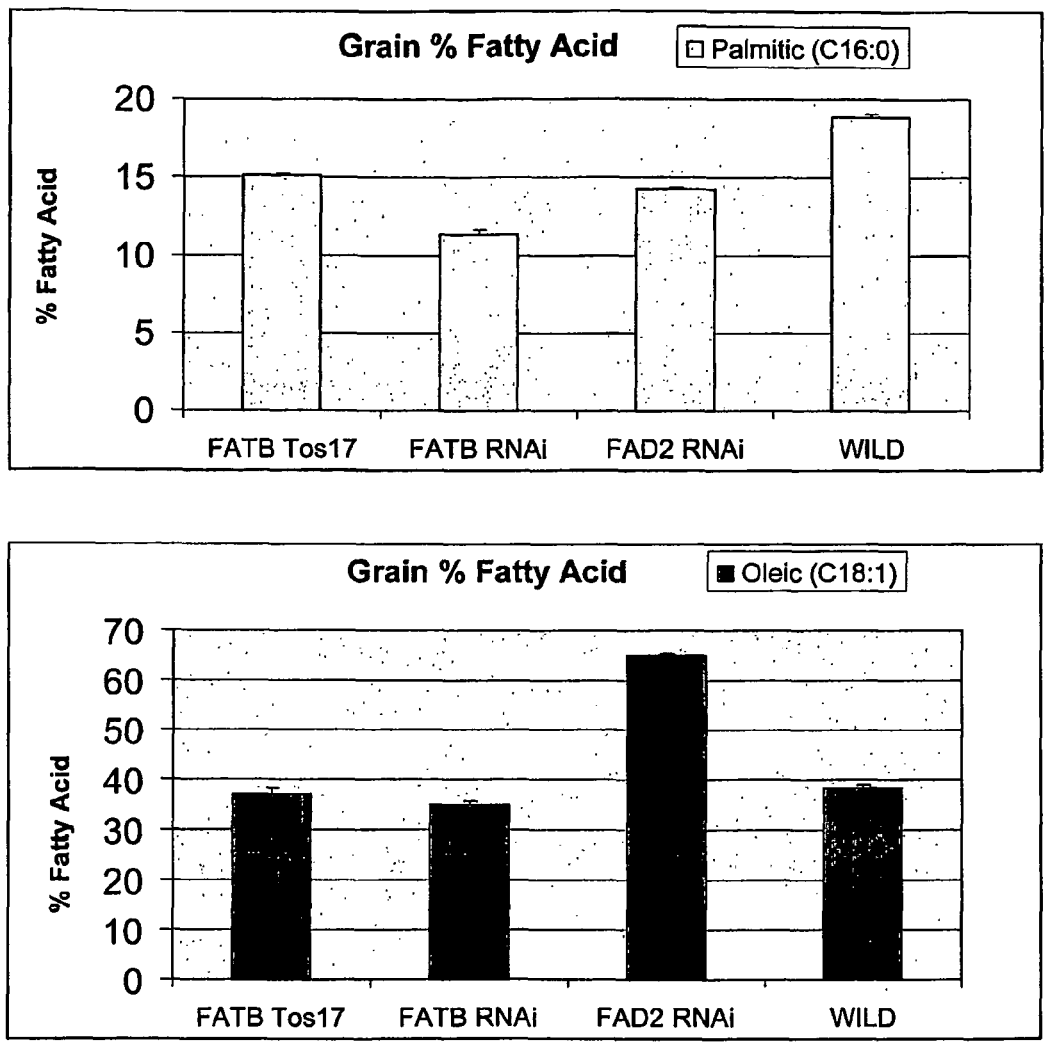

FIG. 12—Graphical representation of the relative percentages of palmitic and oleic acid in a GC total lipid analysis from grains of the genotypes indicated.

Figure 13:
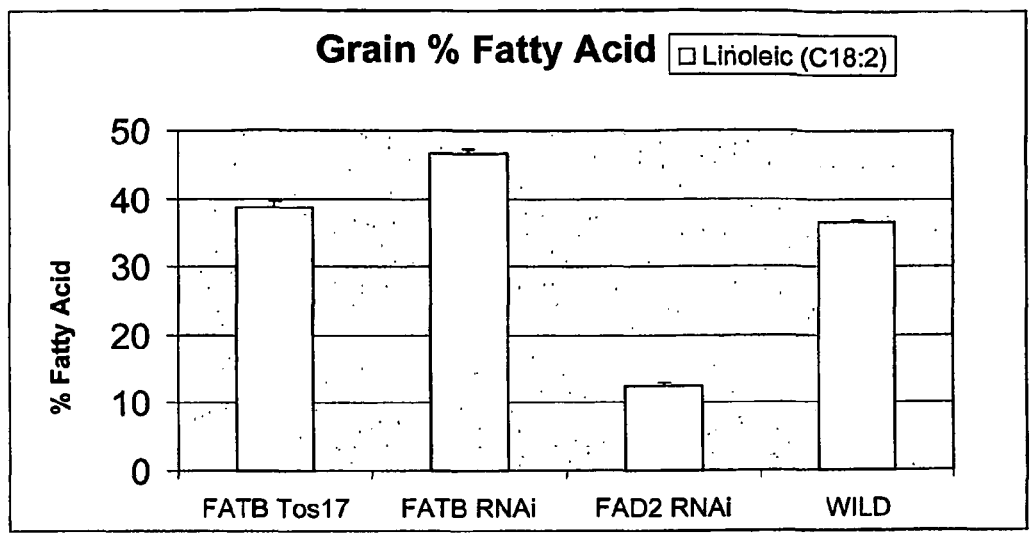

FIG. 13—Graphical representation of the relative percentages of linoleic and oleic acid in a GC total lipid analysis from grains of the genotypes indicated.

Figure 14:
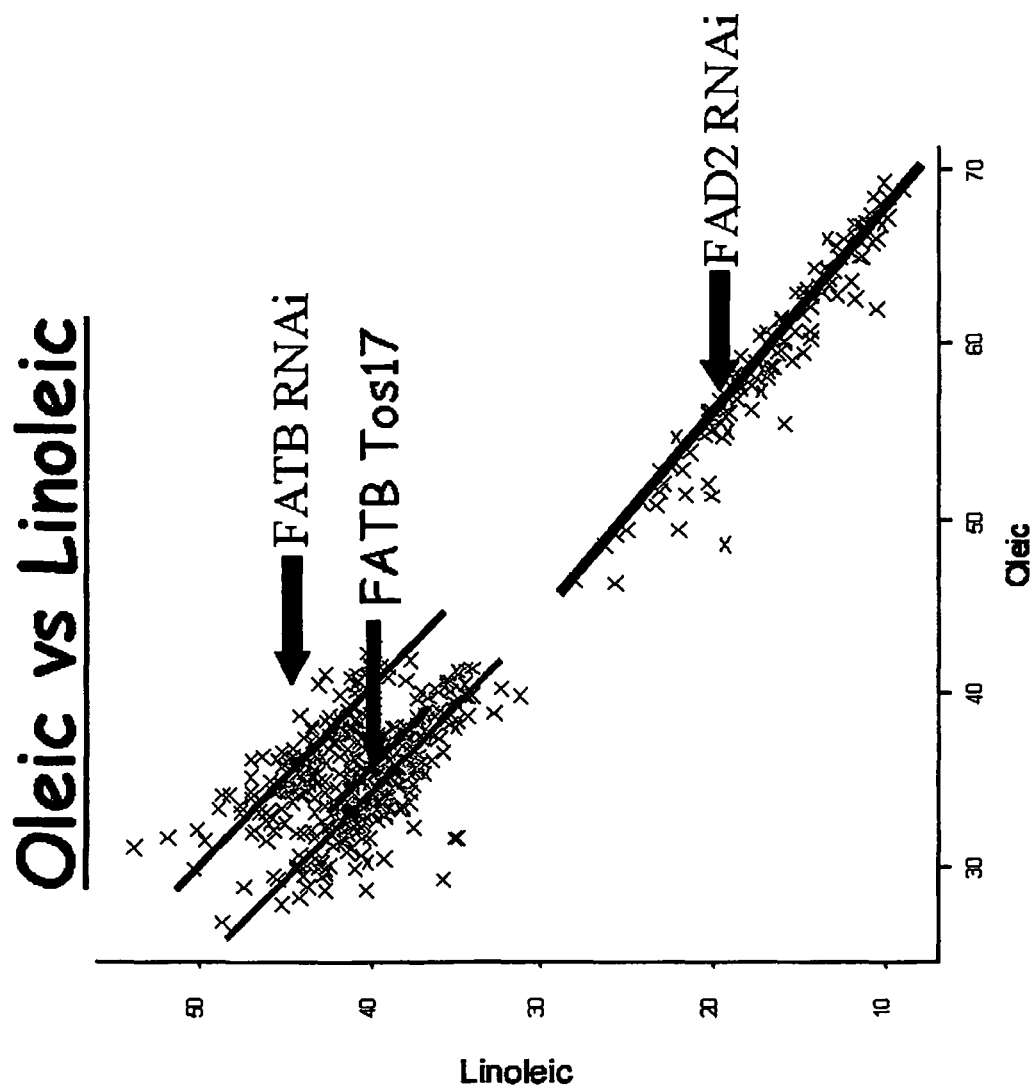

FIG. 14—Scatterplot showing the percentage of linoleic versus oleic acid in the grain of rice plants of the indicated genotypes. Note that the relationship (reflected in the slope of the line) between the amounts of these two fatty acids is essentially the same in all of the lines analysed but the pool size capacity appears to be different (as reflected in the displacements of the different lines along the space analysed.

Figure 15:
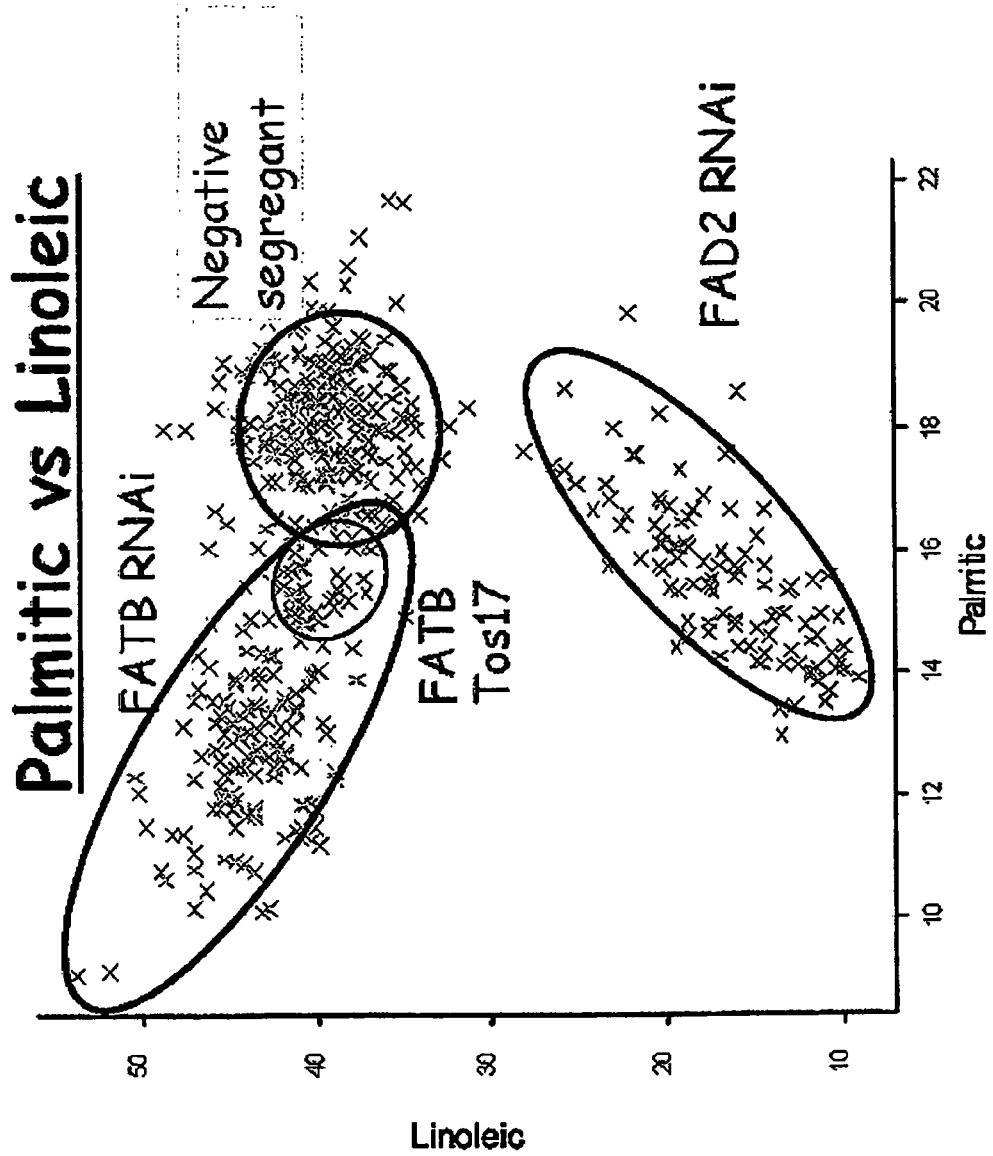

FIG. 15—Scatterplot of the percentage of linoleic versus palmitic acid among different genotypes. Note the different slopes of the lines affected in FatB compared to those affected in Fad2. This suggests the relationship between these components is different in the different genotypes, probably reflecting the differences in the steps affected.

Figure 16:
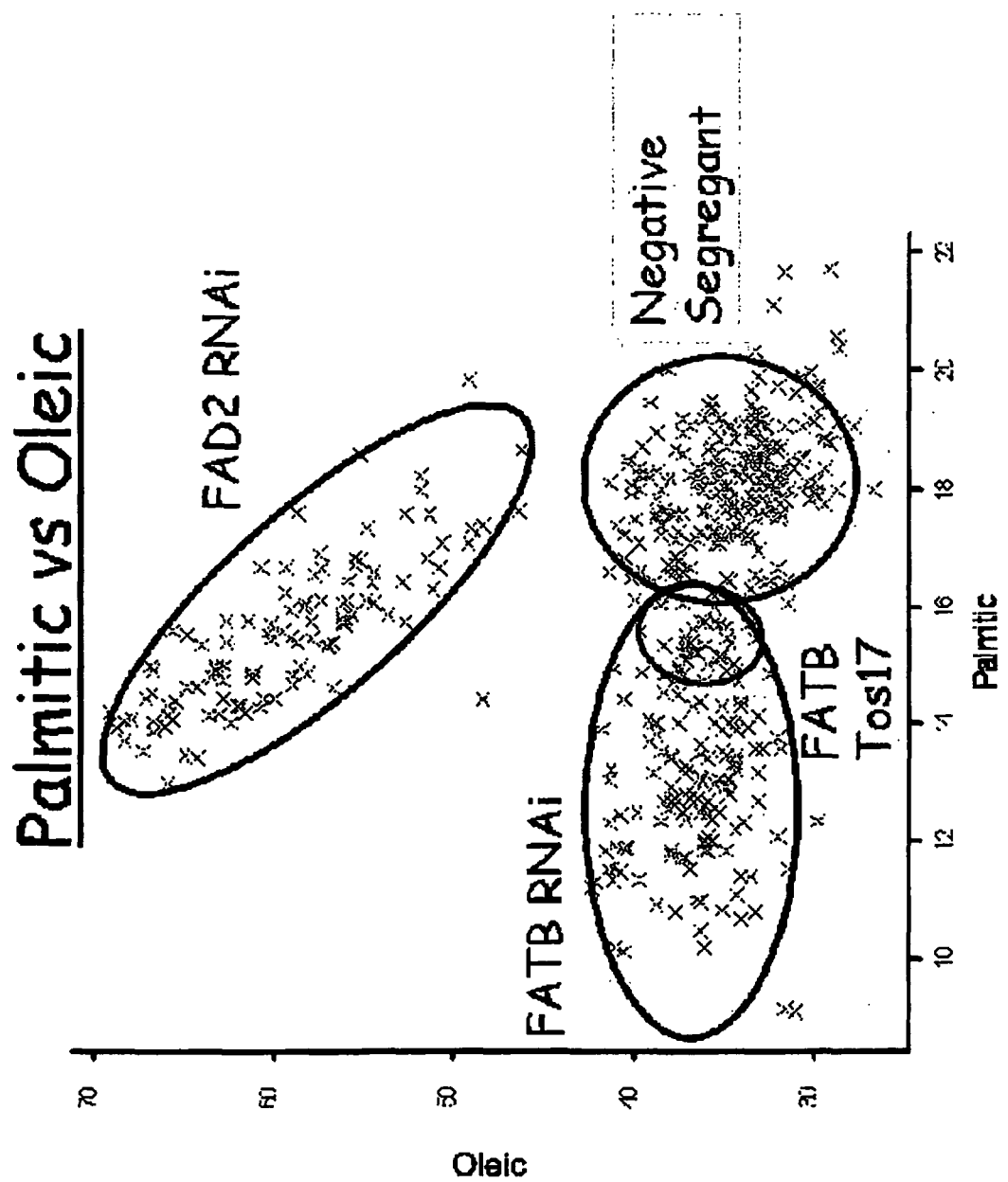

FIG. 16—Scatterplot of the percentage of oleic versus palmitic acid for various genotypes. Note the differences in slopes.

Figure 17:
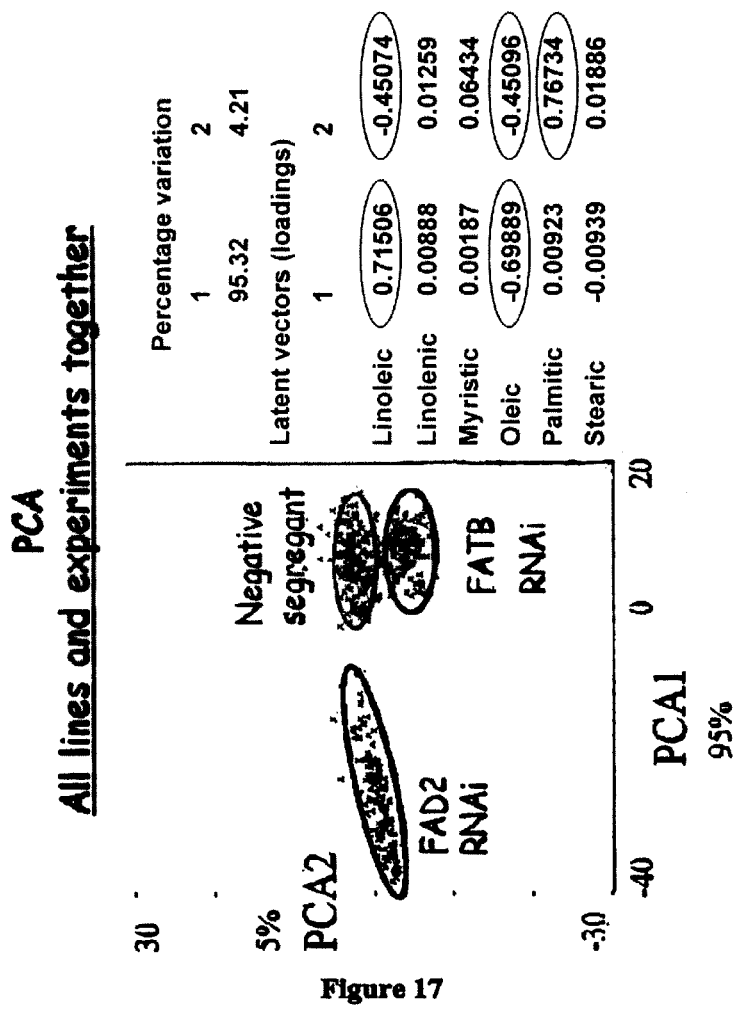

FIG. 17—Graphical representation of Principal Component Analysis of variation in oil composition for Fad2 RNAi plants and FatB RNAi plants. The results show that Principal Component 2 is Linoleic versus Oleic and Principal Component 2 is Palmitic versus Linoleic plus Oleic.

Figure 18:
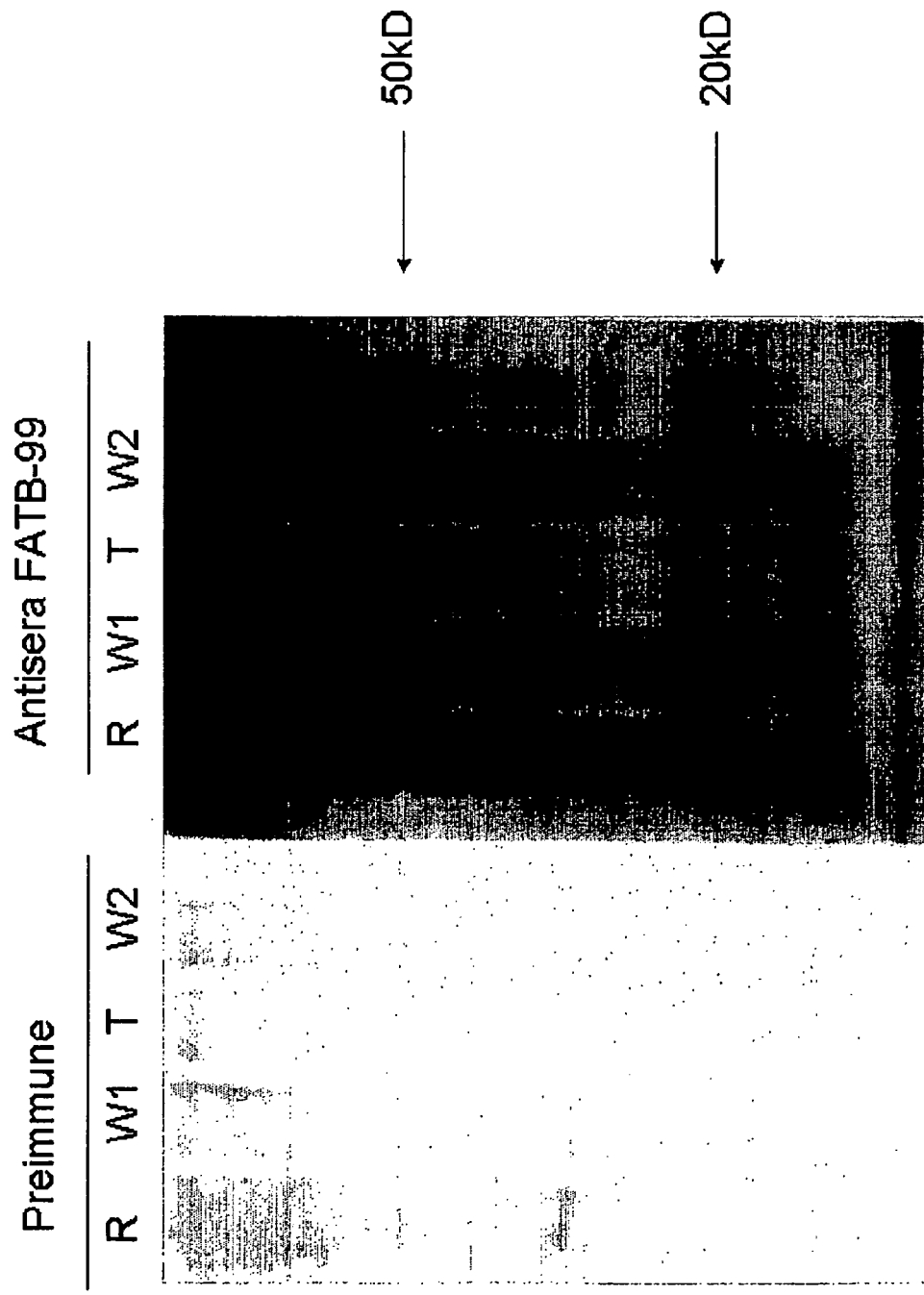

FIG. 18—Western blot showing the reaction of antisera raised against peptide. FatB-99 against total leaf protein extracts analysed by SDS-PAGE. A peptide of approx 20 kDa is missing in the Tos-17 line. The reaction with preimmune sera is indicated. R refers to FatB RNAi lines and T is the Tos-17 line. W1 and W2 are wildtype.

KEY TO SEQUENCE LISTING

SEQ ID NO:1—Rice FatB2 protein.
SEQ ID NO:2—Rice FatB3 protein.
SEQ ID NO:3—Rice FatB1 protein.
SEQ ID NO:4—Rice FatB4 protein.
SEQ ID NO:5—Rice FatB3 gene.
SEQ ID NO:6—Rice FatB2 gene.
SEQ ID NO:7—Rice FatB1 gene.
SEQ ID NO:8—Rice FatB4 gene.
SEQ ID NO:9—cDNA encoding rice FatB1 protein.
SEQ ID NO:10—Gene encoding rice FatB1 protein partial sequence only, see FIG. 5—includes all exon sequences and some flanking and intron sequence).
SEQ ID NO:11—Open reading frame encoding rice FatB2 protein.
SEQ ID NO:12—Open reading frame encoding rice FatB3 protein.
SEQ ID NO:13—Open reading frame encoding rice FatB1 protein.
SEQ ID NO:14—Open reading frame encoding rice FatB4 protein.
SEQ ID NO:15—Rice Fad2 isoform 1.
SEQ ID NO:16—Rice Fad2 isoform 3.
SEQ ID NO:17—Rice Fad2 isoform 2.
SEQ ID NO:18—Rice Fad2 isoform 4.
SEQ ID NO:19—Rice Fad2-3 cDNA.
SEQ ID NO:20—Rice Fad2-1 cDNA.
SEQ ID NO:21—Rice Fad2-2 cDNA.
SEQ ID NO:22—Open reading frame encoding rice Fad2-2.
SEQ ID NO:23—Open reading frame encoding rice Fad2-4.
SEQ ID NO:24—Open reading frame encoding rice Fad2-1.
SEQ ID NO:25—Open reading frame encoding rice Fad2-3.
SEQ ID NO:26—FatB consensus sequence.
SEQ ID NOs 27 to 33—Fad2 consensus sequences.
SEQ ID NOs 34 to 55 and 60 to 63—Oligonucleotide primers.
SEQ ID NOs 56 to 59—Antigenic rice FatB peptides.
SEQ ID NOs 64 to 83—Sequence of one strand of molecules that can be used for RNAi.

DETAILED DESCRIPTION OF THE INVENTION

General Techniques

Unless specifically defined otherwise, all technical and scientific terms used herein shall be taken to have the same meaning as commonly understood by one of ordinary skill in the art (e.g., in cell culture, plant molecular biology, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

SELECTED DEFINITIONS

As used herein, the term "Fad2 polypeptide" refers to a protein which performs a desaturase reaction converting oleic acid to linoleic acid. Thus, the term "Fad2 activity" refers to the conversion of oleic acid to linoleic acid. These fatty acids may be in an esterified form, such as, for example, as part of a phospholipid. Examples of rice Fad2 polypeptides include proteins comprising an amino acid sequence provided in FIG. 7 and SEQ ID NOs 15 to 18, as well as variants and/or mutants thereof. Such variants and/or mutants may be at least 80% identical, more preferably at least 90% identical, more preferably at least 95% identical, and even more preferably at least 99% identical to any one of the polypeptides provided in FIG. 7 and SEQ ID NOs 15 to 18.

A "Fad2 polynucleotide" or "Fad2 gene" encodes a Fad2 polypeptide. Examples of Fad2 polynucleotides include nucleic acids comprising a nucleotide sequence provided in FIG. 8 or 10 and SEQ ID NOs 19 to 25, as well as allelic variants and/or mutants thereof. Examples of Fad2 genes include nucleic acids comprising a nucleotide sequence provided in FIG. 8 and SEQ ID NOs 19 to 21, as well as allelic variants and/or mutants thereof. Such allelic variants and/or mutants may be at least 80% identical, more preferably at least 90% identical, more preferably at least 95% identical, and even more preferably at least 99% identical to any one of the polynucleotides provided in FIGS. 8 and/or 10, and/or SEQ ID NOs 19 to 25.

As used herein, the term "FatB polypeptide" refers to a protein which hydrolyses palmitoyl-ACP to produce free palmitic acid. Thus, the term "FatB activity" refers to the hydrolysis of palmitoyl-ACP to produce free palmitic acid. Examples of rice FatB polypeptides include proteins comprising an amino acid sequence provided FIG. 2 SEQ ID NOs 1 to 4, as well as variants and/or mutants thereof. Such variants and/or mutants may be at least 80% identical, more preferably at least 90% identical, more preferably at least 95% identical, and even more preferably at least 99% identical to any one of the polypeptides provided in FIG. 2 and SEQ ID NOs 1 to 4.

A "FatB polynucleotide" or "FatB gene" encodes a FatB polypeptide. Examples of FatB polynucleotides include nucleic acids comprising a nucleotide sequence provided in FIGS. 4 and 6 and SEQ ID NOs 5 to 8 and 11 to 14, as well as allelic variants and/or mutants thereof. Examples of FatB genes include nucleic acids comprising a nucleotide sequence provided in FIG. 4 and SEQ ID NOs 5 to 8, as well as allelic variants and/or mutants thereof. Such allelic variants and/or mutants may be at least 80% identical, more preferably at least 90% identical, more preferably at least 95% identical, and even more preferably at least 99% identical to any one of the polynucleotides provided in FIGS. 4 and/or 6, and/or SEQ ID NOs 5 to 8 and 11 to 14.

As used herein, the term "rice" refers to any species of the Genus *Oryza*, including progenitors thereof, as well as progeny thereof produced by crosses with other species. It is preferred that the plant is of a *Oryza* species which is commercially cultivated such as, for example, a strain or cultivar or variety of *Oryza sativa* or suitable for commercial production of grain.

As used herein, the term "rice oil" refers to a composition obtained from the seed/grain, or a portion thereof such as the bran layer, of a rice plant which comprises at least 60% (w/w) lipid. Rice oil is typically a liquid at room temperature. Preferably, the lipid comprises fatty acids that are at least 6 carbons in length. The fatty acids are typically in an esterified form, such as for example as triacylglycerols, phospholipid. Rice oil of the invention comprises oleic acid. Rice oil of the invention may also comprise at least some other fatty acids such as palmitic acid, linoleic acid, myristic acid, stearic acid and/or linolenic acid. The fatty acids may be free fatty acids and/or be found as triacylglycerols (TAGs). In an embodiment, at least 50%, more preferably at least 70%, more preferably at least 80% of the fatty acids in rice oil of the invention be found as TAGs. Rice oil of the invention can form part of the rice grain/seed or portion thereof such as the aleurone layer or embryo/scutellnum, which together are referred to as "rice bran". Alternatively, rice oil of the invention has been extracted from rice grain/seed or rice bran. An example of such an extraction procedure is provided in Example 1. Thus, in an embodiment, "rice oil" of the invention is "substantially purified" or "purified" rice oil that has been separated from one or more other lipids, nucleic acids, polypeptides, or other contaminating molecules with which it is associated in its native state. It is preferred that the substantially purified rice oil is at least 60% free, more preferably at least 75% free, and more preferably at least 90% free from other components with which it is naturally associated. In a preferred embodiment, upon extraction the ratio of oleic acid to linoleic acid, palmitic acid to oleic acid and/or palmitic acid to linoleic acid has not been significantly altered (for example, no greater than a 5% alteration) when compared to the ratio in the intact seed/grain or bran. In a further embodiment, the rice oil has not been exposed to a procedure, such as hydrogenation, which may alter the ratio of oleic acid to linoleic acid, palmitic acid to oleic acid and/or palmitic acid to linoleic acid when compared to the ratio in the intact seed/grain or bran. Rice oil of the invention may further comprise non-fatty acid molecules such as, but not limited to, γ-oryzanols and sterols.

Rice oil may be extracted from rice seed or bran by any method known in the art. This typically involves extraction with nonpolar solvents such as diethyl ether, petroleum ether, chloroform/methanol or butanol mixtures. Lipids associated with the starch in the grain may be extracted with water-saturated butanol. The rice oil may be "de-gummed" by methods known in the art to remove polysaccharides or treated in other ways to remove contaminants or improve purity, stability or colour. The triacylglycerols and other esters in the oil may be hydrolysed to release free fatty acids, or the oil hydrogenated or treated chemically or enzymatically as known in the art.

Rice oil after extraction from rice seed or bran typically comprises the group of lipids called γ-oryzanols. As used herein, "comprises γ-oryzanol" refers to the presence of at least 0.1% (w/w) γ-oryzanol compounds in the oil. The levels of γ-oryzanol in rice oil after extraction and before removal from the TAG is typically 1.5-3.5% (w/w). The compounds are typically a mixture of steryl and other triterpenyl esters of ferulic acid (4-hydroxy-3-methoxy cinnamic acid). Cycloartenyl ferulate, 24-methylene cycloartanyl ferulate and campesteryl ferulate are the predominant ferulates in oryzanol, with lower levels of β-sitosteryl ferulate and stigmasteryl ferulate. The presence of γ-oryzanols is thought to help protect consumers of rice oil against chronic diseases such as heart disease and cancer and therefore the presence of γ-oryzanol is advantageous.

As used herein, the term "rice bran" refers to the layer (aleurone layer) between the inner white rice grain and the outer hull of a rice seed/grain as well as the embryo/scutellum of the grain. The rice bran is the primary by product of the polishing of brown rice to produce white rice.

As used herein, the term "increased storage life" refers to a method of the invention producing a seed/grain, which upon harvesting, can be stored as brown rice for an enhanced period of time when compared to, for example, brown rice harvested from a wild type (non-genetically modified) rice plant As described herein, one measure for "increased storage life" of brown rice is hexanal production following storage for at least 8 weeks at 40° C. (see Example 8).

The term "plant" includes whole plants, vegetative structures (for example, leaves, stems), roots, floral organs/structures, seed (including embryo, endosperm, and seed coat), plant tissue (for example, vascular tissue, ground tissue, and the like), cells and progeny of the same.

A "transgenic plant", "genetically modified plant" or variations thereof refers to a plant that contains a gene construct ("transgene") not found in a wild-type plant of the same species, variety or cultivar. A "transgene" as referred to herein has the normal meaning in the art of biotechnology and includes a genetic sequence which has been produced or altered by recombinant DNA or RNA technology and which has been introduced into the plant cell. The transgene may include genetic sequences derived from a plant cell. Typically, the transgene has been introduced into the plant by human manipulation such as, for example, by transformation but any method can be used as one of skill in the art recognizes.

The terms "seed" and "grain" are used interchangeably herein. "Grain" generally refers to mature, harvested grain but can also refer to grain after imbibition or germination, according to the context. Mature grain commonly has a moisture content of less than about 18-20%.

As used herein, the term "corresponding non-modified plant" refers to a wild-type plant. "Wild type", as used herein, refers to a cell, tissue or plant that has not been modified according to the invention. Wild-type cells, tissue or plants may be used as controls to compare levels of expression of an exogenous nucleic acid or the extent and nature of trait modification with cells, tissue or plants modified as described herein. Wild-type rice varieties that are suitable as a reference standard include Nipponbare.

"Nucleic acid molecule" refers to a oligonucleotide, polynucleotide or any fragment thereof. It may be DNA or RNA of genomic or synthetic origin, double-stranded or single-stranded, and combined with carbohydrate, lipids, protein, or other materials to perform a particular activity defined herein. The terms "nucleic acid molecule" and "polynucleotide" are used herein interchangeably.

The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

"Oligonucleotides" can be RNA, DNA, or derivatives of either. Although the terms polynucleotide and oligonucleotide have overlapping meaning, oligonucleotide are typically relatively short single stranded molecules. The minimum size of such oligonucleotides is the size required for the formation of a stable hybrid between an oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length.

As used herein, the term "nucleic acid amplification" refers to any in vitro method for increasing the number of copies of a nucleic acid molecule with the use of a DNA polymerase. Nucleic acid amplification results in the incorporation of nucleotides into a DNA molecule or primer thereby forming a new DNA molecule complementary to a DNA template. The newly formed DNA molecule can be used a template to synthesize additional DNA molecules.

"Operably linked" as used herein refers to a functional relationship between two or more nucleic acid (e.g., DNA) segments. Typically, it refers to the functional relationship of transcriptional regulatory element (promoter) to a transcribed sequence. For example, a promoter is operably linked to a coding sequence, such as a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

As used herein, the term "gene" is to be taken in its broadest context and includes the deoxyribonucleotide sequences comprising the protein coding region of a structural gene and including sequences located adjacent to the coding region on both the 5' and 3' ends for a distance of at least about 2 kb on either end and which are involved in expression of the gene. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

As used herein, the term "genetically linked" or similar refers to a marker locus and a second locus being sufficiently close on a chromosome that they will be inherited together in more than 50% of meioses, e.g., not randomly. This definition includes the situation where the marker locus and second locus form part of the same gene. Furthermore, this definition includes the embodiment where the marker locus comprises a polymorphism that is responsible for the trait of interest (in other words the marker locus is directly "linked" or "perfectly linked" to the phenotype). In another embodiment, the marker locus and a second locus are different, yet sufficiently close on a chromosome that they will be inherited together in more than 50% of meioses. The percent of recombination observed between genetically linked loci per generation (centimorgans (cM)), will be less than 50. In particular embodiments of the invention, genetically linked loci may be 45, 35, 25, 15, 10, 5, 4, 3, 2, or 1 or less cM apart on a chromosome. Preferably, the markers are less than 5 cM apart and most preferably about 0 cM apart.

An "allele" refers to one specific form of a genetic sequence (such as a gene) within a cell, an individual plant or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations".

A "polymorphism" as used herein denotes a variation in the nucleotide sequence between alleles of the loci of the invention, of different species, cultivars, strains or individuals of a plant. A "polymorphic position" is a preselected nucleotide position within the sequence of the gene. In some cases, genetic polymorphisms are reflected by an amino acid sequence variation, and thus a polymorphic position can result in location of a polymorphism in the amino acid sequence at a predetermined position in the sequence of a polypeptide. In other instances, the polymorphic region may be in a non-polypeptide encoding region of the gene, for example in the promoter region such may influence expression levels of the gene. Typical polymorphisms are deletions, insertions or substitutions. These can involve a single nucleotide (single nucleotide polymorphism or SNP) or two or more nucleotides.

The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, modifications, analogous and/or derivatives of the polypeptides of the invention as described herein.

The % identity of a polypeptide is determined by GAP (Needleman and Wunsch, 1970) analysis (GCG program) with a gap creation penalty=5, and a gap extension penalty=0.3. The query sequence is at least 25 amino acids in length, and the GAP analysis aligns the two sequences over a region of at least 25 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

Antisense Polynucleotides

The term "antisense polynucleotide" shall be taken to mean a DNA or RNA, or combination thereof, molecule that is complementary to at least a portion of a specific mRNA molecule encoding a FatB or Fad2 polypeptide and capable of interfering with a post-transcriptional event such as mRNA translation. The use of antisense methods is well known in the art (see for example, G. Hartmann and S. Endres, Manual of Antisense Methodology, Kluwer (1999)). The use of antisense techniques in plants has been reviewed by Bourque, 1995 and Senior, 1998. Bourque, 1995 lists a large number of examples of how antisense sequences have been utilized in plant systems as a method of gene inactivation. She also states that attaining 100% inhibition of any enzyme activity may not be necessary as partial inhibition will more than likely result in measurable change in the system. Senior (1998) states that antisense methods are now a very well established technique for manipulating gene expression.

An antisense polynucleotide of the invention will hybridize to a target polynucleotide under physiological conditions. As used herein, the term "an antisense polynucleotide which hybridises under physiological conditions" means that the polynucleotide (which is fully or partially single stranded) is at least capable of forming a double stranded polynucleotide with mRNA encoding a protein, such as those provided in FIG. 2 or 7 or SEQ ID NOs 1 to 4 or 15 to 18 under normal conditions in a cell, preferably a rice cell.

Antisense molecules may include sequences that correspond to the structural genes or for sequences that effect control over the gene expression or splicing event. For example, the antisense sequence may correspond to the targeted coding region of the genes of the invention, or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition.

The length of the antisense sequence should be at least 19 contiguous nucleotides, preferably at least 50 nucleotides, and more preferably at least 100, 200, 500 or 1000 nucleotides. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences which may function to stabilize the molecule.

Catalytic Polynucleotides

The term catalytic polynucleotide/nucleic acid refers to a DNA molecule or DNA-containing molecule (also known in the art as a "deoxyribozyme") or an RNA or RNA-containing molecule (also known as a "ribozyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are particularly useful in this invention are the hammerhead ribozyme (Haseloff and Gerlach, 1988; Perriman et al., 1992) and the hairpin ribozyme (Shippy et al., 1999).

The ribozymes of this invention and DNA encoding the ribozymes can be chemically synthesized using methods well known in the art. The ribozymes can also be prepared from a DNA molecule (that upon transcription, yields an RNA molecule) operably linked to an RNA polymerase promoter, e.g., the promoter for T7 RNA polymerase or SP6 RNA polymerase. Accordingly, also provided by this invention is a nucleic acid molecule, i.e., DNA or cDNA, coding for a catalytic polynucleotide of the invention. When the vector also contains an RNA polymerase promoter operably linked to the DNA molecule, the ribozyme can be produced in vitro upon incubation with RNA polymerase and nucleotides. In a separate embodiment, the DNA can be inserted into an expression cassette or transcription cassette. After synthesis, the RNA molecule can be modified by ligation to a DNA molecule having the ability to stabilize the ribozyme and make it resistant to RNase.

As with antisense polynucleotides described herein, catalytic polynucleotides of the invention should also be capable of hybridizing a target nucleic acid molecule (for example an mRNA encoding any polypeptide provided in FIG. 2 or 7 or SEQ ID NOs 1 to 4 or 15 to 18) under "physiological conditions", namely those conditions within a cell (especially conditions in a plant cell such as a rice cell).

RNA Interference

RNA interference (RNAi) is particularly useful for specifically inhibiting the production of a particular protein. Although not wishing to be limited by theory, Waterhouse et al. (1998) have provided a model for the mechanism by which dsRNA (duplex RNA) can be used to reduce protein production. This technology relies on the presence of dsRNA molecules that contain a sequence that is essentially identical to the mRNA of the gene of interest or part thereof, in this case an mRNA encoding a polypeptide according to the invention. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present invention is well within the capacity of a person skilled in the art, particularly considering Waterhouse et al. (1998), Smith et al. (2000), WO 99/32619, WO 99/53050, WO 99/49029, and WO 01/34815.

In one example, a DNA is introduced that directs the synthesis of an at least partly double stranded RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule is thought to trigger a response from an endogenous plant system that destroys both the double stranded RNA and also the homologous RNA transcript from the target plant gene, efficiently reducing or eliminating the activity of the target gene.

The length of the sense and antisense sequences that hybridise should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

Preferred small interfering RNA ('siRNA') molecules comprise a nucleotide sequence that is identical to about 19-21 contiguous nucleotides of the target mRNA. Preferably, the target mRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the plant (preferably rice) in which it is to be introduced, e.g., as determined by standard BLAST search.

Examples of dsRNA molecules of the invention are provided in Example 5. Further examples include those which comprise a sequence as provided in one or more of SEQ ID NOs 64 to 73 (for Fad2) and SEQ ID NOs 74 to 83 (for FatB).

MicroRNA

MicroRNA regulation is a clearly specialized branch of the RNA silencing pathway that evolved towards gene regulation, diverging from conventional RNAi/PTGS. MicroRNAs are a specific class of small RNAs that are encoded in gene-like elements organized in a characteristic inverted repeat. When transcribed, microRNA genes give rise to stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression (see, for example, Millar and Waterhouse, 2005; Pasquinelli et al., 2005; Almeida and Allshire, 2005).

Cosuppression

Another molecular biological approach that may be used is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the sense orientation with respect to a promoter for its expression. The size of the sense fragment, its correspondence to target gene regions, and its degree of sequence identity to the target gene are as for the antisense sequences described above. In some instances the additional copy of the gene sequence interferes with the expression of the target plant gene. Reference is made to WO 97/20936 and EP 0465572 for methods of implementing co-suppression approaches.

Nucleic Acid Hybridization

In an embodiment, polynucleotides of the invention, or a strand thereof, hybridize under physiological conditions to a polynucleotide comprising any one or more of the sequence of nucleotides provided as SEQ ID NOs 5 to 8, 11 to 14 or 19 to 25. In a further embodiment, polynucleotides of the invention, or a strand thereof, also hybridize to a polynucleotide comprising any one or more of the sequence of nucleotides provided as SEQ ID NOs 5 to 8, 11 to 14 or 19 to 25 under stringent conditions.

As used herein, the phrase "stringent conditions" refers to conditions under which a polynucleotide, probe, primer and/or oligonucleotide will hybridize to its target sequence(s), but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel et al. (supra), Current Protocols In Molecular Biology, John Wiley & Sons, N.Y. (1989), 6.3.1-6.3.6, as well as the Examples described herein. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2.×SSC, 0.01% BSA at 50° C. In another embodiment, a nucleic acid sequence that is hybridizable to the nucleic acid molecule comprising the nucleotide sequence of SEQ ID NOs 5 to 8, 11 to 14 or 19 to 25, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known within the art, see, e.g., Ausubel et al. (supra), and Kriegler, 1990; Gene Transfer And Expression, A Laboratory Manual, Stockton Press, NY. In yet another embodiment, a nucleic acid that is hybridizable to the nucleic acid molecule comprising the nucleotide sequences SEQ ID NOs 5 to 8, 11 to 14 or 19 to 25, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art, see, e.g., Ausubel et al. (supra) and Kriegler, 1990, Gene Transfer And Expression, A Laboratory Manual, Stockton Press, NY, as well as the Examples provided herein.

Nucleic Acid Constructs, Vectors and Host Cells

The present invention includes the production of genetically modified rice plants, wherein the plant has decreased expression of a polypeptide having Fad2 and/or FatB activity relative to a corresponding non-modified plant.

Nucleic acid constructs useful for producing the above-mentioned transgenic plants can readily be produced using standard techniques.

When inserting a region encoding an mRNA the construct may comprise intron sequences. These intron sequences may aid expression of the transgene in the plant. The term "intron" is used in its normal sense as meaning a genetic segment that is transcribed but does not encode protein and which is spliced out of an RNA before translation. Introns may be incorporated in a 5'-UTR or a coding region if the transgene encodes a translated product, or anywhere in the transcribed region if it does not. However, in a preferred embodiment, any polypeptide encoding region is provided as a single open reading frame. As the skilled addressee would be aware, such open reading frames can be obtained by reverse transcribing mRNA encoding the polypeptide.

To ensure appropriate expression of the gene encoding an mRNA of interest, the nucleic acid construct typically comprises one or more regulatory elements such as promoters, enhancers, as well as transcription termination or polyadenylation sequences. Such elements are well known in the art.

The transcriptional initiation region comprising the regulatory element(s) may provide for regulated or constitutive expression in the plant Preferably, expression at least occurs in cells of the embryo, endosperm, bran layer developing seed and/or mature seed (grain). In an alternate embodiment, the regulatory elements may be promoters not specific for seed cells (such as ubiquitin promoter or CaMV35S or enhanced 35S promoters).

Examples of seed specific promoters useful for the present invention include, but are not limited to, the wheat low molecular weight glutenin promoter (Colot et al., 1987), the promoter expressing α-amylase in wheat seeds (Stefanov et al., 1991), and the hordein promoter (Brandt et al., 1985).

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, the sugarcane bacilliform virus promoter, the commelina yellow mottle virus promoter, the light-inducible promoter from the small subunit of the ribulose-1,5-bis-phosphate carboxylase, the rice cytosolic triose-phosphate isomerase promoter, the adenine phosphoribosyl-transferase promoter of *Arabidopsis*, the rice actin 1 gene promoter, the mannopine synthase and octopine synthase promoters, the Adh promoter, the sucrose synthase promoter, the R gene complex promoter, and the chlorophyll α/β binding protein gene promoter. These promoters have been used to create DNA vectors that have been expressed in plants; see, e.g., PCT publication WO 8402913. All of these promoters have been used to create various types of plant-expressible recombinant DNA vectors.

The promoter may be modulated by factors such as temperature, light or stress. Ordinarily, the regulatory elements will be provided 5' of the genetic sequence to be expressed. The construct may also contain other elements that enhance transcription such as the nos 3' or the ocs 3' polyadenylation regions or transcription terminators.

The 5' non-translated leader sequence can be derived from the promoter selected to express the heterologous gene sequence of the polynucleotide of the present invention, and can be specifically modified if desired so as to increase translation of mRNA. For a review of optimizing expression of transgenes, see Koziel et al. (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention is not limited to constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader U.S. Pat. No. 5,362,865 and U.S. Pat. No. 5,859,347), and the TMV omega element.

The termination of transcription is accomplished by a 3' non-translated DNA sequence operably linked in the chimeric vector to the polynucleotide of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' intranslated region, the 3' untranslated region from pea small subunit Rubisco gene, the 3' untranslated region from soybean 7S seed storage protein gene are commonly used in this capacity. The 3' transcribed, non-translated regions containing the polyadenylate signal of *Agrobacterium* tumor-inducing (Ti) plasmid genes are also suitable.

Typically, the nucleic acid construct comprises a selectable marker. Selectable markers aid in the identification and screening of plants or cells that have been transformed with the exogenous nucleic acid molecule. The selectable marker gene may provide antibiotic or herbicide resistance to the rice cells, or allow the utilization of substrates such as mannose. The selectable marker preferably confers hygromycin resistance to the rice cells.

Preferably, the nucleic acid construct is stably incorporated into the genome of the plant. Accordingly, the nucleic acid comprises appropriate elements which allow the molecule to be incorporated into the genome, or the construct is placed in an appropriate vector which can be incorporated into a chromosome of a plant cell.

One embodiment of the present invention includes a recombinant vector, which includes at least one polynucleotide molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

A number of vectors suitable for stable transfection of plant cells or for the establishment of transgenic plants have been described in, e.g., Pouwels et al. Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred host cells are plant cells, more preferably cells of a cereal plant, and even more preferably a rice cell.

Transgenic Plants

Transgenic rice (also referred to herein as genetically modified rice) can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

In a preferred embodiment, the transgenic plants are homozygous for each and every polynucleotide that has been introduced (transgene) so that their progeny do not segregate for the desired phenotype. The transgenic plants may also be heterozygous for the introduced transgene(s), such as, for example, in F1 progeny which have been grown from hybrid seed. Such plants may provide advantages such as hybrid vigour, well known in the art.

Four general methods for direct delivery of a gene into cells have been described: (1) chemical methods (Graham et al., 1973); (2) physical methods such as microinjection (Capecchi, 1980); electroporation (see, for example, WO 87/06614, U.S. Pat. No. 5,472,869, 5,384,253, WO 92/09696 and WO 93/21335; and the gene gun (see, for example, U.S. Pat. No. 4,945,050 and U.S. Pat. No. 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. An illustrative embodiment of a method for delivering DNA into *Zea mays* cells by acceleration is a biolistics α-particle delivery system, that can be used to propel particles coated with DNA through a screen, such as a stainless steel or Nytex screen, onto a filter surface covered with corn cells cultured in suspension. A particle delivery system suitable for use with the present invention is the helium acceleration PDS-1000/He gun is available from Bio-Rad Laboratories.

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus that express the exogenous gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Method disclosed for plastid transformation in higher plants include particle gun delivery of DNA containing a selectable marker and targeting of the DNA to the plastid genome through homologous recombination (U.S. Pat. No. 5,451,513, U.S. Pat. No. 5,545,818, U.S. Pat. No. 5,877,402, U.S. Pat. No. 5,932,479, and WO 99/05265.

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions that influence the physiological state of the recipient cells and that may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art (see, for example, U.S. Pat. No. 5,177,010, U.S. Pat. No. 5,104,310, U.S. Pat. No. 5,004,863, U.S. Pat. No. 5,159,135). Further, the integration of the T-DNA is a relatively precise process resulting in few rearrangements. The region of DNA to be transferred is defined by the border sequences, and intervening DNA is usually inserted into the plant genome.

Modern *Agrobacterium* transformation vectors are capable of replication in *E. coli* as well as *Agrobacterium*, allowing for convenient manipulations as described (Klee et al., In: Plant DNA Infectious Agents, Hohn and Schell, eds., Springer-Verlag, New York, pp. 179-203 (1985). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant varieties where *Agrobacterium*-mediated transformation is efficient, it is the method of choice because of the facile and defined nature of the gene transfer.

A transgenic plant formed using *Agrobacterium* transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, In: Breeding Methods for Cultivar Development, Wilcox J. ed., American Society of Agronomy, Madison Wis. (1987).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transformation of cereal plants such as rice for introducing genetic variation into the plant by introduction of an exogenous nucleic acid and for regeneration of plants from protoplasts or immature plant embryos are well known in the art, see for example, Canadian Patent Application No. 2,092, 588, Australian Patent Application No 61781/94, Australian Patent No 667939, U.S. Pat. No. 6,100,447, International Patent Application PCT/US97/10621, U.S. Pat. No. 5,589, 617, U.S. Pat. No. 6,541,257, and other methods are set out in Patent specification WO99/14314. Preferably, transgenic rice plants are produced by *Agrobacterium tumefaciens* mediated transformation procedures. An example of *Agrobacterium* mediated transformation of rice is provided herein in Example 5. Vectors carrying the desired nucleic acid construct may be introduced into regenerable rice cells of tissue cultured plants or explants, or suitable plant systems such as protoplasts.

The regenerable rice cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Marker Assisted Selection

Marker assisted selection is a well recognised method of selecting for heterozygous plants required when backcrossing with a recurrent parent in a classical breeding program. The population of plants in each backcross generation will be heterozygous for the gene of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants. To further speed up the backcrossing program, the embryo from immature seeds (25 days post anthesis) may be excised and grown up on nutrient media under sterile conditions, rather than allowing full seed maturity. This process, termed "embryo rescue", used in combination with DNA extraction at the three leaf stage and analysis for the desired genotype allows rapid selection of plants carrying the desired trait, which may be nurtured to maturity in the greenhouse or field for subsequent further backcrossing to the recurrent parent.

Any molecular biological technique known in the art which is capable of detecting a Fad2 or FatB gene can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof (see, for example, Lemieux, 2000; Langridge et al., 2001). The invention also includes the use of molecular marker techniques to detect polymorphisms linked to alleles of (for example) a Fad2 or FatB gene which confer the desired phenotype. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis, as reviewed by Langridge et al. (2001).

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (Ed. M. J. McPherson and S. G Moller (2000) BIOS Scientific Publishers Ltd, Oxford). PCR can be performed on cDNA obtained from reverse transcribing mRNA isolated from plant cells. However, it will generally be easier if PCR is performed on genomic DNA isolated from a plant.

A primer is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al. (supra) and Sambrook et al. (supra). Sequencing can be carried out by any suitable method, for example, dideoxy sequencing, chemical sequencing or variations thereof. Direct sequencing has the advantage of determining variation in any base pair of a particular sequence.

Hybridization based detection systems include, but are not limited to, the TaqMan assay and molecular beacons. The TaqMan assay (U.S. Pat. No. 5,962,233) uses allele specific (ASO) probes with a donor dye on one end and an acceptor dye on the other end such that the dye pair interact via fluorescence resonance energy transfer (FRET). A target sequence is amplified by PCR modified to include the addition of the labeled ASO probe. The PCR conditions are adjusted so that a single nucleotide difference will effect binding of the probe. Due to the 5' nuclease activity of the Taq polymerase enzyme, a perfectly complementary probe is cleaved during PCR while a probe with a single mismatched base is not cleaved. Cleavage of the probe dissociates the donor dye from the quenching acceptor dye, greatly increasing the donor fluorescence.

An alternative to the TaqMan assay is the molecular beacon assay (U.S. Pat. No. 5,925,517). In the molecular beacon assay, the ASO probes contain complementary sequences flanking the target specific species so that a hairpin structure is formed. The loop of the hairpin is complimentary to the target sequence while each arm of the hairpin contains either donor or acceptor dyes. When not hybridized to a donor sequence, the hairpin structure brings the donor and acceptor dye close together thereby extinguishing the donor fluorescence. When hybridized to the specific target sequence, however, the donor and acceptor dyes are separated with an increase in fluorescence of up to 900 fold. Molecular beacons can be used in conjunction with amplification of the target sequence by PCR and provide a method for real time detection of the presence of target sequences or can be used after amplification.

Tilling

Plants of the invention can be produced using the process known as TILLING (Targeting Induced Local Lesions IN Genomes). In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cel I, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique.

TILLING is further described in Slade and Knauf (2005) and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencer software performs a multiple alignment and discovers the base change, which in each case confirmed the gel band.

Ecotilling can be performed more cheaply than full sequencing, the method currently used for most SNP discovery. Plates containing arrayed ecotypic DNA can be screened rather than pools of DNA from mutagenized plants. Because detection is on gels with nearly base pair resolution and background patterns are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

Mutagenesis Procedures

Techniques for generating mutant rice plant lines are known in the art. Examples of mutagens that can be used for generating mutant rice plants include irradiation and chemical mutagenesis. Mutants may also be produced by techniques such as T-DNA insertion and transposon-induced mutagenesis. The mutagenesis procedure may be performed on any parental cell of a rice plant, for example a seed or a parental cell in tissue culture.

Chemical mutagens are classifiable by chemical properties, e.g., alkylating agents, cross-linking agents, etc. Useful chemical mutagens include, but are not limited to, N-ethyl-N-nitrosourea (ENU); N-methyl-N-nitrosourea (MNU); procarbazine hydrochloride; chlorambucil; cyclophosphamide; methyl methanesulfonate (MMS); ethyl methanesulfonate (EMS); diethyl sulfate; acrylamide monomer; triethylene melamine (TEM); melphalan; nitrogen mustard; vincristine; dimethylnitrosamine; N-methyl-N'-nitro-Nitrosoguani-dine (MNNG); 7,12 dimethylbenzanthracene (DMBA); ethylene oxide; hexamethylphosphoramide; and bisulfan.

An example of suitable irradiation to induce mutations is by gamma radiation, such as that supplied by a Cesium 137 source. The gamma radiation preferably is supplied to the plant cells in a dosage of approximately 60 to 200 Krad., and most preferably in a dosage of approximately 60 to 90 Krad.

Plants are typically exposed to a mutagen for a sufficient duration to accomplish the desired genetic modification but insufficient to completely destroy the viability of the cells and their ability to be regenerated into a plant.

Antibodies

Monoclonal or polyclonal antibodies which bind specifically to FatB or Fad2 polypeptides can be useful for some of the methods of the invention.

The term "binds specifically" refers to the ability of the antibody to bind to a FatB or Fad2 polypeptide but not other proteins of rice, especially proteins of rice seeds.

As used herein, the term "epitope" refers to a region of a FatB or Fad2 polypeptide which is bound by the antibody. An epitope can be administered to an animal to generate antibodies against the epitope, however, antibodies useful for the methods described herein preferably specifically bind the epitope region in the context of the entire polypeptide.

If polyclonal antibodies are desired, a selected mammal (e.g., mouse, rabbit, goat, horse, etc.) is immunised with an immunogenic polypeptide such as those provided in FIG. 2 or 7 or SEQ ID NOs 1 to 4 or 15 to 18. Serum from the immunised animal is collected and treated according to known procedures. If serum containing polyclonal antibodies contains antibodies to other antigens, the polyclonal antibodies can be purified by immunoaffinity chromatography. Techniques for producing and processing polyclonal antisera are known in the art. In order that such antibodies may be made, the invention also provides peptides of the invention or fragments thereof haptenised to another peptide for use as immunogens in animals.

Monoclonal antibodies directed against polypeptides of the invention can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

For the purposes of this invention, the term "antibody", unless specified to the contrary, includes fragments of whole antibodies which retain their binding activity for a target antigen. Such fragments include Fv, F(ab') and F(ab')$_2$ fragments, as well as single chain antibodies (scFv). Furthermore, the antibodies and fragments thereof may be humanised antibodies, for example as described in EP-A-239400.

Antibodies may be bound to a solid support and/or packaged into kits in a suitable container along with suitable reagents, controls, instructions and the like.

Preferably, the antibodies are detectably labeled. Exemplary detectable labels that allow for direct measurement of antibody binding include radiolabels, fluorophores, dyes, magnetic beads, chemiluminescers, colloidal particles, and the like. Examples of labels which permit indirect measurement of binding include enzymes where the substrate may provide for a coloured or fluorescent product. Additional exemplary detectable labels include covalently bound enzymes capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Further exemplary detectable labels include biotin, which binds with high affinity to avidin or streptavidin; fluorochromes (e.g., phycobiliproteins, phycoerythrin and allophycocyanins; fluorescein and Texas red), which can be used with a fluorescence activated cell sorter; haptens; and the like. Preferably, the detectable label allows for direct measurement in a plate luminometer, e.g., biotin. Such labeled antibodies can be used in techniques known in the art to detect polypeptides of the invention.

EXAMPLES

Example 1

Materials and Methods

Extraction of Oil with Sodium Methoxide

For fatty acid and other analyses, total lipid was extracted from rice grains as follows unless stated otherwise. In some cases, samples each consisting of a half grain were used for the extraction, with the second half-grain containing the embryo being used for embryo rescue. The technique can also be used with other cereals.

A single developing seed or half-seed was squashed between filter papers and placed in a tube. 2 ml 0.5M sodium methoxide was added, the tube sealed tightly and then incubated at 80° C. for 10 min. After the tube was cooled, 0.1 ml glacial acetic acid was added followed by 2 ml of distilled water and 2 ml of petroleum spirit. The mixtures were vortexed for 10 sec and, after the phases had separated, the upper petroleum layer was transferred to a small test tube. Approximately 1 g of potassium bicarbonate/sodium sulphate mixture was added to the test tubes and the mixture vortexed. The sample solutions were transferred to autosampler vials and stored in a freezer at −20° C. until GC analysis was performed as described by Soutjesdic et al. (2002).

Extraction of Lipids from Tissues with High Water Content (Bligh-Dyer Method)

This method was adapted from Bligh and Dyer (1959). 1.5 ml of $CHCl_3$/MeOH (1:2) was added to a tissue sample in 0.4 ml of buffer and the sample vortexed vigorously. A further 0.5 ml of $CHCl_3$ was added and the sample vortexed again. 0.5 ml of $H_2O$ was added and the sample vortexed again. The tube was centrifuged briefly at 3000 rpm to separate phases; a white precipitate appeared at the interface. The organic (lower) phase was transferred to a new tube and concentrated under vacuum. If acidic lipids were to be extracted, 0.5 ml of 1% $HClO_4$ was added instead of 0.5 ml of $H_2O$. The volumes in the above procedure could be modified as long as the ratios of $CHCl_3$/MeOH/$H_2O$ were maintained.

Preparation of Fatty Acid Methyl Esters (FAME) for Quantitative Determination of Fatty Acid Content To prepare FAME directly from grain, 10-15 seed were weighed accurately and transferred to a glass tube. An internal standard of 10 µl of 1 mg/ml 17:0-methyl ester was added to each seed sample. 0.75 ml 1 N methanolic-HCl (Supelco) was added to each tube which was capped tightly and refluxed at 80° C. for at least 2-3 hrs or overnight. Samples were cooled, 0.5 ml NaCl (0.9% w/v) added followed by 300 µl hexane. The tubes were capped again and vortexed vigorously. The upper hexane phase (200-250 µl) was carefully transferred to an eppendorf tube. The sample was dried down completely under nitrogen. The dried FAME samples were dissolved in 20 µl of hexane and transferred to conical glass inserts in vials for GC analysis.

FA Analysis by Gas Chromatography

Fatty acid methyl esters were prepared by alkaline trans-methylation as follows. Single seed samples were squashed between filter paper disks. The fatty acids in the lipid transferred to the filter paper disks were then methylated in 2 mL of 0.02 M sodium methoxide for 10 minutes at 80° C., followed by cooling for 30 minutes. 0.1 mL of glacial acetic acid was then added, followed in order by 2 mL of distilled water and 2 mL of hexane. After vortexing and phase separation, the upper hexane layer containing the fatty acid methyl esters was transferred to a microvial. Fatty acid methyl esters were analysed by gas-liquid chromatography as previously described (Stoutjesdijk et al., 2002).

Transformation of Rice

Rice (cv. Nipponbare) was transformed as follows.

i) Callus Induction and Culture

Husks were removed from mature grain, which were then soaked in 70% EtOH for 30 sec to remove any outer layer of wax. The cleaned grains were washed 3 times with sterile $H_2O$ and soaked in a solution of 25% bleach (with 2 drops Tween-20 detergent added) for 20 minutes with shaking to surface sterilize them. Under asceptic conditions, the grains were rinsed briefly with 70% EtOH, washed thoroughly with sterile $H_2O$ 8-10 times and plated onto $N_6D$ medium. Plates were sealed with Micropore-tape and incubated under full light at 28° C. Calli were produced after 6-8 weeks and then transferred to NB media They were sealed with paraffin paper and left in the at 28° C. with sub-culturing every 4 weeks onto fresh NB plates. Calli were not used for transformation after more than 5 subcultures.

ii) Transformation

Healthy looking calli were picked from subculture plates and transferred onto fresh NB plates at a density of 25-30 calli/plate. Two days later, a fresh culture was established of the *Agrobacterium* strain containing the construct to be used, and incubated at 28° C. The culture medium was NB medium supplemented with 100 µM acetosyringone. Calli were immersed in a suspension of the cells for 10 minutes. After draining off excess suspension, calli were placed on NB medium supplemented with 100 µM acetosyringone and incubated in the dark at 25° C. for 3 days (co-cultivation). After the co-cultivation step, calli were washed gently three times in a tube with sterile $H_2O$ containing 150 mg/ml Timetin. Calli were blotted dry on filter paper and plated well spaced onto NBCT plates (containing 100 µg/ml kanamycin if a kanamycin selectable marker gene was used or other selection agent as appropriate, 150 µg/ml Timentin and 200 µg/ml Claroforan). The plates were incubated in the dark for 3-4 weeks at 26-28° C. Resistant calli were observed after about 10 days and transferred to NBCT+ selection plates and incubated in the dark for a further 14-21 days. Healthy calli were transferred onto PRCT+selection plates and incubated in the dark for 8-12 days, then transferred onto RCT+selection plates and incubated in fill light at 28° C. for 30 days. After this time, plantlets that had developed were transferred to ½MS medium in tissue culture pots and incubated under light for 10-14 days for further growth before transfer to soil.

iii) Media Composition and Components for Rice Tissue Culture

N6 macro-elements (20×) (g/l): $(NH_4)_2SO_4$, 9.3; $KNO_3$, 56.6; $KH_2PO_4$, 8; $MgSO_4.7H_2O$, 3.7; $CaCl_2.2H_2O$, 3.3.

N6 micro (100×) (mg/100 ml): $MnSO_4.4H_2O$, 440; $ZnSO_4.7H_2O$, 150; $H_3BO_3$, 160; KI, 80.

N6 Vitamins (100×) (mg/100 ml): Glycine, 20; Thiamine-HCl, 10; Pyridoxine-HCl, 5; Nicotinic acid, 5.

B5 micro-elements (100×) (mg/1000 ml): MnSO$_4$.4H$_2$O, 1000; Na$_2$MoO$_4$.2H$_2$O, 25; H$_3$BO$_3$, 300; ZnSO$_4$.7H$_2$O, 200; CuSO$_4$.5H$_2$O, 3.87; CoCl$_2$.6H$_2$O, 2.5; KI, 75.

B5 vitamins (100×) and Gamborg's vitamin solution (1000×) from Sigma cell culture.

FeEDTA(200×) (g/200 ml): Ferric-sodium salt, 1.47.

2,4-D (1 mg/ml): Dissolve 100 mg of 2,4-dichloro-phenoxyacetic acid in 1 ml absolute ethanol, add 3 ml of 1N KOH, adjust to pH 6 with 1N HCl.

BAP (1 mg/ml): 6-benzyl amino purine from Sigma cell culture.

NAA (1 mg/ml): Naphthalene acetic acid from Sigma cell culture.

ABA (2.5 mg/ml): Dissolve 250 mg of Abscisic acid in 2 ml of 1M NaOH, make up to 100 ml with sterile distilled water. Final background concentration to be 20 mM NaOH.

Hygromycin (50 mg/ml): Hygromycin solution from Roche.

Timetin (150 mg/ml): Dissolve 3100 mg of Timetin in 20.66 ml of sterile water. Final concentration to be 150 mg/ml.

Claforan (200 mg/ml): Dissolve 4 gm of Claforan in 20 ml of sterile water.

MS salts: Murashige-Skoog minimal organic medium.

N6D medium (amount per liter):

| | |
|---|---|
| N6 macro (10X) | 100 ml |
| N6 micro (1000X) | 1 ml |
| N6 vitamins (1000X) | 1 ml |
| MS iron/EDTA | 5 ml |
| Myoinositol | 100 mg |
| Casamino acid | 300 mg |
| Proline | 2.9 g |
| 2,4-D (1 mg/ml) | 2 ml |

Sucrose 30 g pH adjusted to 5.8 with 1M KOH, add 3 g phytogel/liter, autoclave.

NB medium (amount per liter):

| | |
|---|---|
| N6 macro-elements (20X) | 50 ml |
| B5 micro-elements (100X) | 10 ml |
| B5 vitamins (100X) | 10 ml |
| FeEDTA (200X) | 5 ml |
| 2,4-D (1 mg/ml) | 2 ml |
| Sucrose | 30 g |
| Proline | 500 mg |
| Glutamine | 500 mg |
| Casein enzymatic hydrolysate (CEH) | 300 mg |

NBO: NB media, plus 30 g/l mannitol and 30 g/l sorbitol, added before pH adjustment.

NBCT+selection (Hygromycin-H30): NB media plus 30 mg/l hygromycin, Timentin 150 mg/ml, Claforan 200 mg/l.

NBCT+selection (Hygromycin-H50); NB media plus selection 50 mg/l hygromycin, 200 mg/l Claforan and Timentin 150 mg/ml.

PRCT+Selection: NB media with no 2,4-D, plus following added after autoclave: BAP, 2 mg/l; NAA, 1 mg/l; ABA, 5 mg/l; Claforan, 100 g/l; Timetin; 150 mg/ml+selection.

RCT+Selection: NB media with no 2,4-D, plus following added after autoclave: BAP; 3 mg/l; NAA, 0.5 mg/l; Timetin, 150 mg/ml; Claforan, 100 mg/l+selection.

½ MS media: MS salts and vitamin mixture, 2.21 g; Sucrose, 10 g per liter, add 2.5 g phytogel/l, after autoclaving add 0.05 mg/l NAA and Timentin 150 mg/ml.

Example 2

Identification and Isolation of FatB Genes from Rice

FatB genes encode the enzyme palmitoyl-ACP thioesterase which have the activity of preferentially transferring fatty acids that have a length of 16 carbons or less from acyl carrier protein to acyl-CoA and thus prevent further elongation of the fatty acid carbon chain. Putative rice FatB sequences were identified using homology based searches using the sequence for the Genbank accession *Arabidopsis* locus AtACPTE32 and Iris locus AF213480. The program used was Megablast available at NCBI (www.ncbi.nlm.nih.gov/). Default parameters used by NCBI were used and the databases used were both non-redundant (nr) and high throughput gene sequences (htgs) for rice, *Oryza sativa*. The most similar sequences from rice selected by the Megablast program were then translated and examined for the presence of the conserved sequence NQHVNN(SEQ ID NO:26) found in all FatB sequences. A further amino acid residue believed to be essential in *Arabidopsis* is cysteine 264 and along with asparagine 227 and histidine 229 (which are both present in the conserved sequence NQHVNN) comprise the proposed catalytic triad. The Chinese Rice Database (current Website address rise.genomics.org.cn/rice/index2.jsp) was also used to a limited extent and default parameters for BLAST searching were used with the *Arabidopsis* sequence and Iris sequences. The translated sequences are aligned in FIG. 2.

An overview of the structures of all the FatB genes is shown as in FIG. 3. The genes described correspond as follows to the protein sequences discussed—AC108870 corresponds to Os11g43820, AP005291 corresponds to Os02g43090, AP000399 corresponds to Os06g5130 and AP004236 corresponds to Os06g39520. Note the possibility of multiple transcripts from one gene as indicated on the diagram. FIG. 4 shows a CLUSTAL W (fast) alignment of the 'gene' sequences using default parameters—note that the 'genes' are of different lengths.

The genes comprise 6 exons. The structure of the gene described by Os06g5130 is shown in detail FIG. 5.

FIG. 6 shows an alignment of the coding sequences of the FatB cDNAs indicating the different primers used for selective PCR amplification.

The sequence identity between the translated peptide sequence of Os06g5130 and Os06g39520 (corresponding to sequence ap000399 and ap004236 in FIG. 2) was 74% overall, and the identity at the nucleotide level over the entire coding sequence was 69%. In both cases the program BESTFIT with default parameters was used. The polypeptides deduced from Os02g43090 (one transcript), Os06g05130, Os06g39520 and Os011g43820 correspond to 298, 427, 423 and 425 amino acids respectively.

Activity of the encoded proteins was surmised from the high degree of sequence identity with known polypeptides shown to have this activity. Furthermore, the observed effect on palmitic acid levels of gene inactivating constructs based on these sequences was also consistent with this conclusion (see below).

Expression of the gene family was complex, with at least seven transcripts predicted from these four genes. On the basis of RT-PCR experiments that were performed and relative numbers of clones recovered from EST libraries, it appeared that RNA from Os06g5130 was relatively abundant in the grain, while Os11g43820 was expressed at a moderate levels in that tissue and the other genes were only expressed at a low level.

Example 3

Identification and Isolation of Fad2 Genes from Rice

Proteins encoded by Fad2 genes (Fatty acid desaturase 2) are responsible for the introduction of a double bond into 18:1 fatty acids—they are Δ12 desaturases. The Genbank sequence from the *Arabiodopsis* locus athd12aaa was used to search the nr and htgs databases for *Oryza sativa* using Megablast at default settings. The most similar sequences retrieved from rice were translated and examined for the presence of conserved hydrophobic motifs FSYVVHDLVIVAALL-FALVMI (SEQ ID NO:27), AWPLYIAQGCVLTGVWVIA (SEQ ID NO:28), ISDVGVSAGLALFKLSSAFGF (SEQ ID NO:29), VVRVYGVPLLIVNAWLVLITYLQ (SEQ ID NO:30) and the histidine rice sequences HECGHH (SEQ ID NO:31), HRRHHA (SEQ ID NO:32) and HVAHH (SEQ ID NO:33). The translated amino acid sequences of the isoforms obtained are shown in FIG. 7.

FIG. 8 provides an alignment of Fad2 sequences showing location of 5' UTR in isoform AP004047 (lowercase) and location of primers used for amplification by RT-PCR (underlined). The location of the stop codon is indicated by a box and untranslated regions downstream of the stop codon are in lower case.

Four gene sequences are recovered as being highly similar from the rice genome when the nucleotide sequence encoding the protein with the amino acid sequence of AP004047 was used to search the rice genome using the program BLAST with the default parameters. The overall structure of these genes are shown in FIG. 9. The genes correspond to the protein sequences as follows. The protein sequence AP004047 (also called FAD2-1 herein) corresponded to the gene Os02g48560, the sequence AP005168 (also called FAD2-2 herein) corresponded to Os07g23410, and the sequence contig2654 corresponded to Os07g23430. In addition there was a sequence that shared an intriguing extent of sequence identity but was clearly different to these sequences and may be a pseudo-gene. This sequence was Os07g23390.

Unlike the FatB genes, the Fad2 genes did not contain any introns. An alignment of all the protein coding sequences is shown in FIG. 10. The sequence identity over the entire coding region for Os02g48560 to Os07g23410 was 79%.

The molecular weight of the polypeptide encoded by Os02g48560 (ie AP004047) was 44.35 kDa before processing and contained 388 amino acids. The molecular weight of the polypeptide encoded by Os07g23410 was 44.9 kDa and contained 390 amino acids. These deduced polypeptides had 77% sequence identity as determined by the program BESTFIT using default parameters. The deduced polypeptide from Os07g23430 had a molecular weight of 41 kDa (363 amino acids) and from Os07g23390 was 24 kDa (223 amino acids). An alignment of all the deduced polypeptide sequences is shown in FIG. 7.

The sequence corresponding to Os02g48560 was expressed in the grain and this observation was consistent with data from the relative frequencies of clones for this gene in EST libraries where cognate sequences were recovered from grain cDNA libraries. Sequences corresponding to two of the isoforms encoded on chromosome 7 (Os07g23430, 23410) have been recovered from a leaf EST library but the sequence corresponding to the other gene (Os07g23390) has not yet been reported; we concluded it may be expressed at low levels if at all.

In conclusion, the rice Fad2 gene family was also a complex gene family. The two transcripts deduced from Os02g48560 were indistinguishable by sequence. The sequence deduced from Os02g48560 was clearly expressed in the grain.

Example 4

Expression of FatB and Fad2 Genes in Rice

To determine which, if any, of the 4 putative FatB and 3 Fad2 genes identified in rice as described in Examples 2 and 3 might be expressed in developing rice grain, reverse transcription polymerase chain reaction (RT-PCR) assays were carried out. Since the genes were closely related in sequence, primers had to be designed that were specific for each of the genes, to assay transcripts for each gene specifically. Regions of sequence divergence were identified from the alignments (FIGS. 6 and 8) and several primer pairs were designed and tested. Primer sequences for detecting expression of the putative FatB genes are given in Tables 3 and 4. As an internal standard against which to compare expression levels, RT-PCR was also carried out on the RNA for expression of the rice gene encoding alpha-tubulin, OsTubA1. This gene was known to be expressed in all actively dividing tissues and was not affected by the hormone ABA and so was suitable as a constitutively expressed control for leaf and grain analysis.

RNA was prepared from rice grains approx 15 days after flowering using the Qiagen RNeasy kit following protocols supplied by the manufacturer. DNAse treatment (DNA-free kit, Ambion) was then used to remove contaminating DNA from the RNA preparation. The RT-PCR mix contained 5 μl of 5× Qiagen OneStep RT-PCR buffer, 1 μl of dNTP mix (containing 10 mM of each dNTP), 15 pmol of each primer and approximately 20 pg of RNA to a final volume of 25 μl. The following RT-PCR cycling program was used for the RT-PCR amplifications: 30 min at 50° C. (reverse transcription), 15 min at 95° C. (initial PCR activation), 30 cycles of (1 min at 94° C., 1 min at 57° C., 1 min at 72° C.) (PCR amplification), then a final extension of 10 min at 72° C.

TABLE 3

Primers designed to amplify and discriminate relative expression of the putative FatB transcripts using one-step RT-PCR

| Gene Amplified | Genbank ID/Chinese Contig no. ID | Primer name | Primer Sequence |
|---|---|---|---|
| FatB-1 | AP000399 | p0399F2 | CGCTGCTACCAAACAATTCA (SEQ ID NO: 34) |
| | | p0399R2 | TTCTGTGTTGCCATCATCG (SEQ ID NO: 35) |
| FatB-2 | AC108870 | p5291_F2 | CAGGAAATAAAGTTGGTGATGATG (SEQ ID NO: 36) |
| | | p8870R | CTTCACAATATCAGCTCCTGACTC (SEQ ID NO: 37) |
| FatB-3 | AP005291 | p5291_F2 | CAGGAAATAAAGTTGGTGATGATG (SEQ ID NO: 38) |
| | | p5291R | CTTCACAATGTCAGCCTTCAC (SEQ ID NO: 39) |
| FatB-4 | AP004236 | p4236F2 | ACAGGCCTGACTCCACGAT (SEQ ID NO: 40) |
| | | p4236R2 | GTCCAGAGTGCTTGTTGCAG (SEQ ID NO: 41) |

TABLE 3-continued

Primers designed to amplify and discriminate relative expression of the putative FatB transcripts using one-step RT-PCR

| Gene Amplified | Genbank ID/Chinese Contig no. ID | Primer name | Primer Sequence |
|---|---|---|---|
| OsTubA1 | AF182523 | OSTUBA1_F | TACCCACTCCCTCCTTGAGC (SEQ ID NO: 42) |
|  |  | OSTUBA1_R | AGGCACTGTTGGTGATCTCG (SEQ ID NO: 43) |

TABLE 4

Primers designed to amplify and discriminate relative expression of the putative Fad2 transcripts using one-step RT-PCR.

| Gene Amplified | Genbank ID/ Chinese Contig no. ID | Primer name | Primer Sequence |
|---|---|---|---|
| Fad2-1 | AP004047 | pFad2-1F | CACAAAGAGGGAGGGAACAA (SEQ ID NO: 44) |
|  |  | pFad2-1R | GAAGGACTTGATCACCGAGC (SEQ ID NO: 45) |
| Fad2-2 | Contig2654 | UTR_2654_F | CACAACATCACGGACACACA (SEQ ID NO: 46) |
|  |  | UTR_2654_R | GCAAGACCGACATGGCTAAT (SEQ ID NO: 47) |
| Fad2-3 | AP005168 | UTR_5168_F | ACGTCCTCCACCACCTCTT (SEQ ID NO: 48) |
|  |  | UTR_5168_R | CAGAAGCAGTGACATACCCAAG (SEQ ID NO: 49) |
| OsTubA1 | AF182523 | OSTUBA1_F | TACCCACTCCCTCCTTGAGC (SEQ ID NO: 50) |
|  |  | OSTUBA1_R | AGGCACTGTTGGTGATCTCG (SEQ ID NO: 51) |

Results from the RT-PCR experiments demonstrated that the sequence Fad2-1 gene (TIGR rice database identifier LOC_Os02g48560) was highly expressed in both grain and leaf relative to the genes encoding the other isoforms. The other two Fad2 genes (LOC_Os07g23410 and LOC_Os07g23430) appeared to be expressed at low levels and primarily in the leaf. The analysis of genes encoding the FatB isoforms showed that FatB-1 (Genbank identifier AP000399, Tigr LOC_Os06g05130) and FatB-2 (Genbank identifier AC108870, TIGR identifier Os11g43820) were more highly expressed in the grain than the other two genes. The Tos-17 transpositional insertion mutant had an insertion in the gene encoding AP000399.

In leaf tissue, FatB-1 (Genbank identifier AP000399, TIGR LOC_Os06g05130) and FatB-4 (AP004236, TIGR LOC_Os06g39520) were more highly expressed, referring to the relative abundance of mRNA transcripts from the genes. When compared to the abundance of the tubulin gene transcripts as a standard, which was a moderately abundant mRNA in wheat grain and was therefore expected to similarly abundant in rice grain, all the FatB and Fad2 mRNAs accumulated to low levels as determined by RT-PCR. However, this conclusion was based on the assumption that the primers, for each of the genes tested, hybridized to the target transcripts with similar efficiency to the tubulin primers/transcript.

This conclusion is corroborated by EST database searching. When the Fad2-1 (TIGR Os02g48560) sequence was used to search rice EST sequences, transcript sequences were present in panicle, root and whole plant cDNA libraries. In contrast, Fad2-2 (TIGR Os07g23410) and Fad2-3 (TIGR Os07g23430) sequences were present only in leaf, shoot or whole plant libraries. The sequence for Os07g23390, the Fad2-like gene considered to be a pseudogene, was not present in any of the EST libraries. Similarly, FatB-1 (TIGR Os06g05130) sequences were present in both leaf and panicle EST libraries, whereas FatB-2 sequences (TIGR Os11g43820) were present only in panicle or whole plant EST libraries and FatB-4 (TIGR Os06g39520) only in a leaf library. FatB-3 (AP005291, Os02g430900) sequences although expressed at a relatively low level to the others in both leaf and grain as judged by RT-PCR, were present in panicle and whole plant EST libraries. These searches used the BLAST program on the NCBI website (ncbi.nlm.nih.gov/BLAST/Blast.cgi) using the EST database and limiting the search to sequences from rice.

Based on these data, Fad2-1 and FatB-2 were considered to be the genes that should be down-regulated for alteration of grain lipid. FatB-3 was also thought be important in this regard.

Example 5

Construction of Gene Silencing Constructs and Transformation of Rice

Creation of DuplexRNA Construct for Inhibition of Fad2 Expression

A construct was designed to express a duplex RNA (hairpin RNA) in developing rice grain in order to reduce expression of Fad2-1. By targeting common regions of the three Fad2 gene sequences, the construct was designed so that it would be effective for all three of the identified Fad2 genes in rice grain in order to potentially maximize the effect on fatty acid composition. To improve silencing efficiency, the construct contained an intron between the sense and antisense portions of the inverted repeat sequences as described by Smith et al. (2000).

A 505 basepair fragment was amplified by PCR from the 5' end of the Fad2-1 gene using the oligonucleotides pFad2-F 5'-AAAGGATCCTCTAGAGGGAGGAGCAGCAGAAGC-3' (SEQ ID NO:52) and pFad2-R 5'-AAAACTAGTGAATTCTACACGTACGGGGTGTACCA-3' (SEQ ID NO:53). The PCR product was ligated into pGEM-Teasy, transformed into E. coli and colonies containing the insert identified. The XbaI/EcoRI fragment from the plasmid designated pGEM-T-Fad2, containing the 505 bp Fad2 fragment, was then ligated in the sense direction into the vector ZLRint9_BC3895 (obtained from Zhongyi Li, CSIRO Plant Industry) containing the intron Rint9. A BamHI/SpeI fragment from pGEM-T-Fad2 was then ligated (in the antisense orientation) into the resultant plasmid so that an intron containing hairpin construct was formed. The BamHI/KpnI fragment containing the Fad2-1 intron containing hairpin was then inserted into the same restriction sites of the pBx17casNOT vector (Zhongyi Li, personal communication), containing the Bx17 seed specific promoter containing a Nos terminator/polyadenylation sequence so that the silencing gene would be expressed in developing seed in the order (promoter) sense-intron-antisense (terminator). The HindIII/NotI fragment containing the Bx17 promoter and Fad2-1 inverted repeat region was then inserted into the same restriction sites of the binary vector pWBvec8 (Wang et al., 1998)

that contained a selectable maker gene conferring hygromycin resistance. This vector was then introduced into *Agrobacterium* and used for rice transformation as described in Example 1. The duplex RNA construct was designated dsRNA-Fad2-1.

Creation of DuplexRNA Construct for Inhibition of FatB Expression

A 665-basepair fragment of the rice palmitoyl-ACP thioesterase FatB-1 gene (Tigr LOC_Os06g05130) was amplified by PCR using primers with the following sequences: Rte-s1, 5'-AGTCATGGCTGGTTCTCT-TGCGGC-3' (SEQ ID NO:54) and Rte-a1, 5'-ACCATCAC-CTAAGAGACCAGCAGT-3' (SEQ ID NO:55). This PCR fragment was used to make an inverted repeat construct with one copy of the fragment in the sense orientation and a second copy in the antisense orientation, separated by the intron sequence from the 5' UTR of the cotton microsomsal ω6-desaturase GhFad2-1 gene (Liu et al., 1999). The inverted repeat construct was subsequently inserted into the SacI site between the Ubi1 promoter and Nos terminator of pUbilcas-NOT (from Zhongyi Li based on sequence described in Li et al., 1997). The inverted repeat portion of rice FatB with the pUbil promoter was then inserted in the NotI site of the binary vector pWBVec8 and introduced into *Agrobacterium* as for the Fad2 construct described above. The duplex RNA construct was designated dsRNA-FatB-1.

Analysis of Fatty Acid Composition in Transformed Rice

Ten independent fertile transgenic plants obtained with dsRNA-Fad2-1 were tested for the presence of the dRNA gene by PCR using one primer corresponding to a site within the promoter region and a second primer for the end of the Fad2 sequence. Nine of the ten plants were found to be positive in the PCR reaction and therefore contained the Fad2 RNAi construct. Similarly, 23 fertile transgenic lines were tested for the FatB RNAi construct and 20 lines were found to be PCR positive.

To analyse the effect of the transgenes on fatty acid composition, total lipid was isolated from grain and leaf samples of the transformed rice plants. This was also done for a rice mutant line containing a Tos17 insertional sequence in the gene for FatB-1 (TIGR locus Os06g5130 corresponding to the protein identified by the Accession No. AP000399) to compare the effect of specifically inactivating this gene. Fatty acid composition was determined for each lipid extract by GC-FAME as described in Example 1. The data are presented in Tables 5 to 7 and some of that data is presented graphically in FIGS. 11 to 13. The proportion of each fatty acid was expressed as a percentage of the total fatty acid in the seed oil of the grain as determined by HPLC as described in Example 1.

The most striking and surprising aspect of the results was the extent of the change in grain oleic acid and linoleic acid composition in the Fad2 dsRNA plants. The proportion of oleic acid in some lines increased from 36% to at least 65% (w/w) and that of linoleic acid decreased from 37% to about 13% in the rice line most affected (Line 22A). Surprisingly, the proportion of palmitic acid in the Fad2 lines was also decreased, for example in Line 22A to less than 14% as compared to the control (18%).

In the FatB dsRNA lines, the reduction in the proportion of palmitic acid in the grain was correlated with an increase in the linoleic acid content while the proportions of oleic acid and linolenic acids were essentially unchanged. It was noted that the extent of the decrease in the proportion of palmitic acid in both Fad2 and FatB transgenic lines was similar, but the extent of increase in the linoleic acid level in the FatB lines was much less than the extent of the decrease observed in the Fad2 lines. That is, the extent of the change in levels of linoleic was greater with the Fad2 construct.

An interesting insight into the FatB catalysed step of the pathway is provided by analysis of the Tos-17 insertional knockout of one isoform of FatB, FatB-1. In the Tos-17 mutant, the extent of the change in the proportions of palmitic acid and oleic acid was reduced compared to the FatB dsRNA lines. These results indicated that genes encoding the FatB isoforms differed in their function.

When the results of the proportions of linoleic acid versus oleic acid were plotted as a scatter plot (FIG. 14), it was clear that the relationship between these two fatty acids in the Fad2 knockouts was the same as in wildtype rice, although the proportion of linoleic acid was vastly reduced. In contrast, with the FatB knockout and

TABLE 5

GC analysis of fatty acid composition in rice grain of FatB and Fad2 mutants

| Grain-Mutant | Myristic (C14:0) | Palmitic (C16:0) | Stearic (C18:0) | Oleic (C18:1) | Linoleic (C18:2) | Linolenic (C18:3) |
|---|---|---|---|---|---|---|
| Wild type (WH12) | 0.70 | 18.83 | 1.64 | 38.41 | 36.42 | 1.29 |
| FatB Tos17 insertional mutant | 0.72 | 15.13 | 2.33 | 37.15 | 38.61 | 1.87 |
| FatB dsRNA transformed line | 0.58 | 11.43 | 1.81 | 34.92 | 46.60 | 1.91 |
| Fad2 dsRNA transformed line | 0.58 | 14.26 | 2.11 | 64.94 | 12.62 | 1.23 |
| Control for Tos17 | 0.85 | 17.91 | 2.60 | 33.23 | 39.84 | 1.76 |
| Control for FatB dsRNA | 1.03 | 18.86 | 1.84 | 34.08 | 39.63 | 1.75 |
| Control for Fad2 dsRNA | 1.02 | 17.47 | 2.38 | 36.03 | 37.42 | 1.50 |

TABLE 6

GC analysis of fatty acid composition in rice leaves of FatB and Fad2 mutants

| Leaf-mutant | Lauric (C12:0) | Myristic (C14:0) | Palmitic (C16:0) | Stearic (C18:0) | Oleic (C18:1) | Linoleic (C18:2) | Linolenic (C18:3) |
|---|---|---|---|---|---|---|---|
| Wild-type (WF2) | | 0.80 | 14.43 | 1.90 | 2.32 | 8.99 | 68.96 |
| FatB Tos17 insertional mutant | | 0.34 | 11.55 | 1.84 | 2.24 | 15.04 | 67.70 |
| FatB dsRNA transformed line | 0.56 | 1.01 | 14.39 | 2.09 | 2.07 | 13.21 | 64.56 |

TABLE 6-continued

GC analysis of fatty acid composition in rice leaves of FatB and Fad2 mutants

| Leaf-mutant | Lauric (C12:0) | Myristic (C14:0) | Palmitic (C16:0) | Stearic (C18:0) | Oleic (C18:1) | Linoleic (C18:2) | Linolenic (C18:3) |
|---|---|---|---|---|---|---|---|
| Fad2 dsRNA transformed line | | | | | | | |
| Control for Tos17 | | 0.39 | 10.52 | 1.80 | 2.30 | 15.61 | 67.65 |
| Control for FatB dsRNA | 0.72 | 1.15 | 13.30 | 2.03 | 4.04 | 24.62 | 52.28 |

TABLE 7

Relative amounts of grain fatty acids in mutant lines compared to corresponding control lines (% in mutant/% in corresponding control)

| | Myristic (C14:0) | Palmitic (C16:0) | Stearic (C18:0) | Oleic (C18:1) | Linoleic (C18:2) | Linolenic (C18:3) |
|---|---|---|---|---|---|---|
| Grain fatty acids | | | | | | |
| FatB Tos17 insertional mutant | 0.85 | 0.8451* | 0.899 | 1.118* | 0.9691 | 1.06 |
| FatB dsRNA transformed line | 0.57* | 0.6060* | 0.980 | 1.025 | 1.176* | 1.09 |
| Fad2 dsRNA transformed line | 0.570* | 0.8167* | 0.887* | 1.802* | 0.3373* | 0.822* |
| Leaf fatty acids | | | | | | |
| FatB Tos17 insertional mutant | nd | 0.911* | 0.977 | 1.03 | 1.037 | 0.9992 |
| FatB dsRNA transformed line | nd | 0.9247 | 0.969 | 1.95* | 1.864* | 0.8098* |

*Statistically significant change to a lesser extent in the FatB Tos-17 line, although the relationship between linoleic acid and oleic was similar, it is shifted by a constant. This meant that there was more linoleic acid in the FatB knockout plants for a given amount of oleic acid than in wild-type or Fad2 knockout plants. This was consistent with the idea that knockout of FatB influenced the pathways controlling the amounts of oleic and linoleic acid but not the step directly linking oleic acid and linoleic acid which was controlled by Fad2.

The results of the proportion of linoleic acid versus palmitic were also plotted for all of the rice lines analysed. A positive linear relationship was observed for the Fad2 knockout lines, inverse of what was observed for linoleic versus oleic acid. For the FatB lines, however, a different relationship is observed (FIG. 15). A difference in the relationship between oleic and palmitic acid was also observed when the Fad2 dsRNA plants and FatB dsRNA plants were plotted as a scatter plot (FIG. 16). These results confirmed that the relationship between palmitic and linoleic acid (and oleic acid) was different for the two perturbations of the pathway.

Principal component analysis of the proportions of the various fatty acids under different perturbations of the pathway confirm that principal component 1 (which indicates the axes that contribute the greatest variation) was composed of the proportions of linoleic versus oleic whereas the principal component 2 (the second most important set of axes) was composed of proportions of linoleic and oleic acid versus palmitic acid). This is illustrated in FIG. 17.

We also concluded from the results presented in this Example that crossing the dsRNA Fad2 plants with the dsRNA FatB plants or Tos-17 FatB plants to combine the mutations would further increase the relative proportion of oleic acid and further decrease palmitic and linoleic acid levels.

Example 6

Production and Use of Antibodies

Antibodies were raised by synthesizing 15 or 16-mer peptides that were present in the deduced sequence of FatB. The peptides used to raise antibodies against FatB were:

FatB-U1 Ac-CGMNKNTRRLSKMPDE (SEQ ID NO:56). This corresponds to the translated sequence of FatB (Accession No. AP000399) from amino acid position number 259 and was also found in sequences translated from AP005291, AC108870 and AC004236. However, the sequence was only identical between the four isoforms in the sequence TRRLSKMPDE (SEQ ID NO:57).

FatB-U2. Ac-CGEKQWTLLDWKPKKPD (SEQ ID NO:58). This sequence was found in the translated sequence of all four FatB isoforms.

FatB-99. Ac-CGAQGEGNMGFFPAES (SEQ ID NO:59). This sequence was found only in AP00399 and was at the very C terminus of the deduced polypeptide.

After synthesis the peptides were coupled to either Ovalbumin or Keyhole Limpet Haemocyanin protein (KLH) using the cross-linker MBS (maleimidobenzoic acid N-hydroxyl succinamide ester) using standard techniques. The cross-linked peptide was dialysed and lyophilized and injected into rabbits at two weekly intervals for two months with Friends incomplete adjuvant at a concentration of approx 1 mg/ml. Antisera raised against FatB-99 detected a clear difference between FatB isoforms in that a polypeptide of 20 kDa present in wild-type rice was missing in the Tos-17 mutant line having an insertion in the gene corresponding to TIGR identifier Os06g5130, the product corresponds to FatB-1, the sequence is represented by accession No. AP000399 (FIG. 18). Although this was different to the expected size of approx 40 kDa, such a discrepancy had been noticed before with FatB isoforms Different size of FatB products have been observed in developing and mature *Cuphea wrightii* seeds showing five different FatB isoforms, longer size in mature seeds and shorter product in mature seeds (Leonard et al., 1997).

The antisera can be used to detect FatB protein in the transgenic or mutant plant samples and confirm the extent of gene inactivation.

Example 7

Identification of Mutants in Rice Fad2

PCR products spanning the active sites (essentially positions 330 to 1020 if the initiating ATG is taken as the start of the numbering in TIGR Loc_Os2g48560) of Fad2-1 (coding sequence corresponding to AP00 4047 in NCBI database, TGR locus identifier LOC_Os02g48560) will be produced from rice DNA extracted from a large number of different rice accessions. The size of the products will be up to 800 bp depending on the primers used. Two sets of overlapping primer pairs may need to be used. One possible set of primers is:

```
Set A
GTGCCGGCGGCAGGATGACGG (SEQ ID NO: 60)
(positions 5-20 in the alignment shown in FIG. 10)

GCCGACGATGTCGTCGAGCAC (SEQ ID NO: 61)
(reverse complement of positions 379-398 in the
alignment shown in FIG. 10)

Set B
TGCCTTCTCCGACTACTCGG  (SEQ ID NO: 62)
(positions 360-379 in FIG. 10)

CCTCGCGCCATGTCGCCTTGG (SEQ ID NO: 63)
(reverse complement of positions 1099-1118 in FIG.
10).
```

The annealed products will then be subjected to melting in a Rotorgene 6000 instrument (Corbett Life Science) or a comparable instrument where differences in melting of heteroduplexes can be sensitively detected by means of alteration of fluorescence of a dye LC Green. Hundreds and possibly thousands of rice lines can be screened daily by this technique.

The PCR products from samples showing an altered thermal profile will be sequenced and the mutations in Fad2 identified. Selected mutations which inactivate Fad2 can then be crossed into elite rice lines to produce rice lines with reduced Fad2 activity and therefore high oleic acid. If two or all of the Fad2 isoforms need to be eliminated then this can be achieved by identifying lines with the required mutations in different isoforms and combining the mutations in an elite rice line through marker assisted breeding. At least the Fad2-1 gene needs to be inactive for substantial increases in oleic acid content or decreased linoleic acid content. Inactivation of one or more of the additional Fad2 genes will further increase oleic acid content and decrease linoleic acid content. Mutants having mutations in additional Fad2 genes may be identified in the same way as for Fad2-1, using specific primers for the additional Fad genes.

Example 8

Stability Analysis—Detection of Hexanal Production in Storage

Experiments are underway with FSA, Werribee to detect the production of hexanal on storage in wildtype rice. This involves GC using a sampler to detect the volatiles in the headspace of grain stored at high temperature (40° C.). Once the system is optimized (and also we have sufficient quantity of grain) we will undertake a comparison of the production of volatiles, particularly hexanal, upon storage of wildtype and Fad2 RNAi and FatB RNAi rice lines and suitable combinations of genotypes. This is an important quality issue in the rice industry for storage of grain and also of storage of bran. The production and detection of other volatiles, which could have a role in affecting grain quality, is also being investigated, both with FSA, Werribee and CSIRO Entomology.

Around 10 g of raw brown rice is required for headspace analysis. The brown rice is stored at 4° C. (control) and 35° C. for 8 weeks. The gas sample released from brown rice can be obtained in the headspace of a vial by either heating at 80° C. or by natural diffusion. The volatile components in the headspace can then be analysed by direct injection into a GC or GC-MS machine and analysis of the gas chromatographic profiles (Suzuki et al., 1999). Another method for analysis of volatiles in the headspace is through the trapping of volatiles onto a suitable matrix (eg 250 mg Tenax GR) as described by Nielsen et al. (2004) using nitrogen as a purge gas. The desorption of the aroma compounds is then done thermally and the trapped molecules are analysed by GC and identified using standards.

The expectation that storage of rice would be improved in rice lines with low linoleic acid is based on a number of observations. Suzuki et al. (1999). have presented data that the amount of free linoleic acid increases during storage and that the amount of volatile aldehydes such as pentanal, hexanal and pentanol increase three fold at 35 C. The correlation of hexanal and volatile aldehydes with odour has been noted by other authors as well. On the other hand, Zhou et al. (2002) found a reduction of total linoleic acid upon storage and related this to the decomposition of linoleic acid to other products, including volatiles responsible for off-odours. The differences in the results may be due to differences in the extraction and analytical methods.

The production of hexanal for linoleic acid in vitro has been demonstrated by Nielsen et al. (2004).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

This application claims priority from AU 2006903810, the entire contents of which are incorporated herein by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abdullah et al. (1986) Biotechnology 4:1087.
Akagi et al. (1995) Plant Physiol. 108, 845-846
Almeida and Allshire (2005) TRENDS Cell Biol 15: 251-258.
Anai et al. (2003) Plant Cell Rep. 21, 988-992.
Ascherio and Willett (1997) Am. J. Clin. Nutr. 66: 1006S-1010S.
Bligh and Dyer Canadian J. Biochem. (1959) 37: 911-917.
Boggs et al. (1964) J. Food Sci. 29:487-489.
Bonanome and Grundy (1988). N. Engl. Med. 318:1244-1248.
Brandt et al. (1985) Carlsberg Res. Commun. 50: 333-345.
Broun et al., (1999) Annu. Rev. Nutr. 19: 197-216.
Buhr et al. (2002). Plant J. 30: 155-163.
Capecchi (1980) Cell 22:479-488.
Champagne et al. (1995) Cereal Chem 72:255-258.
Chang et al., (1978). J. Am. Oil Chem. Soc. 55: 718-727.
Chapman et al., (2001). J. Am. Oil Chem. Soc. 78: 941-947.
Choudry et al. (1980) Phytochemistry 19: 1063-1069.

Clapp (1993) Clin. Perinatol. 20:155-168.
Colot et al. (1987) EMBO J 6: 3559-3564.
Comai et al. (2004) Plant J 37: 778-786.
Curiel et al. (1992) Hum. Gen. Ther. 3:147-154.
Dougherty et al. (1995). Am. J. Clin. Nutr. 61:1120-1128.
Eglitis et al. (1988) Biotechniques 6:608-614.
Fenandez San Juan (1995). Alimentaria 33: 93-98.
Fujimura et al. (1985) Plant Tissue Culture Letters 2:74.
Graham et al. (1973) Virology 54:536-539.
Gunstone (2001) Inform 11: 1287-1289.
Ha (2005) Nutrition research 25, 597-606.
Haseloff and Gerlach (1988) Nature 334:585-591.
Henikoff et. al. (2004) Plant Physiol 135: 630-636.
Hu et al. (1997). N. Engl. J. Med. 337: 1491-1499.
Jennings and Akoh (2000) Journal of Agricultural and Food Chemistry, 48:4439-4443.
Jones et al. (1995) Plant Cell 7: 359-371.
Kinney (1996) J. Food Lipids 3: 273-292.
Kodama et al. (1997) Plant Molecular Biology 33:493-502.
Kohno-Murase et al. (2006). Transgenic Research 15:95-100.
Koziel et al. (1996) Plant Mol. Biol. 32:393-405.
Langridge et al. (2001) Aust J Agric Res 52: 1043-1077.
Lemieux (2000) Current Genomics 1: 301-311.
Leonard et al. (1997) Plant Molecular Biology, Volume 34, Issue 4: 669-679.
Li et al. (1997) Molec Breeding 3:1-14.
Lu et al. (1993) J. Exp. Med. 178:2089-2096.
Liu et al. (1999) Aust. J. Plant Physiol. 26:101-106.
Liu et al. (2002a). J. Am. Coll. Nutr. 21: 205S-211S.
Liu et al. (2002b). Plant Physiol. 129: 1732-1743.
Mensink and Katan (1990). N. Engl. J. Med. 323: 439-445.
Mikidlineni and Rocheford (2003) Theor. Applied Genetics, 106, 1326-1332.
Millar and Waterhouse (2005) Funct Integr Genomics 5:129-135.
Moghadasian and Frohlich (1999) Am. J. Med. 107: 588-94.
Morrison (1988) J Cereal Sci 8:1-15.
Most et al. (2005) Am J Clin Nutr 81:64-8.
Needleman and Wunsch (1970) J. Mol. Biol. 48:443-453.
Nielsen et al. (2004) Journal of Agricultural and Food Chemistry 52:2315-2321.
Noakes and Clifton (1998) Am. J. Clin. Nutr. 98: 242-247.
Ohlrogge and Jaworski (1997) Annu Rev Plant Physiol Plant Mol Biol. 48:109-136.
Oil World Annual (2004) International Seed Testing Association (ISTA) Mielke GmbH, Hamburg, Germany
Pasquinelli et al. (2005) Curr Opin Genet Develop 15: 200-205.
Perriman et al. (1992) Gene 113: 157-16.
Radcliffe et al (1997) Biochem Arch 13: 87-95.
Resurreccion et al (1979) Journal of the Science of Food and Agriculture, 30: 475-481.
Roche and Gibney (2000) Am. J. Clin. Nutr. 71: 232S-237S.
Rukmini et al. (1991). Journal of The American College of Nutrition 10: 593-601.
Sebedio et al. (1994) Fett. Wiss. Technol. 96: 235-239.
Senior (1998) Biotech. Genet Engin. Revs. 15:79-119.
Shibuya et al. (1974) Journal of the Japanese Society of Food Science and Technology 21: 597-603.
Shin et al. (1986) J. Food Sci. 51:460-463.
Shippy et al. (1999) Mol. Biotech. 12: 117-129.
Slade and Knauf (2005) Transgenic Res 14: 109-115.
Smith et al. (2000) Nature 407: 319-320.
St Angelo et al. (1980) J Lipids 1:45-49.
Stefanov et al. (1991) Acta Biologica Hungarica 42:323-330.
Stoutjesdijk et al., (2000). Biochem. Soc. Trans. 28: 938-940.
Stoutjesdijk et al. (2002) Plant Physiology 129: 1723-1731.
Stymne and Stobart (1987) Lipids, Vol. 9: 175-214.
Suzuki et al. (1999) J. Agric. Food Chem. 47: 1119-1124.
Taira et al. (1988) J. Agric. Food Chem. 34:542-545.
Thelen and Ohlrogge (2002) Metabolic Engineering 4: 12-21
Theriault et al. (1999). Clin. Biochem. 32: 309-19.
Tholstrup et al. (1994) Am. J. Clin. Nutr. 59: 371-377.
Toriyama et al. (1986) Theor. Appl. Genet. 205:34.
Tsugita et al (1983) Agricultural and Biological Chemistry 47: 543-549.
Tsuzuki et al (2004) Lipids 39:475-480.
Voelker et al. (1996). Plant J. 9: 229-241.
Wagner et al. (1992) Proc. Natl. Acad. Sci. USA 89:6099-6103.
Wang et al. (1998) ACTA Hort. 461:401-407.
Waterhouse et al. (1998) Proc. Natl. Acad. Sci. USA 95: 13959-13964.
Williams et al. (1999) J. Am. Coll. Cardiol. 33:1050-1055.
Yasumatsu et al. (1966) Agric. Biol. Chem. 30:483-486.
Zhou et al. (2002) Journal of Cereal Science 35:65-78.
Zock et al. (1994) Arterioscler Thromb. 14: 567-575

The invention claimed is:

1. Rice oil obtained from rice grain, the rice oil having a fatty acid composition comprising greater than 60% w/w oleic acid, less than 15% w/w palmitic acid and less than 25% w/w linoleic acid, wherein the ratio of oleic to linoleic acid in the rice oil differs by no more than 5% when compared to the ratio of oleic acid to linoleic acid in the rice grain.

2. The rice oil of claim 1, wherein the weight ratio of oleic acid to linoleic acid is greater than 3.0:1.

3. The rice oil of claim 1, having a fatty acid composition comprising greater than 60% w/w oleic acid, less than 12% w/w palmitic acid, and/or less than 15% w/w linoleic acid.

4. The rice oil of claim 1, further comprising γ-oryzanol.

5. A food product comprising the rice oil of claim 1.

6. The rice oil of claim 1, which is substantially purified.

7. The substantially purified rice oil of claim 6, which is at least 75% free from other components with which it is naturally associated.

8. The substantially purified rice oil of claim 7, which is at least 90% free from other components with which it is naturally associated.

* * * * *

UNITED STATES PATENT AND TRADEMARK OFFICE
CERTIFICATE OF CORRECTION

PATENT NO. : 8,530,724 B2
APPLICATION NO. : 12/309276
DATED : September 10, 2013
INVENTOR(S) : Whitelaw et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 950 days.

Signed and Sealed this

Fifteenth Day of September, 2015

Michelle K. Lee
*Director of the United States Patent and Trademark Office*

SEQUENCE LISTING

```
<160> NUMBER OF SEQ ID NOS: 83

<210> SEQ ID NO 1
<211> LENGTH: 425
<212> TYPE: PRT
<213> ORGANISM: Oryza sativa

<400> SEQUENCE: 1

Met Ala Gly Ser Leu Ala Ala Ser Ala Phe Phe Pro Gly Pro Gly Ser
1               5                   10                  15

Ser Pro Ala Ala Ser Ala Arg Ser Ser Lys Asn Ala Ala Val Thr Gly
            20                  25                  30

Glu Leu Pro Glu Asn Leu Ser Val Arg Gly Ile Val Ala Lys Pro Asn
        35                  40                  45

Pro Pro Pro Ala Ala Met Gln Val Lys Ala Gln Ala Gln Thr Leu Pro
    50                  55                  60
```

Lys Val Asn Gly Thr Lys Val Asn Leu Lys Thr Val Lys Pro Asp Met
 65                  70                  75                  80

Glu Glu Thr Val Pro Tyr Ser Ala Pro Lys Thr Phe Tyr Asn Gln Leu
                 85                  90                  95

Pro Asp Trp Ser Met Leu Leu Ala Ala Ile Thr Thr Ile Phe Leu Ala
            100                 105                 110

Ala Glu Lys Gln Trp Thr Leu Leu Asp Trp Lys Pro Lys Lys Pro Asp
        115                 120                 125

Met Leu Val Asp Thr Phe Gly Phe Gly Arg Ile Ile Gln Asp Gly Met
130                 135                 140

Val Phe Arg Gln Asn Phe Met Ile Arg Ser Tyr Glu Ile Gly Ala Asp
145                 150                 155                 160

Arg Thr Ala Ser Ile Glu Thr Leu Met Asn His Leu Gln Glu Thr Ala
                165                 170                 175

Leu Asn His Val Arg Thr Ala Gly Leu Leu Gly Asp Gly Phe Gly Ala
            180                 185                 190

Thr Pro Glu Met Ser Lys Arg Asn Leu Ile Trp Val Val Ser Lys Ile
        195                 200                 205

Gln Leu Leu Val Glu Gln Tyr Pro Ala Trp Gly Asp Thr Val Gln Val
210                 215                 220

Asp Thr Trp Val Ala Ala Gly Lys Asn Gly Met Arg Arg Asp Trp
225                 230                 235                 240

His Val Arg Asp Tyr Asn Ser Gly Arg Thr Ile Leu Arg Ala Thr Ser
                245                 250                 255

Val Trp Val Met Met His Lys Lys Thr Arg Arg Leu Ser Lys Met Pro
            260                 265                 270

Asp Glu Val Arg Ala Glu Ile Gly Pro Tyr Phe Asn Asp Arg Ser Ala
        275                 280                 285

Ile Thr Glu Glu Gln Ser Glu Lys Leu Ala Lys Thr Gly Asn Lys Val
290                 295                 300

Gly Asp Asp Ala Thr Glu Gln Phe Ile Arg Lys Gly Leu Thr Pro Arg
305                 310                 315                 320

Trp Gly Asp Leu Asp Val Asn Gln His Val Asn Asn Val Lys Tyr Ile
                325                 330                 335

Gly Trp Ile Leu Glu Ser Ala Pro Ile Ser Val Leu Glu Lys His Glu
            340                 345                 350

Leu Ala Ser Met Thr Leu Asp Tyr Arg Lys Glu Cys Gly Arg Asp Ser
        355                 360                 365

Val Leu Gln Ser Leu Thr Thr Val Ser Gly Glu Cys Thr Ser Ile Gly
370                 375                 380

Ala Asp Lys Gln Ala Ser Ala Ile Gln Cys Asp His Leu Leu Gln Leu
385                 390                 395                 400

Glu Ser Gly Ala Asp Ile Val Lys Ala His Thr Glu Trp Arg Pro Lys
                405                 410                 415

Arg Ser His Ala Ala Glu Asn Ala
            420                 425

<210> SEQ ID NO 2
<211> LENGTH: 298
<212> TYPE: PRT
<213> ORGANISM: Oryza sativa

<400> SEQUENCE: 2

Met Ala Gly Ser Leu Ala Ser Ala Phe Phe Pro Gly Pro Gly Ser
1               5                   10                  15

Ser Pro Ala Ala Ser Ala Arg Ser Ser Lys Asn Ala Ala Val Thr Gly
            20                  25                  30

Glu Leu Pro Glu Asn Leu Ser Val Cys Gly Ile Val Ala Lys Pro Asn
            35                  40                  45

Pro Pro Ala Ala Met Gln Val Lys Ala Gln Ala Gln Thr Leu Pro
 50                  55                  60

Lys Val Asn Gly Thr Lys Val Asn Leu Lys Thr Val Lys Pro Asp Met
 65                  70                  75                  80

Glu Glu Thr Val Pro His Ser Ala Pro Lys Thr Phe Tyr Asn Gln Leu
                85                  90                  95

Pro Asp Trp Ser Met Leu Leu Ala Ala Ile Thr Thr Ile Phe Leu Ala
            100                 105                 110

Ala Glu Lys Gln Trp Thr Leu Leu Asp Trp Lys Pro Lys Lys Pro Asp
            115                 120                 125

Met Leu Val Asp Thr Phe Gly Phe Gly Arg Ile Ile Gln Asp Gly Met
130                 135                 140

Val Phe Arg Gln Asn Phe Met Ile Arg Ser Tyr Glu Ile Gly Ala Asp
145                 150                 155                 160

Arg Thr Ala Ser Ile Glu Thr Leu Met Asn His Leu Gln Glu Thr Ala
                165                 170                 175

Leu Asn His Val Arg Thr Ala Gly Leu Leu Gly Asp Gly Phe Gly Ala
            180                 185                 190

Thr Pro Glu Met Ser Lys Arg Asn Leu Ile Trp Val Ser Lys Ile
            195                 200                 205

Gln Leu Leu Val Glu Gln Tyr Pro Ala Trp Gly Asp Met Val Gln Val
 210                 215                 220

Asp Thr Trp Val Ala Ala Gly Lys Asn Gly Met Arg Arg Asp Trp
225                 230                 235                 240

His Val Arg Asp Tyr Asn Ser Gly Arg Thr Ile Leu Arg Ala Thr Ser
                245                 250                 255

Val Trp Val Met Met His Lys Lys Thr Arg Arg Leu Ser Lys Met Pro
            260                 265                 270

Asp Glu Val Arg Ala Glu Ile Gly Pro Tyr Phe Asn Asp Arg Ser Ala
            275                 280                 285

Ile Thr Glu Glu Gln Ser Glu Lys Leu Ala
 290                 295

<210> SEQ ID NO 3
<211> LENGTH: 427
<212> TYPE: PRT
<213> ORGANISM: Oryza sativa

<400> SEQUENCE: 3

Met Ala Gly Ser Leu Ala Ala Ser Ala Phe Phe Pro Val Pro Gly Ser
1               5                   10                  15

Ser Pro Ala Ala Ser Ala Arg Ser Ser Lys Asn Thr Thr Gly Glu Leu
            20                  25                  30

Pro Glu Asn Leu Ser Val Arg Gly Ile Val Ala Lys Pro Asn Pro Ser
            35                  40                  45

Pro Gly Ala Met Gln Val Lys Ala Gln Ala Gln Ala Leu Pro Lys Val
 50                  55                  60

Asn Gly Thr Lys Val Asn Leu Lys Thr Thr Ser Pro Asp Lys Glu Asp
65                  70                  75                  80

Ile Ile Pro Tyr Thr Ala Pro Lys Leu Thr Phe Tyr Asn Gln Leu Pro Asp
                85                  90                  95

```
Trp Ser Met Leu Leu Ala Ala Val Thr Thr Ile Phe Leu Ala Ala Glu
            100                 105                 110

Lys Gln Trp Thr Leu Leu Asp Trp Lys Pro Lys Pro Asp Met Leu
        115                 120                 125

Ala Asp Thr Phe Gly Phe Gly Arg Ile Ile Gln Asp Gly Leu Val Phe
130                 135                 140

Arg Gln Asn Phe Leu Ile Arg Ser Tyr Glu Ile Gly Ala Asp Arg Thr
145                 150                 155                 160

Ala Ser Ile Glu Thr Leu Met Asn His Leu Gln Glu Thr Ala Leu Asn
                165                 170                 175

His Val Lys Thr Ala Gly Leu Leu Gly Asp Gly Phe Gly Ala Thr Pro
            180                 185                 190

Glu Met Ser Lys Arg Asn Leu Ile Trp Val Val Ser Lys Ile Gln Leu
        195                 200                 205

Leu Val Glu Arg Tyr Pro Ser Trp Gly Asp Met Val Gln Val Asp Thr
    210                 215                 220

Trp Val Ala Ala Gly Lys Asn Gly Met Arg Arg Asp Trp His Val
225                 230                 235                 240

Arg Asp Tyr Asn Ser Gly Gln Thr Ile Leu Arg Ala Thr Ser Val Trp
                245                 250                 255

Val Met Met Asn Lys Asn Thr Arg Arg Leu Ser Lys Met Pro Asp Glu
            260                 265                 270

Val Arg Ala Glu Ile Gly Pro Tyr Phe Asn Gly Arg Ser Ala Ile Ser
        275                 280                 285

Glu Glu Gln Gly Glu Lys Leu Pro Lys Pro Gly Thr Thr Phe Asp Gly
    290                 295                 300

Ala Ala Thr Lys Gln Phe Thr Arg Lys Gly Leu Thr Pro Lys Trp Ser
305                 310                 315                 320

Asp Leu Asp Val Asn Gln His Val Asn Asn Val Lys Tyr Ile Gly Trp
                325                 330                 335

Ile Leu Glu Ser Ala Pro Ile Ser Ile Leu Glu Lys His Glu Leu Ala
            340                 345                 350

Ser Met Thr Leu Asp Tyr Arg Lys Glu Cys Gly Arg Asp Ser Val Leu
        355                 360                 365

Gln Ser Leu Thr Ala Val Ser Gly Glu Cys Asp Asp Gly Asn Thr Glu
    370                 375                 380

Ser Ser Ile Gln Cys Asp His Leu Leu Gln Leu Glu Ser Gly Ala Asp
385                 390                 395                 400

Ile Val Lys Ala His Thr Glu Trp Arg Pro Lys Arg Ala Gln Gly Glu
                405                 410                 415

Gly Asn Met Gly Phe Phe Pro Ala Glu Ser Ala
            420                 425

<210> SEQ ID NO 4
<211> LENGTH: 423
<212> TYPE: PRT
<213> ORGANISM: Oryza sativa

<400> SEQUENCE: 4

Met Ala Gly Ser Ile Ala Ala Ser Ala Phe Leu Pro Gly Ser Pro Ala
1               5                   10                  15

Ala Ala Pro Pro Lys Ser Val Leu Gly Glu Arg Pro Asp Ser Leu Asp
            20                  25                  30

Val Arg Gly Ile Ala Ala Lys Pro Gly Ser Ser Ser Ala Ala Ala
        35                  40                  45
```

Leu Arg Ala Gly Lys Thr Arg Thr His Ala Ala Ile Pro Lys Val Asn
 50                  55                  60

Gly Gly Ser Ser Ala Leu Ala Asp Pro Glu His Asp Thr Met Ser Ser
 65                  70                  75                  80

Ser Ser Ser Ser Ala Ala Pro Arg Thr Phe Tyr Asn Gln Leu Pro Asp
                 85                  90                  95

Trp Ser Met Leu Leu Ala Ala Ile Thr Thr Ile Phe Leu Ala Ala Glu
            100                 105                 110

Lys Gln Trp Thr Leu Leu Asp Trp Lys Pro Lys Arg Pro Asp Met Leu
        115                 120                 125

Thr Asp Thr Phe Gly Phe Gly Arg Met Ile His Glu Gly Leu Met Phe
    130                 135                 140

Arg Gln Asn Phe Ser Ile Arg Ser Tyr Glu Ile Gly Ala Asp Arg Thr
145                 150                 155                 160

Ala Ser Ile Glu Thr Leu Met Asn His Leu Gln Glu Thr Ala Leu Asn
                165                 170                 175

His Val Lys Ser Ala Gly Leu Leu Gly Asp Gly Phe Gly Ser Thr Pro
            180                 185                 190

Glu Met Ser Lys Arg Asp Leu Phe Trp Val Val Ser Gln Met Gln Ala
        195                 200                 205

Ile Val Glu Arg Tyr Pro Cys Trp Gly Asp Thr Val Glu Val Asp Thr
    210                 215                 220

Trp Val Gly Ala His Gly Lys Asn Gly Met Arg Arg Asp Trp His Ile
225                 230                 235                 240

Arg Asp Ser Val Thr Gly His Thr Ile Leu Lys Ala Thr Ser Lys Trp
                245                 250                 255

Val Met Met His Lys Leu Thr Arg Arg Leu Ala Arg Ile Pro Asp Glu
            260                 265                 270

Val Arg Thr Glu Ile Glu Pro Tyr Phe Phe Glu His Ala Ser Ile Val
        275                 280                 285

Asp Glu Asp Asn Gln Lys Leu Pro Lys Leu Pro Asp Ile Glu Gly Ala
    290                 295                 300

Asn Val Ala Lys Tyr Val Arg Thr Gly Leu Thr Pro Arg Trp Ala Asp
305                 310                 315                 320

Leu Asp Ile Asn Gln His Val Asn Asn Val Lys Tyr Ile Gly Trp Ile
                325                 330                 335

Leu Glu Ser Ala Pro Ile Ser Ile Leu Glu Lys His Glu Leu Ala Ser
            340                 345                 350

Ile Val Leu Asp Tyr Lys Arg Glu Cys Gly Arg Asp Ser Val Leu Gln
        355                 360                 365

Ser His Thr Thr Val Tyr Thr Asp Cys Asn Lys His Ser Gly Gln Thr
    370                 375                 380

Thr Leu His Cys Glu His Leu Leu Ser Leu Glu Ser Gly Pro Thr Ile
385                 390                 395                 400

Val Lys Ala Arg Thr Met Trp Arg Pro Lys Gly Thr Arg Pro Gln Glu
                405                 410                 415

Ser Ile Ile Pro Ser Ser Ser
            420

<210> SEQ ID NO 5
<211> LENGTH: 6943
<212> TYPE: DNA
<213> ORGANISM: Oryza sativa

<400> SEQUENCE: 5

```
ccatatgtgc agcataaaag gcaaatcagc cctgtttgac atggctccaa tgcttaaatt      60
ctttagagaa aaaacagact ttgtagatta aatcaaagtg gcataatctt tttattttga     120
taaaaatatt agaaaatatc atacccctaat attcttagca tagtactcca ttcatctcac    180
ttattaaggt acgatcaaac ttggcatagt cttcaaaggc tgtgttcttt cccccatttt    240
cctaacccat ctatctcgtt ttccgcgcac acattttca aactgctaaa cggtgtgatt     300
tatgcaaaaa cttctatatg aaagttgttt aaaaaaatca tattaatcca tttttttaaaa   360
aaatcagtta atacttaatt aatcatgcaa taaaacgaac ttcattttgc gtgctgggga    420
ggaggggctc ccaaccccctc ctccgaacac agccaaaagc tacttttgga ctttaaattt    480
gtcatatatt ataatgtttc tagtaacaaa accatagtca tatgaaagta aatttaaatg    540
ataatccaat gatattattt tcatcaaata gaatttaatt tataataaac tatttattga    600
taaaatattc agagagttga atattaaaat acctgtgtgc cttagtgagt gggccaaatt    660
aattaatgga gtagtaacag ctttaaccaa agaaatttca acaatttccc aagctagaaa    720
aaacccaact ccaaaataaa cttgagttag aactgtgtta agcacctaaa ttgtaatacc    780
tgttactctc tcgttctcat tctatatttg tcctaagtta aatatatcta cctttttta    840
tctgtcctaa gttaactatg tgtatgtcta tcttttctac tactccctcc gtttcaggtt    900
ataagacgtt ttgactttgg tcaaagtcaa actgctttaa gtttgactaa gtttgtagaa    960
aaaataataa catttttcaac ccaagacaaa tttattatga aaatatgttc aattattgat   1020
ttaatgaaac taatttggta ttataaatat tattatattt atatataaac ttagttaaat   1080
ttaaagtagt ttaagtttga tcaaagtcaa aatgttttat aacctgaaat ggagggagta    1140
agtaatttga aacgaagaga gcagacaaat aataaactag taaagcctgt gacttgggtt    1200
ctagtcattg atcgtgtaca tgtaggtctt gtttagatcc caaaaaattt tagccaaaac   1260
ctcacatcaa atatttggac acatgcaccc ctaccagtgt gtggaggcat tgcatacacg    1320
aaacatggaa aaggaatcaa cttgagaggt tagacctgct agctctacta ggtctggatg    1380
gtcatgcatt ttttttttgaa aaaaaccacg ctgcaagctc gacagcctca acctcaatgg   1440
caaccatgac aataatatgc atgacaatgg tgtaggagaa aagacacgtc gataaccaaa    1500
gggcgcggct gcgcatacaa aggcggagag aaggaacgat ggtggctcaa aaagaaagag    1560
cgtcggtggc agtggtgcgt ggagcgacac taaagttagt ggttgctgat ggtctcacac    1620
aatccctaat cgaaatattt atttttttc acttagtatt gctgatccgt gggccaccag    1680
ccaatcataa agaaaatgt tgagataaaa ggtggagtat cttcccccttc cttcccttt     1740
tgactcgaaa aaaaaagcg tcggtggcgg ccgtgcgtgt aacaacacta aagttagtgg    1800
ttgctggtgg tctgacacaa tccctaatca gtttgataa taataataat ttatttcctc    1860
ttattagtat tgctgatgcg tgggccacca atcaatcgta aagaaaaaaa atgttgagat   1920
aaaaggtggg ggtatcttct ccttctcttt tttttggct aaaataaaag tggtttctgg    1980
tagtctgaca caatctctaa tcgaaatatt tattttttc tcttagtatt gctgatacgt    2040
gggccaccag ccaataataa agaaaaaaa tgttagagat aaaaggcgga gagtatcttc    2100
cccttccttt tttttggcgt aaatgaaaga aaagagaaaa tctcccgtcg tctccttcct   2160
tgcgccaaga aagacgagcc gcggctcaac accggagggg aggggcgccg atctccatcg   2220
ccaaggagag cagagcaggg gaggggatcc tggtgagcct cctcttcctg attcatctct   2280
ctcccattct agcttcgggg gactactttt gcctggaatt tgctcgcgtt cgttcgtgcg    2340
ttcgttcgtt aaccctagct tcttctcttc tagatctgga ggaagctctt ctcctcctta    2400
```

```
atttcagagc cttaatacaa gtagtaacag tttaacctcc cccatgtccc aagttggatc   2460 cgccccctgcg agttccgata ttgggtcctc ccaattctca atgccatttt gttcatcggg   2520
gggcatatgg ttcattttg cctgcattga ttcaaatgtg gtttcgaatc gtttgtgaaa    2580
ttcgcgggtg tacttgttta tgatacatga ggccttttt ccccccatgag gaggcaaact   2640 ttttagtggg tggatccact agttcatgcc tcaattttt ttctcctctt ttaagttttc    2700
caaagagcta cattgttgta aagtgtctga tacaattgat tgtttattca ggttagcgct   2760
tttggcgtgt gattgatttc taaacgaatt ttgggccgtg aggggaagtt caatcatggc   2820
agggtctctt gccgcctcag cattcttccc aggtccaggc tcatctcctg cagcatcagc   2880
tagaagctcc aagaatgctg ctgttaccgg cgaattgccg gagaatttga gtgtctgtgg   2940
cattgtcgca aagcctaacc cacctcctgc agccatgcaa gtaaaggcac aggctcaaac   3000
ccttcccaag gttaatggta cgaaggttaa cctcaagacg gtgaagcctg acatggagga   3060
aacggtgcct cacagtgctc caaagacgtt ctataaccaa ctgccggatt ggagcatgct   3120
tcttgcggct attacaacca tcttcctcgc cgcagagaag cagtggacac tgcttgattg   3180
gaagccgaag aaacctgaca tgcttgttga cacatttggc tttggtagga tcatccagga   3240
cggtatggtg tttaggcaga acttcatgat tcggtcctac gagattggcg ctgatcgtac   3300
agcttctata gagacattga tgaatcattt acaggtaagt ggttgcacat tctgtttta    3360 gtttcatttc tcatttcagc attttgttat agattcgtat gtctctttca agctggcaat   3420
tatttaaaat tttgcaggaa acggctctta accatgtaag gactgctggt cttcttggag   3480
atggttttgg ggctacaccg gagatgagca acggaactt gatatgggtt gtcagcaaaa    3540
tccagcttct tgttgagcaa taccccgcat ggtactttt tgcaaacctt tgctcctctt    3600
gatatatgta tctttggttt cttctatca attccttact ctaagttgtc atttaattt     3660 cacattttaa attacttcat atttgttttg cttctttac agatatcgtt ttatgtacta    3720
ctttacagct gtgtgtcctt tgcatatttg ttttatttg tttaagaag attcttacac     3780 aagcaacagt agtatttagc tcaatattta cttttaacatg gtttatcata ttgttgtgtg  3840
gatctctggt ctgatttctc catacactgg ttggttgatg aaaatcaagt gaatctttta  3900
cttgctcgta aatttcgctg ctgcaggttt gcaagaatat gggttgaagt tttatactg   3960 ctatagaagg ccatgttttt ctttgatttc ccgtgatagg cctcatgttt tggaggttct   4020
gttattcctc cttggttgac taagaaatgt gtagtaatat cagctccagt tttgttggat  4080
caaggataga ttttgtggca aactaaattt tccaattagg aagaaatgaa tatattccta  4140
cttaagtggg aggagcatgc actttgtttc caattgtcga gccctgatta taacacaaac  4200
tatcaagtta tttctttgca tttagaaaca ggatttgcat ctttgggtaat cctcattaaa  4260 gacataatct agctttagta catgcaacat aaaagttatg atgccccaag gccttttttgg 4320 tacagcactg taagtctgta gctctccttg ctctatgttg tcctcaaaag acacaacatc  4380
agttaaaaga acagtaatct ctcctttaga cgtcaattat tagtggagta gtaatttaga  4440
tccaagagca acttcatttg ttacgcctta ttcattgccc aaagctgcct cattaaatga  4500
tgtcttctct gtgcttcctt ggatcttgaa ttatgctgag tgggaatgcc agaacgggca  4560
tgtacttacg ttttccagcg ataagctccg ttttaaaaat aaattagcaa gtgatttatt  4620
tgcatttata aacaaaaatt taccactcgg gtagttcata ttaaagttat tgtctagctt  4680
tattacaagc agcatgaaag ttacgatacc ccaaggcctg agtttggcag cacttaactc  4740
tgttgccctg ttttgtcttg aaaagtataa catcacttag caggacaatg ctctcccgaa  4800
```

```
aacataactg attagtggat agagggagag gtttagtccc aatagataat tgactggtta    4860
cttcatattc attgcccaga gctgcctcat taaatgttct gtcctgtgct ttcttggatc    4920
ttgaattaaa agacgtctgt acagggtacc acacctcaag ggatcacaat tcagaaagtt    4980
tcccttatt gggctgcagt aaatgattcc atcgtgtaga aaagaacaaa agcaattaat    5040
gctgtgccat atcatgggag aagctaagga ccgatctaga acagtgaact tttgttgaac    5100
agcatctgtc agtttaaatt tctaggtggt catcattcat caaataagtg gtgctagtac    5160
tactattcac acgttatgtt taaatcctct tgtcaactgt gtcaacaagt ggttgaaaac    5220
ttctttttg gggttttgag ttagaaaaat ggaagtgcaa tttcaaactg ttttttagt     5280
tcagatacaa ttgccgatgt ctttctgtgg atcaaaaaga atgacagatg tattgtacca    5340
acctgctatg gttttagggg agatatggtt caagttgaca catgggtcgc tgctgctggc    5400
aaaaatggca tgcgtcgaga ctggcatgtt cgtgactaca actctggccg aacaatcttg    5460
agagctacaa ggtttgggct tcaactgtat tctattgcaa gaatcatctg tatcattttt    5520
tttgtgagga catccaatct tggtatttct gcttggtcac atcattgata atcactaatt    5580
gtgctccttt tccaatccat tgttgcagt gtttgggtga tgatgcacaa gaaaactaga    5640
agactttcaa aaatgccaga tgaagttaga gctgaaatag gcccatattt caatgaccgt    5700
tcagctataa cagaggagca gagtgaaaag ttagcctaga caggaaataa agttggtgat    5760
gatgctacag agcaattcat aagaaagggg ctcactgtaa gtcagctaga catggttaca    5820
tactgaatta tcattatgcc tcaactgcta tcatttatct aagaaaaaca gtaataattg    5880
atctcacccc tcatttattt taaatgatat ttgatggact cttgtttact gcaacagcct    5940
agatggggtg acctcgatgt caatcagcat gtgaacaatg ttaaatatat tgggtggatc    6000
cttgaggtgg ttattcttgt cccttatatt cattgtttag agaaaaataa tttggcttta    6060
tccttttata tggtacttcc tttgtttcac aatgtaagtc atttttagcat ttcccatatt    6120
tatatttatg ctaatgaatc taaatagata tatgtgtcta gattcattgg catcaatatg    6180
aatgtgagaa atgctaaaat gacttacatt atgaaacgga gggagtagtt gttagggaac    6240
cattttatgt agtacttgca attattttct agagattctg atctgaccat ctgtattgtt    6300
gatattgtca ttagtcttac atctggtcag tcagaaggct ttcaaacatg tttctgagtt    6360
cttctctaatt ttttccccca gagtgctcca atttcagtac tggagaagca tgagcttgca    6420
agcatgaccc tggattacag gaaggagtgt ggccgagaca gcgtgctgca atcacttacc    6480
accgtgtcag gggaatgcac cagcattggc gccgacaagc aggcttctgc catccagtgc    6540
gaccatcttg tgaaggctga cattgtgaag gcacacacag agtggcgacc aaagcgatcg    6600
catgcagcag ctgagaacgc gtaaacaaac aaaccgacga aaatctgtgg tagggagaat    6660
atcaaacttc ccttgcctct gttgccctga agctgatctt gaagtgtgag ttgtattctg    6720
taaaaaatta gtagtttcca tagtgtgagg ttggaggga ggtgttggtg cttgcctact     6780
gtacctgcta catctattat ttcttgattc tttgttcgct ttttttttc tttttgttt      6840
ttaaccctg tggagataag acaggttttg aagtgtggaa gaggttgttt caatcgtcta    6900
attgattcaa ctattcagca agtaaactgc tccatggaaa ttt                     6943
```

<210> SEQ ID NO 6
<211> LENGTH: 4799
<212> TYPE: DNA
<213> ORGANISM: Oryza sativa

<400> SEQUENCE: 6

-continued

```
agaggagaaa ttctcccgtc gtctccttcc ttgcgccaag aaagacgagc cgcggctcaa      60
cagcggagtg gaggggcgcc gatctccatc gccgaggaga gcagagcagg ggaggggagg     120
ggatcctggt gagcctcctc ttcctgattc acctctctct cattctagct tcggggact     180 acttttgcct cgaatttgct tgcgttcgtt cgttaaccct agcttcttct cttctagatc     240
tggaggaagc tcttctcctc cttaatttca gagccttaat acaagtagta acagtttaac     300
cccccccccc cccatgtccc aagttggatc cgccctgcg agttccgata ttgggtcctc     360
ccaattctca atgccatttt gttcatcggg gggcatatgg ttcattttgc ctgcattgat     420
tcaaatgtgg tttcgaatcg tttgggaaat tcgcgggtgt acttgtttat gatatatgag     480 gcctttttt tccccatgag gaggcaaact ttttagtggg tggatccact agttcatgcc     540 tcaattttt ttctcctctt ttaagttttc caaagagcta cattgttgta aagtgtctaa     600
tacaattgat tgtttattca ggttagcgct tttggcgtgt gattgatttc taaacgaatt     660
ttgggccgtg aagggaagtt caatcatggc agggtctctt gccgcctcag cattcttccc     720
aggtccaggc tcatctcctg cagcatcagc tagaagctcc aagaatgctg ctgttaccgg     780
cgaattgccg gagaatttga gtgtccgtgg cattgtcgca aagcctaacc cacctcctgc     840
agccatgcaa gtaaaggcac aggctcaaac ccttcccaag gttaatggta cgaaggttaa     900
cctcaagacg gtgaagcctg acatggagga acggtgcct tacagtgctc caaagacgtt     960
ctataaccaa ctgccggatt ggagcatgct tcttgcggct attacaacca tcttccttgc    1020
cgcagagaag cagtggacac tgcttgattg gaagccaaag aaacctgaca tgcttgttga    1080
cacatttggc tttggtagga ttatccagga cggtatggtg tttaggcaga acttcatgat    1140
tcggtcctac gagattggtg ctgatcgtac agcttctata gagacattga tgaatcattt    1200
acaggtaagt ggttgcacat tctgttttta gttttatttc tcatttcagc attttgttat    1260
agattcatat gtctctttca agctggcaat tatttaaaat tttgcaggaa acagctctta    1320
accatgtgag gactgctggt cttcttggag atggttttgg ggctacaccg gagatgagca    1380
aacggaactt gatatgggtt gtcagcaaaa tccagcttct tgttgagcaa taccccgcat    1440
ggtacttctt tgcaaacctt tgctcctctt aatatatgta tctttggttg ctttctatca    1500
attccttacc gtaagttttc atttttgtca cattttaaat tacttcatat ttgttttgct    1560
tcttttacag atatcgtttt atgtactact ttatagctgt gtgtccttgg catatttgtt    1620
tctatttgtt taaagaagat tcttactcag gcaacagtag tatttagctc aatatttact    1680
ttaacatggt ttatcataat gttgtgtgga tctctggtct gatttctcca tatactggtt    1740
ggttgatgaa aatcaagtga atctttact tggtcgtata tttcgctgct gctggtttgc    1800
aagaatatgg gttgaaattt ttactgctat agaaggccat ttttctttt gatttcccgt    1860 gataggcctc atgtttagga ggtgctgtta ttcctcattg gttgactaag aaatgtgtag    1920
taatatcagc tccagttttg ttggatcaag gatagagttg tggcaaaact aaattttcca    1980
attaggaaga aatgaatata ttcctactta agtggggagg agcatgcact tgtttccaa    2040 ttgtcgagcc ctgattataa cacaaactat caagttattt ctttgcattt agaaacagga    2100
tttgcatctt gagtaatcct cattaaagac ataatctagc tttagtacat gcaacataaa    2160
agttctgatg ccccaaggcc ttttggtac agcactgtaa gtctgtagct atccttgctc    2220
tatgttgtcc tcaaaagaca caacatcagt taaaaacaaa gaagaacagt aatctctcct    2280
ttagacgtca gttattagtg gagtagtaat ttagatccaa gagcaacttc atttgttacg    2340
ccttattcat tgcccaaagc tgcctcatta aatgatgtct tctctgtgct tccttggatc    2400
```

```
ttgaattatg ttgagtggga atgccagaac gggcatgtac tttcgttttc cagcgataag    2460
ctccgtttta aaataaatt agcaagtgat ttatttacat ttacaaacaa aaatttacca    2520
ctcgggtagt tcacattaaa attattgtct agctttatta caagcaacat gaaaatttcg    2580
ataccccaag gcctgagttt ggcagcacta taactctgtt gccctgtttt gtcttgaaaa    2640
gtataatatc acttaacagg acaatgctct cccgaaaaca taactgatta gtggatagag    2700
agagtggttt aggtggtgtt tggatccggg gactaaattt tagttcatgt cacatcggat    2760
gtttggacac taattagaaa tattaaacat agactaataa taaaatttag tcccaataga    2820
taattgactg gttacttcat attcattgcc cagagctgcc tcattaaatg ttgtctgttc    2880
tgtgctttct tggatcttga attaaaagac gtctgtacag ggtaccacac ctcaagggat    2940
cacaattcag aaagtttccc tttattggtc tgcagtaaat gattccatcg tatagaaaag    3000
aacaaaagca attaatgctg tgccatatca tgggagaagc taaggaccca tctagaacag    3060
tgaacttttg ttgaacagca tctgtcagtt taaaaatcta ggtggtcatc attcatcaaa    3120
taagtggtgc tagtgctact attgcacacg ttatgtttaa atcctcttgt caactgtgtc    3180
aacaagtggt tgaaaacttc tttttggggg ttttgagtta taaaaatgga ggtgcaattt    3240
caaattgttt ttttagttca gatacaattg ccgacgtctt tctgtggatc aaaaaaatga    3300
cagatgtatt gtaccaacct gctatggttt taggggagat acggttcaag ttgacacatg    3360
ggttgctgct gctggcaaaa atggcatgcg tcgagactgg catgttcgtg actacaactc    3420
tggccgaaca atcttgagag ctacaaggtt tgggcttcaa cttttattcta ttgcaagaat    3480 catctgtatc gttttttta tgaggatatc caatcttggt atttctgctt gatcacatca    3540
ttgataattg ctaattgtgc tccttttcca atcctttctt gcagtgtttg ggtgatgatg    3600
cacaagaaaa ctagaagact tcaaaaatg ccagatgaag ttagagctga aataggccca    3660
tatttcaatg accgttcagc tataacagag gagcagagtg aaaagttagc caagacagga    3720
aataaagttg gtgatgatgc tacagagcaa ttcataagaa aggggctcac tgtaagtcag    3780
ctagacatag ttacatacta aattatcatt atgcctcaac tgcaatcatt tatctaagaa    3840
aaatagtaat atttgatctc accctcatt tattttaaat gatctttgat ggactcttgt    3900
ttactgcaac agcctagatg gggtgacctc gatgtcaatc agcatgtgaa caatgttaaa    3960
tatattgggt ggatccttga ggtggttatt cttgtccctt ttattcattg tttagagaaa    4020
aataatttgg ctttatcctt ttatatggtg gttgttaggg aaccatttta tgtagtactt    4080
gcaattattt tctagagatt ctgatctgac catctgtatt gttgatattg tcattagtct    4140
tacatctggt cagtcagaag gctttcaaac atgttttttga gttctttcta attttttccc    4200
ccagagtgct ccaatttcag tactggagaa gcatgagctt gcaagcatga ccctggatta    4260
caggaaggag tgtggtcgag acagcgtgct gcaatcactt accaccgtgt caggggaatg    4320
caccagcatt ggcgccgaca agcaggcttc tgccatccag tgcgaccatc ttcttcagct    4380
tgagtcagga gctgatattg tgaaggcaca cacagagtgg cgaccaaagc gatcgcacgc    4440
agcagctgag aacgcgtaaa caaacaaacc gacgaaaatc tgtgggaggg agaatatcaa    4500
acttcccttg cctctgttgc cctgaagctt atcttgaagt gtgagttgta ttctgtaaaa    4560
aattagtagt ttccatagtg tgaggttgga ggggaggtgt tggtgcttgc ctactgtacc    4620
tgctacatct attatttctt gattctttgt tcgctttttt ttttctttttt tgtttttaac    4680 ccctgtggag ataagacagg ttttgaagtg tggaagaggt tgtttcaatc gtctaattga    4740
ttcaactatt cagcaagtaa actgctccat ggaatttcat cgtttggttg gagcctgag    4799
```

<210> SEQ ID NO 7
<211> LENGTH: 4753
<212> TYPE: DNA
<213> ORGANISM: Oryza sativa

<400> SEQUENCE: 7

| | | | | | |
|---|---|---|---|---|---|
| cgcgtcgtgt | gagttggcga | gcccgaggag | cggaggcggc | cacaagtcta atccgcgtcg | 60 |
| tctgcgcgtt | cgtgggcgag | gaggagaaag | aagaggagga | agagagggaa gggggcttga | 120 |
| tttgatttgg | gcgcgtctcg | tggagtatcc | ggtgagttct | tggcgatctg gcgaggcgag | 180 |
| tgatgagtga | ttcctgctgc | tgctggggga | ttttggcgtg | attttcgttg gttgcatttt | 240 |
| gtttctttt | ttttgtatcg | atttgttgga | gctttattcg | gtagatctgg tcgattccat | 300 |
| ggtgagttgt | atcggcgccg | gagtgatagc | tgattctgtt | tttttgtgtg atttttttt | 360 |
| tgttttggaa | atagggtttg | tgtcgaattg | agggcatttt | ttttccttag gcaatgcagg | 420 |
| atttcgtttt | gtatgttttt | gcgtggaatg | gatatgaaca | gacctcgaac aaatggaaga | 480 |
| atttgtattt | tgtatgatgg | attgcaatgc | gatacttgtt | ttggggcgtg attcgattga | 540 |
| aataaatgaa | atattagagt | tattttggga | ttcctgtttg | ctgcgccttt ttttttagca | 600 |
| tttcttgata | tgaacaagag | aagaagggct | gaatttttt | cttagctttg gaggcattta | 660 |
| ctgtcccagt | attttctcct | accggaagca | gaatatttg | tttgattgga gggttgcctc | 720 |
| cctttgccaa | attgaatcaa | atgttctcgg | atgttttaaa | atttccgtgg actcttttg | 780 |
| ccccagggga | gaccgctttt | agcagctgga | tcccgtgttt | tcatttcaag ttcttgtttt | 840 |
| cctagtctcc | atatatttct | gattgttaac | tcgtattctc | tacctcacat atgcaaaatc | 900 |
| acacttgcgt | cgttctgtaa | ttagttagat | tctgcaagaa | aaatccggaa ttttcaagca | 960 |
| tgctagtagt | tttaaattga | tgccatgttt | tttagacaat | gttaattgat gccatatgac | 1020 |
| tataggacac | attatattgc | gtttctgaat | ataccactc | atgaaactca taattttgtt | 1080 |
| gattaattgt | tcaggttgcc | ccttctagtg | tgtaacttgg | agcaaatttg gaccctgaga | 1140 |
| cgcaaatcag | tcatggctgg | ttctcttgcg | gcgtctgcat | tcttccctgt cccagggtct | 1200 |
| tccctgcag | cttcggctag | aagctctaag | aacacaaccg | tgaattgcc agagaatttg | 1260 |
| agtgtccgcg | gaatcgtcgc | gaagcctaat | ccgtctccag | gggccatgca agtcaaggcg | 1320 |
| caggcgcaag | cccttcctaa | ggttaatgga | accaaggtta | acctgaagac tacaagccca | 1380 |
| gacaaggagg | atataatacc | gtacactgct | ccgaagacat | tctataacca attgccagac | 1440 |
| tggagcatgc | ttcttgcagc | tgtcacgacc | attttcctgg | cagctgagaa gcagtggact | 1500 |
| ctgcttgact | ggaagccgaa | gaagcctgac | atgctggctg | acacattcgg ctttggtagg | 1560 |
| atcatccaag | acgggctggt | gtttaggcaa | aacttcttga | ttcggtccta cgagattggt | 1620 |
| gctgatcgta | cagcttctat | tgagacatta | atgaatcatt | tacaggtgat acaatggagc | 1680 |
| tatgctgctt | tagcttttct | tccgtatttt | tcactattgg | tacattatgt tcgtggcata | 1740 |
| ctaactgtaa | tttgaagctt | tgcaggaaac | agctctgaac | catgtgaaaa ctgctggtct | 1800 |
| cttaggtgat | ggttttggtg | ctacgccgga | gatgagcaaa | cggaacttaa tatggggttgt | 1860 |
| cagcaaaatt | cagcttcttg | ttgagcgata | cccatcatgg | tacttttct gcaatccact | 1920 |
| actctccaca | tcattttctt | ggatggcaaa | acttctcttt | ttactcttaa ttcataacat | 1980 |
| ttctttcatt | cttaatggag | tactttttgtc | cccggtgcat | ttagtgtcac aatttaatgt | 2040 |
| ttacatggta | cggaaagat | ttatcactca | atatccacgg | tgtaatgttt ttagctaaac | 2100 |
| tcaatatcca | cggtgtaatg | tttttagcta | aacttgtctt | cagtccttt ttccttttc | 2160 |

```
cctatgtttg tgtgctgtgg cattcgatgg atcatcgaga ctctgagtag acgtagattc    2220
ttgcattcct tatgcgacat gaggcacatg ttcgagtgtt tatcaccta catgaaaacc     2280
tttccctact aagttgctgc ttctattgtt ctgcagatat aagcaatatt tttgcctatt    2340
tttcctgtgc tttgaacttc tcgtaggttc atggcccaca acctttagca ggcatagtgc    2400
cttgaaatgg agtattacac tcaaaagcat aacaataaca tgtattgcct tgtatgataa    2460
gatgagtgat agatcttttg aaatcattta ctgaggaaaa cgtttgttta tttgacaaga    2520
caatgtattg atgaactaga actgctctat taagtggtat ctgccctgtg tctcctttcg    2580
tacaaattgt tgcaccccctg ttcatgttac ttctcacttt tcaccatggc aggcatgttt   2640
agaaaatcat ttgattttac agggcattac catgtgaccc cttaataact aacaaatata   2700
ttttgggtcc accaaatctg tggtggatgg aaagggaaat taataaacac aaatggaaaa   2760
ttcttcattg tgaaacgtga taaggacaaa ttttgtgaat aaataaagta acaaaaaatg   2820
gctagtatttt gcctacatat agagtacacc tcaagagatc agaaaagttg cctttattga   2880
tggagtaatt gaattagtag taagcaataa attctgtgga cctaggggac atccctgatc    2940
tagatcgagt tttgatctca tgctacattt aatcttccat gtcagcaact ttcagtacct    3000
gctattaaat ttcccctgtt cttctgacga ttgatgcaat tttaagttta tgagaaggaa    3060
aacggtctgc tgttttgaa ttctgaatgt agtttacaca atttctcata ggctgaaatt     3120
ttggttgcaa atttttaggg gagatatggt ccaagttgac acatgggtag ctgctgctgg    3180
caaaaatggc atgcgtcgag attggcatgt tcgggactac aactctggtc aaacaatctt    3240
gagggctaca aggtttgtgt ttatcgtttg catttgttgc atttcttttg tttcatgctg    3300
tttaccagca tgtttattc cttttcgatt gctaattgtt cctctcttgt ttgcagtgtt     3360
tgggtgatga tgaataagaa cactagaaga ctttcaaaaa tgccagatga agttagagct    3420
gaaataggcc cgtatttcaa tggccgttct gctatatcag aggagcaggg tgaaaagttg    3480
cctaagccag ggaccacatt tgtgcttgtt accgtcattc attttgctgg tggttctcat    3540
gcataaaatt tctcatgagg gatcctttgt tcatgtcagc cgaagtggag tgaccttgat    3600
gtcaaccagc atgtgaacaa tgtgaagtat attggttgga tacttgaggt aacttctttt    3660
tcctttctc tatccgaaca tgctatctct agatcagaaa agagagtgtc tgatcgtaat     3720
tagtaaccta gttcctagtc atatgccaag ctgtaaaaac acttgcactg tatattcaaa    3780
agctattcaa atttctgagt acgttttgtt ttttttttcct cagagtgctc caatttcgat   3840
actggagaag cacgagcttg caagcatgac cttggattac aggaaggagt gtggccgtga    3900
cagtgtgctt cagtcgctta ccgctgtttc aggtgaatgc gatgatggca acacagaatc    3960
ctccatccag tgtgaccatc tgcttcagct ggagtccgga gcagacattg tgaaggctca    4020
cacagagtgg cgaccgaagc gagctcaggg cgaggggaac atgggctttt tcccagctga    4080
gagtgcatga gcgcttctgt agtttatccg gcaagtaacc tctttgagaa gtgcagattc    4140
taacttggct agcaacacag gacaaatgat tgttggtggg aaatttggca tgccgagcct    4200
gggttttgtg atgcacacag cacacattca gatttgaaga ttgagagatg cttcttattg    4260
gcagcttgtt cagaaagatg actaagcggt ttgggataaa atcagctgat tgggaaacat    4320
tagcaggatg ataagcatga ctggtggtac caatgaaaag ggttgaaatc ctttgcattg    4380
ttcatttgtt gtggagcaag agtggccgca gttgcttatc acacaggatg atggaggtgt    4440
ttgtgtgaag cttattgctg aagctggatt gttttttgacc tgtgtttcta aaagaaaagg   4500
gaaaagaaga agctgtggat tgaggccgga gcagcagaga tattcaatc gacatagata    4560
```

```
aataagatgt aatactaatt tagcccaggt ggtttgtgtg tggagatgca atccattgta    4620
gtaacagcct aacttgtaca ttcttgccat cttttttctta ttaattgaat gaatgaatcg    4680
cagacctcct gcgttttcat caataattga aatgacttct gcttcatcaa gaattgaatg    4740
aattgtctgt ctg                                                        4753

<210> SEQ ID NO 8
<211> LENGTH: 4441
<212> TYPE: DNA
<213> ORGANISM: Oryza sativa

<400> SEQUENCE: 8
gcgatgcgag cctgtgttga cagcggagaa agcagtgtaa tccggtcccg ccaccgcagc      60
cgcctccacc tctcttcccg gcgccaatgg ccgcgtcgtg aagcgcagca gcagcagcag     120
cagcggagac agcggcagaa gctttgccta aggtcggttt gcctccccgc ctccgccgca     180
ttccggttgg agttttgtcc gtgttcgtcg gcggtttctt ggctggccgg atgaattgtt     240
gtggggaggg ggaggggggag gggctctctc acgcactcgc tgctggatttt cggttaggtt     300 tcgcggctgg gggaatcgcg ggggaattca ggatctttgt tttgttagtt cttctttcgg     360
gcggggttgg atctcgagta atctgcgtcg tgttatttgc cgcgagattt gggtgttttt     420
tttcttctct ccgcatcttc tctctcgttc cttcgtctgt acggtctagt ggtggtctac     480
gggctacggc cgtggtaaaa gttctctag attttttggtc tcgttttttt ctttattttta     540 ggcggcttgc tttgcttcgc ctgctttgac gtttgaccag cggtttatcc tcgattattc     600
ttcctcgtga gtcgtgagca agctatgatt tgcagctaat gattttttgtg cttggattag     660 ataaaagatg cttctcactc ttcgtttgtt tccattttct ggaatttgtg atttcctggt     720
gatgataatg ttgtgctcgt gttgattcag gttgggatcc tccctattcg cgcgcgtctt     780
tgatttggcg cgtaaagttg taatccgtac tccggatggc cggctcaatc gccgcctcgg     840
cgttcttgcc gggtcgccg gcggccgcgc cgcccaagag cgtcctgggc gagcgcccgg     900
acagcctgga cgtccgcggc atcgccgcga agcgggctc ctcgtcgtcg gccgccgccc     960
tgagggccgg caagacgcgc acccacgccg ccatccccaa ggtgaacggc ggcagttcgg    1020
cgctggcgga tccggagcac gacacgatgt cctcctcctc ctcctccgcg gcgccgagga    1080
cgttctacaa ccagctcccc gactggagca tgctcctcgc agccatcacg accatcttct    1140
tggccgcgga gaagcagtgg acgctgctgg actggaagcc gaagcggccc gacatgctca    1200
ccgacacgtt cggtttcggc aggatgatac atgagggggct catgttcagg cagaacttct    1260
cgattaggtc ctatgagatc ggggccgata ggacggcgtc tatagaaacg ctgatgaacc    1320
atttgcaggt gaaatattgt gaattttcag gcgtcggatt gctcgggctg gcatcagaa    1380 cattgaaatg ttttttggttt tgatgcagga aaccgcactg aatcatgtga agagcgctgg    1440
gctgctagga gatggttttg gctcaacgcc agagatgagt aaacgagact tgttctgggt    1500
tgtcagccaa atgcaggcaa tcgttgagcg ttatccgtgc tggtataata ctataatttc    1560
acatatcagc atgttcttgg ttttgttttc ttacatagtt tgagctccaa atagggtgtt    1620
gcttttctgc tttcgtgtta catgacaatt aggaggcaca tagatgtatg gttggctgtc    1680
acagtacgtt actgtagtta tagtagctat catcttgctt cacagcagtc atggaataac    1740
aggtttaggt aaatggagtt ttcaagttgt ttggcaatga atatgaaaaa gattttccca    1800
agtgtttgta tcaattttaa atggatgagc aactcccatc tcttaactgt ttttgctatc    1860
ggcattaaat atttgtgcaa ctggtagact ttcagtaaac gatgatgatg cagaagcctc    1920
```

```
ctgtgctctt aatattattg atcatgtatc atattttctg tgagatgtta taattgttcg    1980
tgtttgttac ctgaaagtgc catgttgcca ataattaact tcttatctgt gtgcaggggt    2040
gatactgtcg aagtagatac atgggttggt gctcatggta aaatggaat gcgcagagac     2100 tggcatatac gtgattctgt aacaggccat acaatattga aggctacaag gtttgaatta    2160
ttgtcactct cataaatact gatgatcatg aaaactgtat tagcatctgc tattcaactt    2220
cctacccatc ttattaccac tgtttgcata tgaagtctag aagttctgtt tcttctgaac    2280
atattataag ctgccttaca gcaacatgaa gctacctatt tgtcctaatt gtttgctcaa    2340
tgtgcagtaa atgggttatg atgcacaagc ttacaaggag gctagcaaga attcctgatg    2400
aagtacgtac tgaaatagag ccatactttt ttgagcatgc ttctattgta gatgaagaca    2460
accagaaact tccaaaactg ccagatattg aaggtgctaa tgtagccaaa tatgtccgga    2520
caggcctgac tgtaagtttt gtggaattat acaagattac agtttacaag tatacaaaat    2580
gtgcatgttt ttcttttcatt ttttacatct tcttctgtct cataatgcag ccacgatggg    2640
ccgaccttga tatcaatcag catgttaata acgttaaata cataggtgg atcctagagg     2700 taaaaaagt tcccctatta tgttcatctt tattgcccctt gctaacaccct cttgcctaga    2760 tgattcttga gggaaaaaaa tgcttcttga agttcagtat gttactttca gaaaaaatat    2820
ccatttgttt ttatttactg taaacactcc atggagttgc tgttaggcat ctttgtcgcg    2880
gtattcatta ttaagttgtc acatggtgga gcataacttt gtgttgcttt acttgccttt    2940
ttctctttgg gcatacattt agtactattg atggtgctac ataattcaaa gagattcatt    3000
tatctcgcta tatttcccat atgttatgtt ccaagaattt gggaataaac agtaatcaga    3060
agagtactgg atttgtaggt actttatttt ttgtgtgtgt gtgtggggggg gggggggggc    3120 tcagatcatg cctatgatta ggcattactg taggagttta gataaacttg gtcaaggtcc    3180
caaaagggtg tgcctatggt tctacaagtg tccacctaac tttatcctca agcacgcaac    3240
cacttatctg gcagctttgt actctttcaa gctatacgaa aaatatctgt tgcactagtt    3300
ggagaagtaa tgtatcctag cagattttac tacattaggt tggtcaccta cgtacctaac    3360
cctgtacgct tgttgcttcc gataaagagc ttggctggaa tacttatatg caatttgatc    3420
acaagtcatt cacttaattc aattttttttt agagtgatca acacctgcat ataatgcata    3480
tttgcctggt tgacaatctg ccgtgtgtat gtgtgttttg gaagaagggg aggggtagtc    3540
atgtatgtat ttatccagtg gaccacataa tgaggaaaaa gaaattgttc aggtgacctg    3600
caacctagat gggcccaaaa caacccaaaa tattagggaa attaacactt caggcatttc    3660
ctaacataca gaaatattta ttaccaacat gcgcacatgt tgcttaaccc tacctttttg    3720
tcctttttcc ccctcagagc gcaccaatct ccattctgga gaaacatgag ctggcaagta    3780
ttgtcctgga ttacaagagg gagtgtggcc gagacagcgt gctgcaatca cacactaccg    3840
tgtacactga ctgcaacaag cactctggac aaaccacttt gcactgtgag catttgctga    3900
gcctggaatc aggacctacc atcgtcaagg ccaggaccat gtggaggcca aaaggaacca    3960 ggcccccaaga gagtatcatt ccgtcttcgt cgtgaagcgc gtaaaatctt tcatgtgttg    4020
attttggtag caacaacttg gttaaaccaa ggacaagtgg acaacaactt gtgttctcta    4080
tggaaaggca aaacctggat gaacataacg acggggacga agttatttta cagacaaaat    4140
gtatggattt ggaggagttc aaaagagggg gggggggggg ggggcaagat ggaggtaaaa    4200
tgcagaaaag acagaaggcg tattgtgcat gatttgttgt ttcagcttttt ccttctattt    4260 ttcctttcct tagcaaagat attcaattac acagatgggt gttgtaagta ttgaaattgt    4320
```

| agctactgct gtacaatggg aagtgaaatg cttctcatgc atgtttctgt ctgggctatg | 4380 |
| tctatattat gagccctcga aagcagattg cctggtccga attgtttgaa attttaagtt | 4440 |
| t | 4441 |

<210> SEQ ID NO 9
<211> LENGTH: 1284
<212> TYPE: DNA
<213> ORGANISM: Oryza sativa

<400> SEQUENCE: 9

| atggctggtt ctcttgcggc gtctgcattc ttccctgtcc cagggtcttc ccctgcagct | 60 |
| tcggctagaa gctctaagaa cacaaccggt gaattgccag agaatttgag tgtccgcgga | 120 |
| atcgtcgcga agcctaatcc gtctccaggg gccatgcaag tcaaggcgca ggcgcaagcc | 180 |
| cttcctaagg ttaatggaac caaggttaac ctgaagacta aagcccaga caaggaggat | 240 |
| ataataccgt acactgctcc gaagacattc tataaccaat tgccagactg gagcatgctt | 300 |
| cttgcagctg tcacgaccat tttcctggca gctgagaagc agtggactct gcttgactgg | 360 |
| aagccgaaga agcctgacat gctggctgac acattcggct tggtaggat catccaagac | 420 |
| gggctggtgt ttaggcaaaa cttcttgatt cggtcctacg agattggtgc tgatcgtaca | 480 |
| gcttctattg agacattaat gaatcattta caggaaacag ctctgaacca tgtgaaaact | 540 |
| gctggtctct taggtgatgg ttttggtgct acgccggaga tgagcaaacg gaacttaata | 600 |
| tgggttgtca gcaaaattca gcttcttgtt gagcgatacc catcatgggg agatatggtc | 660 |
| caagttgaca catgggtagc tgctgctggc aaaaatggca tgcgtcgaga ttggcatgtt | 720 |
| cgggactaca actctggtca aacaatcttg agggctacaa gtgtttgggt gatgatgaat | 780 |
| aagaacacta gaagactttc aaaaatgcca gatgaagtta gagctgaaat aggcccgtat | 840 |
| ttcaatggcc gttctgctat atcagaggag cagggtgaaa agttgcctaa gccagggacc | 900 |
| acatttgatg gcgctgctac caaacaattc acaagaaaag ggcttactcc gaagtggagt | 960 |
| gaccttgatg tcaaccagca tgtgaacaat gtgaagtata ttggttggat acttgagagt | 1020 |
| gctccaattt cgatactgga gaagcacgag cttgcaagca tgaccttgga ttacaggaag | 1080 |
| gagtgtggcc gtgacagtgt gcttcagtcg cttaccgctg tttcaggtga atgcgatgat | 1140 |
| ggcaacacag aatcctccat ccagtgtgac catctgcttc agctggagtc cggagcagac | 1200 |
| attgtgaagg ctcacacaga gtggcgaccg aagcgagctc agggcgaggg gaacatgggc | 1260 |
| tttttcccag ctgagagtgc atga | 1284 |

<210> SEQ ID NO 10
<211> LENGTH: 1500
<212> TYPE: DNA
<213> ORGANISM: Oryza sativa

<400> SEQUENCE: 10

| tcatggctgg ttctcttgcg gcgtctgcat tcttccctgt cccagggtct tcccctgcag | 60 |
| cttcggctag aagctctaag aacacaaccg gtgaattgcc agagaatttg agtgtccgcg | 120 |
| gaatcgtcgc gaagcctaat ccgtctccag gggccatgca agtcaaggcg caggcgcaag | 180 |
| cccttcctaa ggttaatgga accaaggtta acctgaagac tacaagccca gacaaggagg | 240 |
| atataatacc gtacactgct ccgaagacat tctataacca attgccagac tggagcatgc | 300 |
| ttcttgcagc tgtcacgacc attttcctgg cagctgagaa gcagtggact ctgcttgact | 360 |
| ggaagccgaa gaagcctgac atgctggctg acacattcgg ctttggtagg atcatccaag | 420 |

```
acgggctggt gtttaggcaa aacttcttga ttcggtccta cgagattggt gctgatcgta      480
cagcttctat tgagacatta atgaatcatt tacaggtgat acaatggagc tatgctgctt      540
tagcttttct tttgaagctt tgcaggaaac agctctgaac catgtgaaaa ctgctggtct      600
cttaggtgat ggttttggtg ctacgccgga gatgagcaaa cggaacttaa tatgggttgt      660
cagcaaaatt cagcttcttg ttgagcgata cccatcatgg atttctcata ggctgaaatt      720
ttggttgcaa atttttaggg gagatatggt ccaagttgac acatgggtag ctgctgctgg      780
caaaaatggc atgcgtcgag attggcatgt tcgggactac aactctggtc aaacaatctt      840
gagggctaca ttgcagtgtt tgggtgatga tgaataagaa cactagaaga ctttcaaaaa      900
tgccagatga agttagagct gaaataggcc cgtatttcaa tggccgttct gctatatcag      960
aggagcaggg tgaaaagttg cctaagccag ggaccacatt tgatggcgct gctaccaaac     1020
aattcacaag aaaagggctt actgtaagtc taaaatttct catgagggat cctttgttca     1080
tgtcagccga agtggagtga ccttgatgtc aaccagcatg tgaacaatgt gaagtatatt     1140
ggttggatac ttgaggtaac ttcttttttcc ttttctctat ccgaacatgc tatctctaga     1200
tctgagtacg ttttgttttt ttttcctcag agtgctccaa tttcgatact ggagaagcac     1260
gagcttgcaa gcatgacctt ggattacagg aaggagtgtg gccgtgacag tgtgcttcag     1320
tcgcttaccg ctgtttcagg tgaatgcgat gatggcaaca cagaatcctc catccagtgt     1380
gaccatctgc ttcagctgga gtccggagca gacattgtga aggctcacac agagtggcga     1440
ccgaagcgag ctcagggcga ggggaacatg ggcttttttcc cagctgagag tgcatgagcg     1500

<210> SEQ ID NO 11
<211> LENGTH: 1278
<212> TYPE: DNA
<213> ORGANISM: Oryza sativa

<400> SEQUENCE: 11
atggcagggt ctcttgccgc ctcagcattc ttcccaggtc caggctcatc tcctgcagca       60
tcagctagaa gctccaagaa tgctgctgtt accggcgaat tgccggagaa tttgagtgtc      120
cgtggcattg tcgcaaagcc taacccacct cctgcagcca tgcaagtaaa ggcacaggct      180
caaacccttc ccaaggttaa tggtacgaag gttaacctca agacggtgaa gcctgacatg      240
gaggaaacgg tgccttacag tgctccaaag acgttctata accaactgcc ggattggagc      300
atgcttcttg cggctattac aaccatcttc cttgccgcag agaagcagtg gacactgctt      360
gattggaagc caagagaaacc tgacatgctt gttgacacat ttggctttgg taggattatc      420
caggacggta tggtgtttag gcagaacttc atgattcggt cctacgagat tggtgctgat      480
cgtacagctt ctatagagac attgatgaat catttacagg aaacagctct taaccatgtg      540
aggactgctg gtcttcttgg agatggtttt ggggctacac cggagatgag caaacggaac      600
ttgatatggg ttgtcagcaa aatccagctt cttgttgagc aatacccccgc atggggagat      660 acggttcaag ttgacacatg ggttgctgct gctggcaaaa atggcatgcg tcgagactgg      720
catgttcgtg actacaactc tggccgaaca atcttgagag ctacaagtgt ttgggtgatg      780
atgcacaaga aaactagaag actttcaaaa atgccagatg aagttagagc tgaaataggc      840
ccatatttca tgaccgttca gctataacag gaggagcaga gtgaaaagtt agccaagaca      900
ggaaataaag ttggtgatga tgctacagag caattcataa gaagggggct cactcctaga      960
tggggtgacc tcgatgtcaa tcagcatgtg aacaatgtta aatatattgg gtggatcctt     1020
gagagtgctc caatttcagt actggagaag catgagcttg caagcatgac cctggattac     1080
```

```
aggaaggagt gtggtcgaga cagcgtgctg caatcactta ccaccgtgtc aggggaatgc    1140
accagcattg gcgccgacaa gcaggcttct gccatccagt gcgaccatct tcttcagctt    1200
gagtcaggag ctgatattgt gaaggcacac acagagtggc gaccaaagcg atcgcacgca    1260
gcagctgaga acgcgtaa                                                  1278
```

<210> SEQ ID NO 12
<211> LENGTH: 897
<212> TYPE: DNA
<213> ORGANISM: Oryza sativa

<400> SEQUENCE: 12

```
atggcagggt ctcttgccgc ctcagcattc ttcccaggtc caggctcatc tcctgcagca      60
tcagctagaa gctccaagaa tgctgctgtt accggcgaat gccggagaa tttgagtgtc     120 tgtggcattg tcgcaaagcc taacccacct cctgcagcca tgcaagtaaa ggcacaggct    180
caaacccttc ccaaggttaa tggtacgaag gttaacctca agacggtgaa gcctgacatg    240
gaggaaacgg tgcctcacag tgctccaaag acgttctata accaactgcc ggattggagc    300
atgcttcttg cggctattac aaccatcttc ctcgccgcag agaagcagtg gacactgctt    360
gattggaagc cgaagaaacc tgacatgctt gttgacacat ttggctttgg taggatcatc    420
caggacggta tggtgtttag gcagaacttc atgattcggt cctacgagat ggcgctgat     480 cgtacagctt ctatagagac attgatgaat catttacagg aaacggctct taaccatgta    540
aggactgctg gtcttcttgg agatggtttt ggggctacac cggagatgag caaacggaac    600
ttgatatggg ttgtcagcaa aatccagctt cttgttgagc aatacccgc atggggagat     660 atggttcaag ttgacacatg ggtcgctgct gctggcaaaa atggcatgcg tcgagactgg    720
catgttcgtg actacaactc tggccgaaca atcttgagag ctacaagtgt ttgggtgatg    780
atgcacaaga aaactagaag actttcaaaa atgccagatg aagttagagc tgaaataggc    840
ccatatttca atgaccgttc agctataaca gaggagcaga gtgaaaagtt agcctag       897
```

<210> SEQ ID NO 13
<211> LENGTH: 1284
<212> TYPE: DNA
<213> ORGANISM: Oryza sativa

<400> SEQUENCE: 13

```
atggctggtt ctcttgcggc gtctgcattc tttccctgtcc cagggtcttc ccctgcagct    60
tcggctagaa gctctaagaa cacaaccggt gaattgccag agaatttgag tgtccgcgga   120
atcgtcgcga agcctaatcc gtctccaggg gccatgcaag tcaaggcgca ggcgcaagcc   180
cttcctaagg ttaatggaac caaggttaac ctgaagacta caagcccaga caaggaggat   240
ataataccgt acactgctcc gaagacattc tataaccaat tgccagactg gagcatgctt   300
cttgcagctg tcacgaccat tttcctggca gctgagaagc agtggactct gcttgactgg   360
aagccgaaga agcctgacat gctggctgac acattcggct ttggtaggat catccaagac   420
gggctggtgt ttaggcaaaa acttcttgatt cggtcctacg agattggtgc tgatcgtaca   480
gcttctattg agacattaat gaatcattta caggaaacag ctctgaacca tgtgaaaact   540
gctggtctct taggtgatgg ttttggtgct acgccggaga tgagcaaacg gaacttaata   600
tgggttgtca gcaaaattca gcttcttgtt gagcgatacc catcatgggg agatatggtc   660
caagttgaca catgggtagc tgctgctggc aaaaatggca tgcgtcgaga ttggcatgtt   720
cgggactaca actctggtca aacaatcttg agggctacaa gtgtttgggt gatgatgaat   780
```

```
aagaacacta gaagactttc aaaaatgcca gatgaagtta gagctgaaat aggcccgtat      840
ttcaatggcc gttctgctat atcagaggag cagggtgaaa agttgcctaa gccaggggacc     900 acatttgatg gcgctgctac caaacaattc acaagaaaag ggcttactcc gaagtggagt      960
gaccttgatg tcaaccagca tgtgaacaat gtgaagtata ttggttggat acttgagagt     1020
gctccaattt cgatactgga gaagcacgag cttgcaagca tgaccttgga ttacaggaag     1080
gagtgtggcc gtgacagtgt gcttcagtcg cttaccgctg tttcaggtga atgcgatgat     1140
ggcaacacag aatcctccat ccagtgtgac catctgcttc agctggagtc cggagcagac     1200
attgtgaagg ctcacacaga gtggcgaccg aagcgagctc agggcgaggg gaacatgggc     1260
tttttcccag ctgagagtgc atga                                            1284

<210> SEQ ID NO 14
<211> LENGTH: 1272
<212> TYPE: DNA
<213> ORGANISM: Oryza sativa

<400> SEQUENCE: 14
atggccggct caatcgccgc ctcggcgttc ttgccggggt cgccggcggc cgcgccgccc       60
aagagcgtcc tgggcgagcg cccggacagc ctggacgtcc gcggcatcgc cgcgaagccg      120
ggctcctcgt cgtcggccgc cgccctgagg gccggcaaga cgcgcaccca cgccgccatc      180
cccaaggtga acggcggcag ttcggcgctg gcggatccgg agcacgacac gatgtcctcc      240
tcctcctcct ccgcggcgcc gaggacgttc tacaaccagc tccccgactg gagcatgctc      300
ctcgcagcca tcacgaccat cttcttggcc gcggagaagc agtggacgct gctggactgg      360
aagccgaagc ggccccgacat gctcaccgac acgttcggtt tcggcaggat gatacatgag      420
gggctcatgt tcaggcagaa cttctcgatt aggtcctatg agatcggggc cgataggacg      480
gcgtctatag aaacgctgat gaaccatttg caggaaaccg cactgaatca tgtgaagagc      540
gctgggctgc taggagatgg ttttggctca acgccagaga tgagtaaacg agacttgttc      600
tgggttgtca gccaaatgca ggcaatcgtt gagcgttatc cgtgctgggg tgatactgtc      660
gaagtagata catgggttgg tgctcatggt aaaaatggaa tgcgcagaga ctggcatata      720
cgtgattctg taacaggcca tacaatattg aaggctacaa gtaaatgggt tatgatgcac      780
aagcttacaa ggaggctagc aagaattcct gatgaagtac gtactgaaat agagccatac      840
ttttttgagc atgcttctat tgtagatgaa gacaaccaga aacttccaaa actgccagat      900
attgaaggtg ctaatgtagc caaatatgtc cggacaggcc tgactccacg atgggccgac      960
cttgatatca atcagcatgt taataacgtt aaatacatag ggtggatcct agagagcgca     1020
ccaatctcca ttctggagaa acatgagctg gcaagtattg tcctggatta caagagggag     1080
tgtggccgag acagcgtgct gcaatcacac actaccgtgt acactgactg caacaagcac     1140
tctggacaaa ccactttgca ctgtgagcat ttgctgagcc tggaatcagg acctaccatc     1200
gtcaaggcca ggaccatgtg gaggccaaaa ggaaccaggc cccaagagag tatcattccg     1260
tcttcgtcgt ga                                                         1272

<210> SEQ ID NO 15
<211> LENGTH: 388
<212> TYPE: PRT
<213> ORGANISM: Oryza sativa

<400> SEQUENCE: 15

Met Gly Ala Gly Gly Arg Met Thr Glu Lys Glu Arg Glu Glu Gln Gln
1               5                   10                  15
```

Lys Leu Leu Gly Arg Ala Gly Asn Gly Ala Ala Val Gln Arg Ser Pro
           20                  25                  30

Thr Asp Lys Pro Pro Phe Thr Leu Gly Gln Ile Lys Lys Ala Ile Pro
           35                  40                  45

Pro His Cys Phe Gln Arg Ser Val Ile Lys Ser Phe Ser Tyr Val Val
       50                  55                  60

His Asp Leu Val Ile Val Ala Ala Leu Leu Tyr Phe Ala Leu Val Met
65                  70                  75                  80

Ile Pro Val Leu Pro Ser Gly Met Glu Phe Ala Ala Trp Pro Leu Tyr
                    85                  90                  95

Trp Ile Ala Gln Gly Cys Val Leu Thr Gly Val Trp Val Ile Ala His
               100                 105                 110

Glu Cys Gly His His Ala Phe Ser Asp Tyr Ser Val Leu Asp Asp Ile
           115                 120                 125

Val Gly Leu Val Leu His Ser Ser Leu Leu Val Pro Tyr Phe Ser Trp
130                 135                 140

Lys Tyr Ser His Arg Arg His His Ser Asn Thr Gly Ser Leu Glu Arg
145                 150                 155                 160

Asp Glu Val Phe Val Pro Lys Gln Lys Ser Ala Met Ala Trp Tyr Thr
                    165                 170                 175

Pro Tyr Val Tyr His Asn Pro Ile Gly Arg Leu Val His Ile Phe Val
               180                 185                 190

Gln Leu Thr Leu Gly Trp Pro Leu Tyr Leu Ala Phe Asn Val Ser Gly
           195                 200                 205

Arg Pro Tyr Pro Arg Phe Ala Cys His Phe Asp Pro Tyr Gly Pro Ile
210                 215                 220

Tyr Asn Asp Arg Glu Arg Val Gln Ile Phe Ile Ser Asp Val Gly Val
225                 230                 235                 240

Val Ser Ala Gly Leu Ala Leu Phe Lys Leu Ser Ser Ala Phe Gly Phe
                    245                 250                 255

Trp Trp Val Val Arg Val Tyr Gly Val Pro Leu Leu Ile Val Asn Ala
               260                 265                 270

Trp Leu Val Leu Ile Thr Tyr Leu Gln His Thr His Pro Ala Leu Pro
           275                 280                 285

His Tyr Asp Ser Ser Glu Trp Asp Trp Leu Arg Gly Ala Leu Ala Thr
290                 295                 300

Val Asp Arg Asp Tyr Gly Ile Leu Asn Lys Val Phe His Asn Ile Thr
305                 310                 315                 320

Asp Thr His Val Ala His His Leu Phe Ser Thr Met Pro His Tyr His
                    325                 330                 335

Ala Met Glu Ala Thr Lys Ala Ile Arg Pro Ile Leu Gly Glu Tyr Tyr
               340                 345                 350

Gln Phe Asp Pro Thr Pro Val Ala Lys Ala Thr Trp Arg Glu Ala Lys
           355                 360                 365

Glu Cys Ile Tyr Val Glu Pro Glu Asp Asn Lys Gly Val Phe Trp Tyr
370                 375                 380

Asn Asn Lys Phe
385

<210> SEQ ID NO 16
<211> LENGTH: 362
<212> TYPE: PRT
<213> ORGANISM: Oryza sativa

<400> SEQUENCE: 16

Met Gln Arg Ser Pro Val Asp Lys Pro Pro Phe Thr Leu Gly Asp Ile
1               5                   10                  15

Lys Lys Ala Ile Pro Pro His Cys Phe His Arg Ser Val Ile Lys Ser
            20                  25                  30

Phe Ser Tyr Leu Leu His Asp Leu Ala Ile Ala Ala Gly Leu Leu Tyr
        35                  40                  45

Phe Ala Leu Val Gly Ile Pro Ala Leu Pro Ser Ile Leu Arg Leu Val
    50                  55                  60

Ala Trp Pro Leu Tyr Trp Ala Ala Gln Gly Ser Val Leu Thr Gly Val
65                  70                  75                  80

Trp Val Ile Gly His Glu Cys Gly His His Ala Phe Ser Asp Tyr Leu
                85                  90                  95

Leu Leu Asp Asn Leu Val Gly Leu Val Leu His Ser Ala Leu Leu Thr
            100                 105                 110

Pro Phe Phe Ser Trp Lys Tyr Ser His Arg His His Ala Asn Thr
        115                 120                 125

Gly Ser Met Glu Lys Asp Glu Val Tyr Val Ala Lys Lys Ser Ala
        130                 135                 140

Leu Pro Trp Tyr Thr Pro Tyr Val Phe Gly Asn Pro Val Gly Arg Leu
145                 150                 155                 160

Val Tyr Ile Ala Leu Gln Leu Thr Leu Ala Trp Pro Leu Tyr Leu Ala
                165                 170                 175

Phe Asn Leu Ser Gly Gln Pro Tyr Pro Arg Leu Val Thr Cys His Tyr
            180                 185                 190

Asp Pro Tyr Ser Pro Leu Phe Ser Asp Gln Glu Arg Val Gln Val Leu
        195                 200                 205

Val Ser Asp Ala Ala Ile Leu Ala Val Leu Leu Ala Leu His Arg Leu
        210                 215                 220

Thr Ala Ala Tyr Gly Leu Trp Trp Val Arg Val Tyr Gly Val Pro
225                 230                 235                 240

Val Met Ile Val Gly Ala Leu Phe Val Leu Ile Thr Tyr Leu His His
            245                 250                 255

Thr His Arg Ala Leu Pro His Tyr Asp Ser Ser Glu Trp Glu Trp Leu
        260                 265                 270

Arg Gly Ser Leu Ala Thr Val Asp Arg Asp Tyr Gly Val Leu Asn Arg
        275                 280                 285

Val Leu His Asn Val Thr Asp Thr His Val Leu His His Leu Phe Pro
        290                 295                 300

Ser Met Pro His Tyr His Ala Met Glu Ala Thr Arg Ala Ala Arg Pro
305                 310                 315                 320

Val Leu Gly Glu Tyr Tyr Lys Phe Asp Arg Thr Pro Ile Ile Glu Ala
            325                 330                 335

Thr Trp Arg Glu Ala Lys Glu Cys Met Tyr Val Glu Pro Arg Glu Arg
        340                 345                 350

Asp Gly Ile Tyr Trp Tyr Asn Asn Lys Phe
        355                 360

<210> SEQ ID NO 17
<211> LENGTH: 390
<212> TYPE: PRT
<213> ORGANISM: Oryza sativa

<400> SEQUENCE: 17

Met Gly Thr Ser Ser Arg Pro Thr Val Lys Glu Gly Lys Lys Leu
1               5                   10                  15

Glu Ala Pro Arg Arg Ala Gly Ser His Ala Val Lys Arg Ser Pro
            20                  25                  30

Val Asp Lys Pro Pro Phe Thr Leu Gly Asp Ile Arg Lys Ala Ile Pro
        35                  40                  45

Pro His Cys Phe His Arg Ser Val Ile Lys Ser Phe Ser Tyr Leu Leu
    50                  55                  60

His Asp Leu Ala Ile Ala Ala Gly Leu Leu Tyr Phe Ala Leu Val Val
65                  70                  75                  80

Ile Pro Ala Leu Pro Gly Val Leu Arg Leu Val Ala Trp Pro Phe Tyr
                85                  90                  95

Trp Ala Ala Gln Gly Cys Phe Leu Phe Gly Val Trp Ile Ile Ala His
            100                 105                 110

Glu Cys Gly His His Ala Phe Ser Gly His Ala Leu Asp Asp Thr
        115                 120                 125

Leu Gly Leu Val Leu His Ser Trp Leu Leu Ala Pro Tyr Phe Ser Trp
    130                 135                 140

Lys Tyr Thr His Gln Arg His His Ser Asn Thr Ser Ser Gln Glu Arg
145                 150                 155                 160

Asp Glu Val Phe Val Pro Arg Phe Lys Ser Asp Leu Pro Trp Tyr Ser
                165                 170                 175

Pro Tyr Val Tyr Lys Tyr Asn Asn Pro Val Ala Arg Leu Leu Leu Leu
            180                 185                 190

Val Val Gln Leu Thr Val Gly Trp Pro Met Tyr Leu Val Phe Asn Thr
        195                 200                 205

Trp Gly Arg Gln Tyr Pro Arg Phe Ala Ser His Phe Asp Pro Ser Gly
    210                 215                 220

Pro Ile Tyr Lys Gly Arg Glu Arg Val Phe Ile Ala Ile Ser Asp Ile
225                 230                 235                 240

Gly Met Leu Ala Val Ser Leu Ala Leu Tyr Arg Leu Ala Glu Gly Tyr
                245                 250                 255

Gly Phe Trp Trp Val Val Arg Val Tyr Gly Val Pro Leu Leu Val Val
            260                 265                 270

Asn Ala Trp Leu Val Val Val Thr Tyr Leu His His Thr His Arg Ala
        275                 280                 285

Ile Pro His Tyr Asp Ser Ser Glu Trp Asp Trp Leu Arg Gly Ala Leu
    290                 295                 300

Ala Thr Val Asp Arg Asp Tyr Ser Phe Leu Asn Arg Val Phe His Asn
305                 310                 315                 320

Ile Thr Asp Thr His Val Val His His Leu Phe Pro Thr Ile Pro His
                325                 330                 335

Tyr His Ala Val Glu Ala Thr Lys Ala Ile Arg Pro Ile Leu Gly Glu
            340                 345                 350

Tyr Tyr Gln Phe Asp Pro Thr Pro Ile Val Lys Ala Ile Trp Arg Glu
        355                 360                 365

Ala Lys Glu Cys Ile Tyr Ile Gln Ser Glu Asp His Lys Gly Val Phe
    370                 375                 380

Trp Tyr Ser Asn Lys Phe
385                 390

<210> SEQ ID NO 18
<211> LENGTH: 223
<212> TYPE: PRT
<213> ORGANISM: Oryza sativa

<400> SEQUENCE: 18

```
Met Ala Gly Gly Arg Arg Trp Gly Gly Trp Arg Glu Gln Glu Pro Pro
1               5                   10                  15

Arg Arg Ala Gly Ser Ser Ala Ala Val Gln Arg Phe His Arg Ser Val
            20                  25                  30

Ile Lys Ser Phe Ser Tyr Leu Leu Arg Asp Val Ala Ile Ala Ala Gly
        35                  40                  45

Leu Leu Asn Phe Ala Leu Val Gly Ile Pro Val Leu Pro Ala Gly Val
50                      55                  60

Leu Arg Pro Pro Arg Arg Leu Ala Val Leu Leu Gly Arg Ala Gly Leu
65                  70                  75                  80

Leu Pro Val Arg Gly Val Asp His Arg Ala Arg Val Arg Ala Pro Arg
            85                  90                  95

Ala Pro Arg Arg His Pro Arg Ser Gly Pro Ala Leu Val Ala Ser Gly
            100                 105                 110

Thr Ile Leu Leu Val Glu Ile Gln Pro Pro Ala Ala Pro Leu Gln His
        115                 120                 125

Gln Leu Thr Gly Ala Arg Arg Gly Val Arg Pro Gln Val Gln Val Arg
    130                 135                 140

Ser Ala Val Glu Leu Pro Val Arg Val Gln Val Gln Arg Pro Val
145                 150                 155                 160

Ala Arg Leu Leu Leu Leu Gly Met Gln Leu Thr Val Gly Trp Pro Met
                165                 170                 175

Tyr Leu Val Phe Asn Thr Trp Gly Arg Trp Tyr Pro Arg Phe Ala Ser
                180                 185                 190

His Phe Asp Pro Ser Gly Ala Ile Tyr Met Arg Arg Glu Arg Val Phe
            195                 200                 205

Ile Ala Ile Ser Asp Ile Gly Met Leu Ala Val Ser Leu Ala Leu
        210                 215                 220

<210> SEQ ID NO 19
<211> LENGTH: 1267
<212> TYPE: DNA
<213> ORGANISM: Oryza sativa

<400> SEQUENCE: 19
acggtggtgg agggggaagaa acaggagcta ctactccgcc gttccggcag cagcgcagcc      60
atgcagcgct caccggtgga caaaccgccg ttcacgctgg gggacataaa gaaggccatc     120
ccgccgcact gcttccaccg ctccgtgatc aagtcattct cctacctgct ccacgacctt     180
gccatcgccg ctggcctcct ctactttgct ctggtcggca tccctgccct cccaagcatc     240
ctccgcctcg tcgcctggcc gctctactgg gccgcgcagg gcagtgtact caccggcgtg     300
tgggtcatcg ggcacgagtg tggccaccac gccttctcgg actacttgct cctcgacaac     360
ctcgtgggcc tagtgctcca ctcggcgctt ctcacgccct tcttctcgtg gaagtacagc     420
caccggcggc accgccaa caccggctcc atggagaaag acgaggtgta cgtcgcgaag     480
aagaagtccg cgctgccgtg gtacacccc tacgtgttcg caacccgt cgggcggctg     540 gtgtacatcg ccctgcagct cacctcgcg tggccactct acctcgcgtt caacctgtcc     600
gggcagccgt acccacgcct cgtcacctgc cactacgacc cctacagccc gctgttcagc     660
gaccaggagc gcgtccaagt cctcgtctcc gacgccgcca tcctggccgt gctgctcgcg     720
ctgcacaggc tgacggcggc gtacgggctc tggtgggtgg tgcgcgtgta cggcgtgccg     780
gtgatgatcg tgggcgcgct gttcgtgctc atcacgtacc tgcaccacac ccaccgggcg     840
ctcccgcact acgactccag cgagtgggag tggctgcgtg gctcgctcgc caccgtcgac     900
```

```
cgcgactacg gcgtcctcaa ccgcgtgctg cacaacgtca cggacacgca cgtcctccac      960
cacctcttcc ccagcatgcc acactaccac gccatggagg ccaccagggc agcgaggccc     1020
gtcctcggtg agtactacaa gtttgaccgc acgcccatca tcgaggcaac atggcgtgag     1080
gccaaggagt gcatgtacgt tgagcccagg gagcgcgatg gtatctactg gtacaacaac     1140
aagttttagc tacagacagg ggatgagatt aagatatgat tataagtttt atatacttgg     1200
gtatgtcact gcttctgaat aaatatggtg ctggtctcac ataattaat taaggggacc      1260 ggccaac                                                               1267
```

<210> SEQ ID NO 20
<211> LENGTH: 1491
<212> TYPE: DNA
<213> ORGANISM: Oryza sativa

<400> SEQUENCE: 20

```
cctcctctcc tcctcccctg cacagaccac tcgtttcctc cacaaagagg gagggaacaa       60
gggaagggtg tcgcccgccc cccaccccga tctgcctccg ccgctccgct cctccgcgcc      120
tgcgaaatct accaacgcta actcagcaag atgggtgccg gcggcaggat gacggagaag      180
gagcgggagg agcagcagaa gctgctcggc cgcgccggca atggcgcggc cgtgcagcgg      240
tcgccgacgg acaagccgcc gttcacgctg ggcagatca agaaggccat cccgcctcac       300
tgcttccagc gctcggtgat caagtccttc tcctacgtgg tccatgacct cgtgatcgtc      360
gccgcgctgc tctacttcgc gctggtcatg atccccgtgc tgccgagcgg gatggagttc      420
gcggcatggc cgctctactg gatcgcgcag ggctgcgtgc tcaccggcgt gtgggtcatc      480
gcgcacgagt gcggccacca tgccttctcc gactactcgg tgctcgacga catcgtcggc      540
ctcgtgctgc actcgtcgct gctcgtcccc tacttctcgt ggaagtacag ccaccggcgc      600
caccactcca acaccgggtc gctggagcgc gacgaggtgt cgtcccgaa gcagaagtcg       660 gcgatggcgt ggtacacccc gtacgtgtac cacaacccga tcggccggct ggtgcacatc      720
ttcgtgcagc tcacccctcgg gtggccgctg tacctgcgct tcaacgtgtc cggccgcccg      780 taccccgcgct tcgcgtgcca cttcgacccc tacgcccga tctacaacga ccgggagcgc      840
gtccagatct tcatctccga cgtcggcgtc gtgtccgcgg ggctcgccct gttcaagctg      900
tcgtcggcgt tcgggttctg gtgggtggtg cgcgtctacg gcgtgccgct gctgatcgtg      960
aacgcgtggc tggtgctcat cacctacctg cagcacaccc accggcgct gccgcactac     1020 gactcgagcg agtgggactg gctccgcggc gcgctggcca ccgtggaccg cgactacggc     1080
atcctcaaca aggtgttcca caacatcacg gacacgcacg tcgcgcacca cctcttctcc     1140
accatgccgc actaccacgc catggaggcc actaaggcga tccgccccat cctcggcgag     1200
tactaccagt tcgacccgac gcccgtcgcc aaggcgacat ggcgcgaggc caaggagtgc     1260
atctacgtcg agcctgagga caacaagggc gtcttctggt acaacaacaa gttctaactg     1320
ctgctgctgt gaaatcagca tcacacatcc atagccaagc agcaaacaaa tttgaagaag     1380
aagattacaa gggaagagaa gatagtgtct tcggaaatcg tcgtagcaag tatccatcca     1440
tccatccaac ccatgaacaa tcgtctatct atccatgcat ctatctatgg t              1491
```

<210> SEQ ID NO 21
<211> LENGTH: 1361
<212> TYPE: DNA
<213> ORGANISM: Oryza sativa

<400> SEQUENCE: 21

```
ttgatgaacg tgttgactga ttgcttcgtg taattgcggt cagcagcagt acgtatgggt      60
accagcagcc ggccgacgac ggtgaaggag gggaagaaac tagaggcgcc ccgccgtgcc     120
ggcagccatg cagccgtgaa gcgctctccg gtggacaagc cgccgttcac gctgggcgac     180
atcagaaagg ccatcccacc gcactgcttc caccgctccg tgatcaagtc attctcctac     240
ctgctccacg accttgccat tgccgcgggc ctcctctact tgctctggt cgtcatccct      300 gccctcccag gcgtcctccg cctcgtcgcc tggccgttct actgggccgc gcaggggtgc     360
ttcctgttcg gggtgtggat catcgcgcac gagtgcgggc accacgcgtt ctcgggccac     420
gcactcctcg acgacaccct cggcctggtc ctgcactcat ggctcctagc gccatacttc     480
tcgtggaaat acacccacca acggcaccac tccaacacga gctcacagga gcgcgacgag     540
gtgttcgtcc caggttcaa gtccgacctg ccgtggtact ccccatacgt gtacaagtac      600
aacaaccccg tcgctcggct gctgctcctc gtcgtgcagc tcaccgtcgg gtggccgatg     660
tatttggtgt tcaacacctg gggtcgccag tacccaaggt tcgccagcca cttcgatccc     720
tctgggccca tctacaaggg gcgggagcgc gtcttcatcg ccatctcgga catcggcatg     780
ctggccgtgt cgctcgcgct gtacaggctt gcggagggtt acgggttttg gtgggtggtg     840
cgcgtctacg gcgtgccgct gcttgtcgtc aacgcgtggc ttgtggtcgt cacgtacctg     900
catcacactc accgggcgat cccacactac gactccagcg agtgggactg gttgcgcggg     960
gcgctcgcca ccgtggaccg cgactacagc ttccttaacc gagtgtttca caacatcacg    1020
gacacacacg tcgtgcacca cctgttccct accatcccgc actaccacgc tgtggaggcg    1080
accaaggcga tccgccctat cctcggcgag tactaccagt tcgatcccac acccatcgtc    1140
aaggcgatat ggcgcgaggc taaggagtgc atctacatcc agtccgagga ccacaagggc    1200
gtcttctggt acagcaacaa gttctagtac ctgtagcagc ggcaagcggg cgtataggaa    1260
gggctgacag aattagccat gtcggtcttg cctcatcgct tcatctaaac ccataatcta    1320
cttgaagtct tgaattaatt gtaaactcaa atgaaattcc c                        1361
```

<210> SEQ ID NO 22
<211> LENGTH: 1173
<212> TYPE: DNA
<213> ORGANISM: Oryza sativa

<400> SEQUENCE: 22

```
atgggtacca gcagccggcc gacgacggtg aaggagggga agaaactaga ggcgccccgc      60
cgtgccggca gccatgcagc cgtgaagcgc tctccggtgg acaagccgcc gttcacgctg     120
ggcgacatca gaaaggccat cccaccgcac tgcttccacc gctccgtgat caagtcattc     180
tcctacctgc tccacgacct tgccattgcc gcgggcctcc tctactttgc tctggtcgtc     240
atccctgccc tccagggcgt cctccgcctc gtcgcctggc cgttctactg ggccgcgcag     300
gggtgcttcc tgttcggggt gtggatcatc gcgcacgagt gcgggcacca cgcgttctcg     360
ggccacgcac tcctcgacga caccctcggc ctggtcctgc actcatggct cctagcgcca     420
tacttctcgt ggaaatacac ccaccaacgg caccactcca acaccagctc acaggagcgc     480
gacgaggtgt tcgtcccag gttcaagtcc gacctgccgt ggtactcccc atacgtgtac     540
aagtacaaca accccgtcgc tcggctgctg ctcctcgtcg tgcagctcac cgtcgggtgg     600
ccgatgtatt tggtgttcaa cacctggggt cgccagtacc caaggttcgc cagccacttc     660
gatccctctg ggcccatcta caaggggcgg gagcgcgtct tcatcgccat ctcggacatc     720
ggcatgctgg ccgtgtcgct cgcgctgtac aggcttgcgg agggttacgg gttttggtgg     780
```

```
gtggtgcgcg tctacggcgt gccgctgctt gtcgtcaacg cgtggcttgt ggtcgtcacg      840
tacctgcatc acactcaccg ggcgatccca cactacgact ccagcgagtg ggactggttg      900
cgcggggcgc tcgccaccgt ggaccgcgac tacagcttcc ttaaccgagt gtttcacaac      960
atcacggaca cacacgtcgt gcaccacctg ttccctacca tcccgcacta ccacgctgtg     1020
gaggcgacca aggcgatccg ccctatcctc ggcgagtact accagttcga tcccacaccc     1080
atcgtcaagg cgatatggcg cgaggctaag gagtgcatct acatccagtc cgaggaccac     1140
aagggcgtct tctggtacag caacaagttc tag                                  1173
```

<210> SEQ ID NO 23
<211> LENGTH: 672
<212> TYPE: DNA
<213> ORGANISM: Oryza sativa

<400> SEQUENCE: 23

```
atggcgggcg acggcggtg gggcggatgg cgtgaacagg agccgcctcg ccgtgccggc       60
agcagtgcag ccgtgcagcg cttccaccgc tccgtgatca agtcattctc ctacctgctc     120
cgtgacgtag ccattgccgc gggcctcctc aactttgcgc tggtcggcat ccctgtcctc     180
cctgcaggcg tcctccggcc gcctcgtcgc ctggccgttc tactgggccg cgcagggctg     240
cttcctgttc gtggtgtgga tcatcgcgca cgagtcgggg caccacgcgc tccaagacga     300
caccctcggt ctggtcctgc acttgtggct tctggcacca tacttctcgt ggaaatacag     360
ccaccagcgg caccactcca acaccagctc acaggagcgc gacgaggtgt tcgtccccag     420
gttcaagtcc gatctgccgt ggaactcccc gtacgtgtac aagtacaaca acggcccgtc     480
gcccggctac tgctcctcgg catgcagctc actgtcgggt ggccgatgta tttggtgttc     540
aacacctggg gtcgctggta cccgcggttc gccagccact tcgatccctc cggagccatc     600
tacatgaggc gggagcgcgt cttcatcgcc atctcggaca tcggcatgct ggccgtgtcg     660
ctcgcgctgt aa                                                         672
```

<210> SEQ ID NO 24
<211> LENGTH: 1167
<212> TYPE: DNA
<213> ORGANISM: Oryza sativa

<400> SEQUENCE: 24

```
atgggtgccg gcggcaggat gacggagaag gagcgggagg agcagcagaa gctgctcggc       60
cgcgccggca atggcgcggc cgtgcagcgg tcgccgacgg acaagccgcc gttcacgctg      120
gggcagatca agaaggccat cccgcctcac tgcttccagc gctcggtgat caagtccttc      180
tcctacgtgg tccatgacct cgtgatcgtc gccgcgctgc tctacttcgc gctggtcatg     240
atccccgtgc tgccgagcgg gatggagttc gcggcatggc cgctctactg gatcgcgcag     300
ggctgcgtgc tcaccggcgt gtgggtcatc gcgcacgagt gcggccacca tgccttctcc     360
gactactcgg tgctcgacga catcgtcggc ctcgtgctgc actcgtcgct gctcgtcccc     420
tacttctcgt ggaagtacag ccaccggcgc caccactcca acaccgggtc gctggagcgc     480
gacgaggtgt tcgtcccgaa gcagaagtcg gcgatggcgt ggtacacccc gtacgtgtac     540
cacaacccga tcgccggct ggtgcacatc ttcgtgcagc tcaccctcgg gtggccgctg     600
tacctggcgt tcaacgtgtc cggccgcccg tacccgcgct cgcgtgcca cttcgacccc     660 tacgcccga tctacaacga ccgggagcgc gtccagatct tcatctccga cgtcggcgtc     720
gtgtccgcgg ggctcgccct gttcaagctg tcgtcggcgt tcgggttctg gtgggtggtg     780
```

```
cgcgtctacg gcgtgccgct gctgatcgtg aacgcgtggc tggtgctcat cacctacctg      840
cagcacaccc acccggcgct gccgcactac gactcgagcg agtgggactg gctccgcggc      900
gcgctggcca ccgtggaccg cgactacggc atcctcaaca aggtgttcca caacatcacg      960
gacacgcacg tcgcgcacca cctcttctcc accatgccgc actaccacgc catggaggcc     1020
actaaggcga tccgccccat cctcggcgag tactaccagt tcgacccgac gcccgtcgcc     1080
aaggcgacat ggcgcgaggc caaggagtgc atctacgtcg agcctgagga caacaagggc     1140
gtcttctggt acaacaacaa gttctaa                                         1167
```

<210> SEQ ID NO 25
<211> LENGTH: 1089
<212> TYPE: DNA
<213> ORGANISM: Oryza sativa

<400> SEQUENCE: 25

```
atgcagcgct caccggtgga caaaccgccg ttcacgctgg gggacataaa gaaggccatc       60
ccgccgcact gcttccaccg ctccgtgatc aagtcattct cctacctgct ccacgacctt      120
gccatcgccg ctggcctcct ctactttgct ctggtcggca tccctgccct cccaagcatc      180
ctccgcctcg tcgcctggcc gctctactgg gccgcgcagg gcagtgtact caccggcgtg      240
tgggtcatcg gcacgagtg tggccaccac gccttctcgg actacttgct cctcgacaac      300
ctcgtgggcc tagtgctcca ctcggcgctt ctcacgccct tcttctcgtg gaagtacagc      360
caccggcggc accacgccaa caccggctcc atggagaaag acgaggtgta cgtcgcgaag      420
aagaagtccg cgctgccgtg gtacaccccg tacgtgttcg caacccccgt cgggcggctg      480
gtgtacatcg ccctgcagct caccctcgcg tggccactct acctcgcgtt caacctgtcc      540
gggcagccgt acccacgcct cgtcacctgc cactacgacc cctacagccc gctgttcagc      600
gaccaggagc gcgtccaagt cctcgtctcc gacgccgcca tcctggccgt gctgctcgcg      660
ctgcacaggc tgacggcggc gtacgggctc tggtgggtgg tgcgcgtgta cggcgtgccg      720
gtgatgatcg tgggcgcgct gttcgtgctc atcacgtacc tgcaccacac ccacggggcg      780
ctcccgcact acgactccag cgagtgggag tggctgcgtg gctcgctcgc caccgtcgac      840
cgcgactacg gcgtcctcaa ccgcgtgctg cacaacgtca cggacacgca cgtcctccac      900
cacctcttcc ccagcatgcc acactaccac gccatggagg ccaccagggc agcgaggccc      960
gtcctcggtg agtactacaa gtttgaccgc acgcccatca tcgaggcaac atggcgtgag     1020
gccaaggagt gcatgtacgt tgagcccagg gagcgcgatg tatctactg gtacaacaac     1080 aagttttag                                                             1089
```

<210> SEQ ID NO 26
<211> LENGTH: 6
<212> TYPE: PRT
<213> ORGANISM: Artificial
<220> FEATURE:
<223> OTHER INFORMATION: FatB consensus sequence

<400> SEQUENCE: 26

Asn Gln His Val Asn Asn
1               5

<210> SEQ ID NO 27
<211> LENGTH: 21
<212> TYPE: PRT
<213> ORGANISM: Artificial
<220> FEATURE:

```
<223> OTHER INFORMATION: Fad2 consensus sequence

<400> SEQUENCE: 27

Phe Ser Tyr Val Val His Asp Leu Val Ile Val Ala Ala Leu Leu Phe
1               5                   10                  15

Ala Leu Val Met Ile
            20

<210> SEQ ID NO 28
<211> LENGTH: 19
<212> TYPE: PRT
<213> ORGANISM: Artificial
<220> FEATURE:
<223> OTHER INFORMATION: Fad2 consensus sequence

<400> SEQUENCE: 28

Ala Trp Pro Leu Tyr Ile Ala Gln Gly Cys Val Leu Thr Gly Val Trp
1               5                   10                  15

Val Ile Ala

<210> SEQ ID NO 29
<211> LENGTH: 21
<212> TYPE: PRT
<213> ORGANISM: Artificial
<220> FEATURE:
<223> OTHER INFORMATION: Fad2 consensus sequence

<400> SEQUENCE: 29

Ile Ser Asp Val Gly Val Ser Ala Gly Leu Ala Leu Phe Lys Leu Ser
1               5                   10                  15

Ser Ala Phe Gly Phe
            20

<210> SEQ ID NO 30
<211> LENGTH: 23
<212> TYPE: PRT
<213> ORGANISM: Artificial
<220> FEATURE:
<223> OTHER INFORMATION: Fad2 consensus sequence

<400> SEQUENCE: 30

Val Val Arg Val Tyr Gly Val Pro Leu Leu Ile Val Asn Ala Trp Leu
1               5                   10                  15

Val Leu Ile Thr Tyr Leu Gln
            20

<210> SEQ ID NO 31
<211> LENGTH: 6
<212> TYPE: PRT
<213> ORGANISM: Artificial
<220> FEATURE:
<223> OTHER INFORMATION: Fad2 consensus sequence

<400> SEQUENCE: 31

His Glu Cys Gly His His
1               5

<210> SEQ ID NO 32
<211> LENGTH: 6
<212> TYPE: PRT
<213> ORGANISM: Artificial
<220> FEATURE:
<223> OTHER INFORMATION: Fad2 consensus sequence

<400> SEQUENCE: 32
```

His Arg Arg His His Ala
1               5

<210> SEQ ID NO 33
<211> LENGTH: 5
<212> TYPE: PRT
<213> ORGANISM: Artificial
<220> FEATURE:
<223> OTHER INFORMATION: Fad2 consensus sequence

<400> SEQUENCE: 33

His Val Ala His His
1               5

<210> SEQ ID NO 34
<211> LENGTH: 20
<212> TYPE: DNA
<213> ORGANISM: Artificial
<220> FEATURE:
<223> OTHER INFORMATION: Oligonucleotide primer

<400> SEQUENCE: 34
cgctgctacc aaacaattca                                        20

<210> SEQ ID NO 35
<211> LENGTH: 19
<212> TYPE: DNA
<213> ORGANISM: Artificial
<220> FEATURE:
<223> OTHER INFORMATION: Oligonucleotide primer

<400> SEQUENCE: 35
ttctgtgttg ccatcatcg                                         19

<210> SEQ ID NO 36
<211> LENGTH: 24
<212> TYPE: DNA
<213> ORGANISM: Artificial
<220> FEATURE:
<223> OTHER INFORMATION: Oligonucleotide primer

<400> SEQUENCE: 36
caggaaataa agttggtgat gatg                                   24

<210> SEQ ID NO 37
<211> LENGTH: 24
<212> TYPE: DNA
<213> ORGANISM: Artificial
<220> FEATURE:
<223> OTHER INFORMATION: Oligonucleotide primer

<400> SEQUENCE: 37
cttcacaata tcagctcctg actc                                   24

<210> SEQ ID NO 38
<211> LENGTH: 24
<212> TYPE: DNA
<213> ORGANISM: Artificial
<220> FEATURE:
<223> OTHER INFORMATION: Oligonucleotide primer

<400> SEQUENCE: 38
caggaaataa agttggtgat gatg                                   24

<210> SEQ ID NO 39
<211> LENGTH: 21
<212> TYPE: DNA

```
<213> ORGANISM: Artificial
<220> FEATURE:
<223> OTHER INFORMATION: Oligonucleotide primer

<400> SEQUENCE: 39
cttcacaatg tcagccttca c                                              21

<210> SEQ ID NO 40
<211> LENGTH: 19
<212> TYPE: DNA
<213> ORGANISM: Artificial
<220> FEATURE:
<223> OTHER INFORMATION: Oligonucleotide primer

<400> SEQUENCE: 40
acaggcctga ctccacgat                                                 19

<210> SEQ ID NO 41
<211> LENGTH: 20
<212> TYPE: DNA
<213> ORGANISM: Artificial
<220> FEATURE:
<223> OTHER INFORMATION: Oligonucleotide primer

<400> SEQUENCE: 41
gtccagagtg cttgttgcag                                                20

<210> SEQ ID NO 42
<211> LENGTH: 20
<212> TYPE: DNA
<213> ORGANISM: Artificial
<220> FEATURE:
<223> OTHER INFORMATION: Oligonucleotide primer

<400> SEQUENCE: 42
tacccactcc ctccttgagc                                                20

<210> SEQ ID NO 43
<211> LENGTH: 20
<212> TYPE: DNA
<213> ORGANISM: Artificial
<220> FEATURE:
<223> OTHER INFORMATION: Oligonucleotide primer

<400> SEQUENCE: 43
aggcactgtt ggtgatctcg                                                20

<210> SEQ ID NO 44
<211> LENGTH: 20
<212> TYPE: DNA
<213> ORGANISM: Artificial
<220> FEATURE:
<223> OTHER INFORMATION: Oligonucleotide primer

<400> SEQUENCE: 44
cacaaagagg gagggaacaa                                                20

<210> SEQ ID NO 45
<211> LENGTH: 20
<212> TYPE: DNA
<213> ORGANISM: Artificial
<220> FEATURE:
<223> OTHER INFORMATION: Oligonucleotide primer

<400> SEQUENCE: 45
gaaggacttg atcaccgagc                                                20
```

```
<210> SEQ ID NO 46
<211> LENGTH: 20
<212> TYPE: DNA
<213> ORGANISM: Artificial
<220> FEATURE:
<223> OTHER INFORMATION: Oligonucleotide primer

<400> SEQUENCE: 46
cacaacatca cggacacaca                                                   20

<210> SEQ ID NO 47
<211> LENGTH: 20
<212> TYPE: DNA
<213> ORGANISM: Artificial
<220> FEATURE:
<223> OTHER INFORMATION: Oligonucleotide primer

<400> SEQUENCE: 47
gcaagaccga catggctaat                                                   20

<210> SEQ ID NO 48
<211> LENGTH: 19
<212> TYPE: DNA
<213> ORGANISM: Artificial
<220> FEATURE:
<223> OTHER INFORMATION: Oligonucleotide primer

<400> SEQUENCE: 48
acgtcctcca ccacctctt                                                    19

<210> SEQ ID NO 49
<211> LENGTH: 22
<212> TYPE: DNA
<213> ORGANISM: Artificial
<220> FEATURE:
<223> OTHER INFORMATION: Oligonucleotide primer

<400> SEQUENCE: 49
cagaagcagt gacataccca ag                                                22

<210> SEQ ID NO 50
<211> LENGTH: 20
<212> TYPE: DNA
<213> ORGANISM: Artificial
<220> FEATURE:
<223> OTHER INFORMATION: Oligonucleotide primer

<400> SEQUENCE: 50
tacccactcc ctccttgagc                                                   20

<210> SEQ ID NO 51
<211> LENGTH: 20
<212> TYPE: DNA
<213> ORGANISM: Artificial
<220> FEATURE:
<223> OTHER INFORMATION: Oligonucleotide primer

<400> SEQUENCE: 51
aggcactgtt ggtgatctcg                                                   20

<210> SEQ ID NO 52
<211> LENGTH: 33
<212> TYPE: DNA
<213> ORGANISM: Artificial
<220> FEATURE:
<223> OTHER INFORMATION: Oligonucleotide primer
```

```
<400> SEQUENCE: 52
aaaggatcct ctagagggag gagcagcaga agc                                33

<210> SEQ ID NO 53
<211> LENGTH: 35
<212> TYPE: DNA
<213> ORGANISM: Artificial
<220> FEATURE:
<223> OTHER INFORMATION: Oligonucleotide primer

<400> SEQUENCE: 53
aaaactagtg aattctacac gtacggggtg tacca                              35

<210> SEQ ID NO 54
<211> LENGTH: 24
<212> TYPE: DNA
<213> ORGANISM: Artificial
<220> FEATURE:
<223> OTHER INFORMATION: Oligonucleotide primer

<400> SEQUENCE: 54
agtcatggct ggttctcttg cggc                                          24

<210> SEQ ID NO 55
<211> LENGTH: 24
<212> TYPE: DNA
<213> ORGANISM: Artificial
<220> FEATURE:
<223> OTHER INFORMATION: Oligonucleotide primer

<400> SEQUENCE: 55
accatcacct aagagaccag cagt                                          24

<210> SEQ ID NO 56
<211> LENGTH: 16
<212> TYPE: PRT
<213> ORGANISM: Oryza sativa

<400> SEQUENCE: 56

Cys Gly Met Asn Lys Asn Thr Arg Arg Leu Ser Lys Met Pro Asp Glu
 1               5                  10                  15

<210> SEQ ID NO 57
<211> LENGTH: 10
<212> TYPE: PRT
<213> ORGANISM: Oryza sativa

<400> SEQUENCE: 57

Thr Arg Arg Leu Ser Lys Met Pro Asp Glu
 1               5                  10

<210> SEQ ID NO 58
<211> LENGTH: 17
<212> TYPE: PRT
<213> ORGANISM: Oryza sativa

<400> SEQUENCE: 58

Cys Gly Glu Lys Gln Trp Thr Leu Leu Asp Trp Lys Pro Lys Lys Pro
 1               5                  10                  15

Asp

<210> SEQ ID NO 59
<211> LENGTH: 16
<212> TYPE: PRT
<213> ORGANISM: Oryza sativa
```

<400> SEQUENCE: 59

Cys Gly Ala Gln Gly Glu Gly Asn Met Gly Phe Phe Pro Ala Glu Ser
1               5                   10                  15

<210> SEQ ID NO 60
<211> LENGTH: 21
<212> TYPE: DNA
<213> ORGANISM: Artificial
<220> FEATURE:
<223> OTHER INFORMATION: Oligonucleotide primer

<400> SEQUENCE: 60
gtgccggcgg caggatgacg g                                         21

<210> SEQ ID NO 61
<211> LENGTH: 21
<212> TYPE: DNA
<213> ORGANISM: Artificial
<220> FEATURE:
<223> OTHER INFORMATION: Oligonucleotide primer

<400> SEQUENCE: 61
gccgacgatg tcgtcgagca c                                         21

<210> SEQ ID NO 62
<211> LENGTH: 20
<212> TYPE: DNA
<213> ORGANISM: Artificial
<220> FEATURE:
<223> OTHER INFORMATION: Oligonucleotide primer

<400> SEQUENCE: 62
tgccttctcc gactactcgg                                           20

<210> SEQ ID NO 63
<211> LENGTH: 21
<212> TYPE: DNA
<213> ORGANISM: Artificial
<220> FEATURE:
<223> OTHER INFORMATION: Oligonucleotide primer

<400> SEQUENCE: 63
cctcgcgcca tgtcgccttg g                                         21

<210> SEQ ID NO 64
<211> LENGTH: 19
<212> TYPE: RNA
<213> ORGANISM: Artificial
<220> FEATURE:
<223> OTHER INFORMATION: RNAi molecule

<400> SEQUENCE: 64
ggagcgggag gagcagcag                                            19

<210> SEQ ID NO 65
<211> LENGTH: 19
<212> TYPE: RNA
<213> ORGANISM: Artificial
<220> FEATURE:
<223> OTHER INFORMATION: RNAi molecule

<400> SEQUENCE: 65
gcugcucggc cgcgccggc                                            19

<210> SEQ ID NO 66

```
<211> LENGTH: 19
<212> TYPE: RNA
<213> ORGANISM: Artificial
<220> FEATURE:
<223> OTHER INFORMATION: RNAi molecule

<400> SEQUENCE: 66
uggcgcggcc gugcagcgg                                                        19

<210> SEQ ID NO 67
<211> LENGTH: 19
<212> TYPE: RNA
<213> ORGANISM: Artificial
<220> FEATURE:
<223> OTHER INFORMATION: RNAi molecule

<400> SEQUENCE: 67
gccgccguuc acgcuggggg                                                       19

<210> SEQ ID NO 68
<211> LENGTH: 19
<212> TYPE: RNA
<213> ORGANISM: Artificial
<220> FEATURE:
<223> OTHER INFORMATION: RNAi molecule

<400> SEQUENCE: 68
gaaggccauc ccgccucac                                                        19

<210> SEQ ID NO 69
<211> LENGTH: 19
<212> TYPE: RNA
<213> ORGANISM: Artificial
<220> FEATURE:
<223> OTHER INFORMATION: RNAi molecule

<400> SEQUENCE: 69
ggccaucccg ccucacugc                                                        19

<210> SEQ ID NO 70
<211> LENGTH: 19
<212> TYPE: RNA
<213> ORGANISM: Artificial
<220> FEATURE:
<223> OTHER INFORMATION: RNAi molecule

<400> SEQUENCE: 70
guccuucucc uacgugguc                                                        19

<210> SEQ ID NO 71
<211> LENGTH: 19
<212> TYPE: RNA
<213> ORGANISM: Artificial
<220> FEATURE:
<223> OTHER INFORMATION: RNAi molecule

<400> SEQUENCE: 71
guacagccac cggcgccac                                                        19

<210> SEQ ID NO 72
<211> LENGTH: 19
<212> TYPE: RNA
<213> ORGANISM: Artificial
<220> FEATURE:
<223> OTHER INFORMATION: RNAi molecule

<400> SEQUENCE: 72
```

-continued caccgggucg cuggagcgc                                                    19

<210> SEQ ID NO 73
<211> LENGTH: 19
<212> TYPE: RNA
<213> ORGANISM: Artificial
<220> FEATURE:
<223> OTHER INFORMATION: RNAi molecule

<400> SEQUENCE: 73
gcagaagucg gcgauggcg                                                    19

<210> SEQ ID NO 74
<211> LENGTH: 19
<212> TYPE: RNA
<213> ORGANISM: Artificial
<220> FEATURE:
<223> OTHER INFORMATION: RNAi molecule

<400> SEQUENCE: 74
gcuccaagaa ugcugcugu                                                    19

<210> SEQ ID NO 75
<211> LENGTH: 19
<212> TYPE: RNA
<213> ORGANISM: Artificial
<220> FEATURE:
<223> OTHER INFORMATION: RNAi molecule

<400> SEQUENCE: 75
gaaugcugcu guuaccggc                                                    19

<210> SEQ ID NO 76
<211> LENGTH: 19
<212> TYPE: RNA
<213> ORGANISM: Artificial
<220> FEATURE:
<223> OTHER INFORMATION: RNAi molecule

<400> SEQUENCE: 76
ugcugcuguu accggcgaa                                                    19

<210> SEQ ID NO 77
<211> LENGTH: 19
<212> TYPE: RNA
<213> ORGANISM: Artificial
<220> FEATURE:
<223> OTHER INFORMATION: RNAi molecule

<400> SEQUENCE: 77
uugccggaga auuugagug                                                    19

<210> SEQ ID NO 78
<211> LENGTH: 19
<212> TYPE: RNA
<213> ORGANISM: Artificial
<220> FEATURE:
<223> OTHER INFORMATION: RNAi molecule

<400> SEQUENCE: 78
uuugaguguc cguggcauu                                                    19

<210> SEQ ID NO 79
<211> LENGTH: 19
<212> TYPE: RNA
<213> ORGANISM: Artificial
<220> FEATURE:

```
<223> OTHER INFORMATION: RNAi molecule

<400> SEQUENCE: 79
agccuaaccc accuccugc                                                    19

<210> SEQ ID NO 80
<211> LENGTH: 19
<212> TYPE: RNA
<213> ORGANISM: Artificial
<220> FEATURE:
<223> OTHER INFORMATION: RNAi molecule

<400> SEQUENCE: 80
cccaccuccu gcagccaug                                                    19

<210> SEQ ID NO 81
<211> LENGTH: 19
<212> TYPE: RNA
<213> ORGANISM: Artificial
<220> FEATURE:
<223> OTHER INFORMATION: RNAi molecule

<400> SEQUENCE: 81
guaaaggcac aggcucaaa                                                    19

<210> SEQ ID NO 82
<211> LENGTH: 19
<212> TYPE: RNA
<213> ORGANISM: Artificial
<220> FEATURE:
<223> OTHER INFORMATION: RNAi molecule

<400> SEQUENCE: 82
aggcacaggc ucaaacccu                                                    19

<210> SEQ ID NO 83
<211> LENGTH: 19
<212> TYPE: RNA
<213> ORGANISM: Artificial
<220> FEATURE:
<223> OTHER INFORMATION: RNAi molecule

<400> SEQUENCE: 83
acccuuccca agguuaaug                                                    19
```